(12) United States Patent
Liang et al.

(10) Patent No.: US 12,403,034 B2
(45) Date of Patent: Sep. 2, 2025

(54) SLEEVE-BASED BODY TEMPERATURE REGULATION

(71) Applicant: Flotherm, Inc., Los Angeles, CA (US)

(72) Inventors: Bradley C Liang, Bloomfield Hills, MI (US); Abhinav Ramani, Los Angeles, CA (US); Brian T. Kannard, Los Angeles, CA (US); Peter Luke Santa Maria, Redwood City, CA (US)

( * ) Notice: Subject to any disclaimer, the term of this patent is extended or adjusted under 35 U.S.C. 154(b) by 331 days.

(21) Appl. No.: 17/962,380

(22) Filed: Oct. 7, 2022

(65) Prior Publication Data

US 2023/0035020 A1 Feb. 2, 2023

Related U.S. Application Data

(63) Continuation-in-part of application No. 16/777,895, filed on Jan. 31, 2020, now abandoned, and a
(Continued)

(51) Int. Cl.
*A61F 7/02* (2006.01)
*A61H 9/00* (2006.01)
*A61F 7/00* (2006.01)

(52) U.S. Cl.
CPC ............. *A61F 7/02* (2013.01); *A61H 9/0092* (2013.01); *A61F 2007/0042* (2013.01);
(Continued)

(58) Field of Classification Search
CPC ...... A61F 2007/0041; A61F 2007/0042; A61F 2007/0043; A61F 2007/0045;
(Continued)

(56) References Cited

U.S. PATENT DOCUMENTS

| 267,435 A | 11/1882 | Leiter |
| 2,153,357 A | 4/1939 | Wente |

(Continued)

FOREIGN PATENT DOCUMENTS

| EP | 0303029 A1 | 2/1989 |
| WO | 9944552 A1 | 9/1999 |
| WO | 2013052281 A1 | 4/2013 |

OTHER PUBLICATIONS

U.S. Appl. No. 63/089,884, filed Oct. 9, 2020, Douglas M. Patton.
(Continued)

*Primary Examiner* — Tigist S Demie
(74) *Attorney, Agent, or Firm* — Chang & Hale LLP

(57) ABSTRACT

A heating system comprises a wearable sleeve, a first heating pad associated with a first portion of the wearable sleeve, a second heating pad associated with a second portion of the wearable sleeve, one or more temperature sensors associated with the wearable sleeve, and control circuitry communicatively coupled to the first heating pad, the second heating pad, and the one or more temperature sensors. The control circuitry is configured to receive one or more temperature signals from the one or more temperature sensors, determine a temperature associated with a patient based on the one or more temperature signals, determine that the temperature is less than a target temperature value, and at least partly in response to said determining that the temperature is less than the target temperature value, activate at least one of the first heating pad or the second heating pad.

20 Claims, 33 Drawing Sheets

Related U.S. Application Data continuation-in-part of application No. 16/777,894, filed on Jan. 31, 2020, now Pat. No. 11,622,883.

(60) Provisional application No. 62/799,479, filed on Jan. 31, 2019, provisional application No. 62/799,507, filed on Jan. 31, 2019.

(52) U.S. Cl.
CPC ......... A61F 2007/0086 (2013.01); A61F 2007/0093 (2013.01); A61F 2007/0096 (2013.01); A61F 2007/0233 (2013.01); A61F 2007/0288 (2013.01); A61H 2201/0207 (2013.01); A61H 2201/5097 (2013.01)

(58) Field of Classification Search
CPC ...... A61F 2007/0047; A61F 2007/0054; A61F 2007/0071; A61F 2007/0091; A61F 2007/0228; A61F 2007/0247; A61F 7/007; A61F 7/02
See application file for complete search history.

(56) References Cited

U.S. PATENT DOCUMENTS

| | | |
|---|---|---|
| 2,531,074 A | 11/1950 | Miller |
| 2,541,159 A | 2/1951 | Geiger |
| 2,796,636 A | 6/1957 | Heerwagen |
| 4,029,087 A | 6/1977 | Dye et al. |
| 4,107,509 A | 8/1978 | Scher et al. |
| 4,149,612 A | 4/1979 | Bschorr |
| 4,177,876 A | 12/1979 | Pujolle |
| 4,325,461 A | 4/1982 | Bschorr |
| 4,371,858 A | 2/1983 | Kanoi et al. |
| 4,442,419 A | 4/1984 | Kanoi et al. |
| 4,514,714 A | 4/1985 | Kanoi et al. |
| 4,624,244 A | 11/1986 | Taheri |
| 4,688,572 A | 8/1987 | Hubbard et al. |
| 4,865,020 A | 9/1989 | Bullard |
| 5,007,411 A | 4/1991 | Dye |
| 5,074,285 A | 12/1991 | Wright |
| 5,190,032 A | 3/1993 | Zacoi |
| 5,372,608 A | 12/1994 | Johnson |
| 5,405,671 A | 4/1995 | Kamin et al. |
| 5,411,541 A | 5/1995 | Bell et al. |
| 5,521,341 A | 5/1996 | Stief et al. |
| 5,587,564 A | 12/1996 | Stief et al. |
| 5,626,556 A | 5/1997 | Tobler et al. |
| 5,674,262 A | 10/1997 | Tumey |
| 5,851,626 A | 12/1998 | McCorry et al. |
| 6,254,554 B1 | 7/2001 | Turtzo |
| 6,375,673 B1 | 4/2002 | Clifton et al. |
| 6,375,674 B1 | 4/2002 | Carson |
| 6,387,065 B1 | 5/2002 | Tumey |
| 6,478,110 B1 | 11/2002 | Eatwell et al. |
| 6,792,907 B1 | 9/2004 | Kostun et al. |
| 7,074,177 B2 | 7/2006 | Pickett et al. |
| 7,196,289 B2 | 3/2007 | Ellis et al. |
| 7,249,653 B2 | 7/2007 | Sheng et al. |
| 7,263,028 B2 | 8/2007 | Thomas et al. |
| 7,395,898 B2 | 7/2008 | Yang et al. |
| 7,510,052 B2 | 3/2009 | Ayle |
| 7,959,657 B1 | 6/2011 | Harsy |
| 7,972,287 B2 | 7/2011 | Stewart et al. |
| 8,011,472 B2 | 9/2011 | Tanase et al. |
| 8,034,007 B2 | 10/2011 | Avitable et al. |
| 8,162,863 B2 | 4/2012 | Nardi et al. |
| 8,360,201 B2 | 1/2013 | Tanase |
| 8,391,540 B2 | 3/2013 | Berriman et al. |
| 8,454,542 B2 | 6/2013 | Hirata et al. |
| 8,603,150 B2 | 12/2013 | Kane et al. |
| 8,616,330 B1 | 12/2013 | Mcknight et al. |
| 8,651,229 B2 | 2/2014 | Franzen |
| 9,033,906 B2 | 5/2015 | Nolan et al. |
| 9,144,530 B2 | 9/2015 | Davis et al. |
| 9,284,727 B2 | 3/2016 | McKnight et al. |
| 9,956,113 B2 | 5/2018 | Maria et al. |
| 11,191,667 B2 | 12/2021 | Maria et al. |
| 2002/0107558 A1 | 8/2002 | Clifton et al. |
| 2004/0133135 A1 | 7/2004 | Diana |
| 2004/0210176 A1 | 10/2004 | Diana |
| 2005/0075531 A1 | 4/2005 | Loeb et al. |
| 2005/0103353 A1 | 5/2005 | Grahn et al. |
| 2005/0126578 A1 | 6/2005 | Garrison et al. |
| 2005/0256556 A1 | 11/2005 | Schirrmacher et al. |
| 2006/0004245 A1 | 1/2006 | Pickett et al. |
| 2007/0060988 A1 | 3/2007 | Grenon et al. |
| 2007/0135743 A1 | 6/2007 | Meyer |
| 2008/0021531 A1 | 1/2008 | Kane et al. |
| 2008/0064992 A1 | 3/2008 | Stewart et al. |
| 2008/0099609 A1 | 5/2008 | Drost |
| 2008/0132976 A1 | 6/2008 | Kane et al. |
| 2008/0135327 A1 | 6/2008 | Matsumura et al. |
| 2008/0161891 A1 | 7/2008 | Pierre et al. |
| 2008/0167572 A1 | 7/2008 | Stivoric et al. |
| 2008/0249444 A1 | 10/2008 | Avitable et al. |
| 2008/0249449 A1 | 10/2008 | Brown et al. |
| 2009/0069731 A1 | 3/2009 | Parish et al. |
| 2009/0099629 A1 | 4/2009 | Carson et al. |
| 2009/0177184 A1 | 7/2009 | Christensen et al. |
| 2009/0221943 A1 | 9/2009 | Burbank et al. |
| 2009/0227922 A1 | 9/2009 | Nardi et al. |
| 2009/0228082 A1 | 9/2009 | Ross, III et al. |
| 2009/0233045 A1 | 9/2009 | Slama et al. |
| 2009/0260639 A1 | 10/2009 | Hsu et al. |
| 2009/0270910 A1 | 10/2009 | Hargens et al. |
| 2010/0042026 A1 | 2/2010 | Kloecker et al. |
| 2010/0042027 A1 | 2/2010 | Hirata et al. |
| 2010/0076356 A1 | 3/2010 | Biondo et al. |
| 2010/0152821 A1 | 6/2010 | Rein et al. |
| 2010/0175949 A1 | 7/2010 | Yamaguchi et al. |
| 2010/0210982 A1 | 8/2010 | Balachandran et al. |
| 2010/0212999 A1 | 8/2010 | Marion et al. |
| 2011/0004132 A1 | 1/2011 | Cook |
| 2011/0051776 A1 | 3/2011 | Bieberich et al. |
| 2011/0098792 A1 | 4/2011 | Lowe et al. |
| 2011/0190675 A1 | 8/2011 | Vess |
| 2011/0251536 A1 | 10/2011 | Wilford et al. |
| 2012/0041351 A1 | 2/2012 | Nolan et al. |
| 2012/0065561 A1 | 3/2012 | Ballas et al. |
| 2012/0065664 A1 | 3/2012 | Avitable et al. |
| 2013/0030331 A1 | 1/2013 | Quisenberry et al. |
| 2013/0052281 A1 | 2/2013 | Farnaby et al. |
| 2013/0087407 A1 | 4/2013 | McKnight et al. |
| 2013/0253383 A1 | 9/2013 | Maxon-Maldonado |
| 2013/0310719 A1 | 11/2013 | Davis et al. |
| 2013/0324895 A1 | 12/2013 | Avitable et al. |
| 2014/0207036 A1 | 7/2014 | Perry et al. |
| 2014/0222121 A1 | 8/2014 | Spence et al. |
| 2014/0276257 A1 | 9/2014 | Maria et al. |
| 2014/0350645 A1 | 11/2014 | Diller et al. |
| 2015/0290065 A1 | 10/2015 | Augustine et al. |
| 2016/0135706 A1 | 5/2016 | Sullivan et al. |
| 2016/0228291 A1 | 8/2016 | Calliser et al. |
| 2016/0262924 A1* | 9/2016 | Abreu ............... A61F 7/007 |
| 2017/0000412 A1* | 1/2017 | Scott ............... A61B 5/02055 |
| 2017/0135855 A1 | 5/2017 | Stefan et al. |
| 2017/0258628 A1 | 9/2017 | Awasthi |
| 2017/0262597 A1 | 9/2017 | Huddar et al. |
| 2018/0271696 A1* | 9/2018 | Santa Maria ....... A61H 9/0078 |
| 2020/0245950 A1 | 8/2020 | Liang et al. |
| 2020/0246180 A1 | 8/2020 | Liang et al. |
| 2021/0038259 A1 | 2/2021 | Angell et al. |
| 2023/0000667 A1 | 1/2023 | Patton et al. |

OTHER PUBLICATIONS

U.S. Appl. No. 63/116,594, filed Nov. 20, 2020, Douglas M. Patton.
U.S. Appl. No. 63/217,692, filed Jul. 1, 2021, Douglas M. Patton.

* cited by examiner

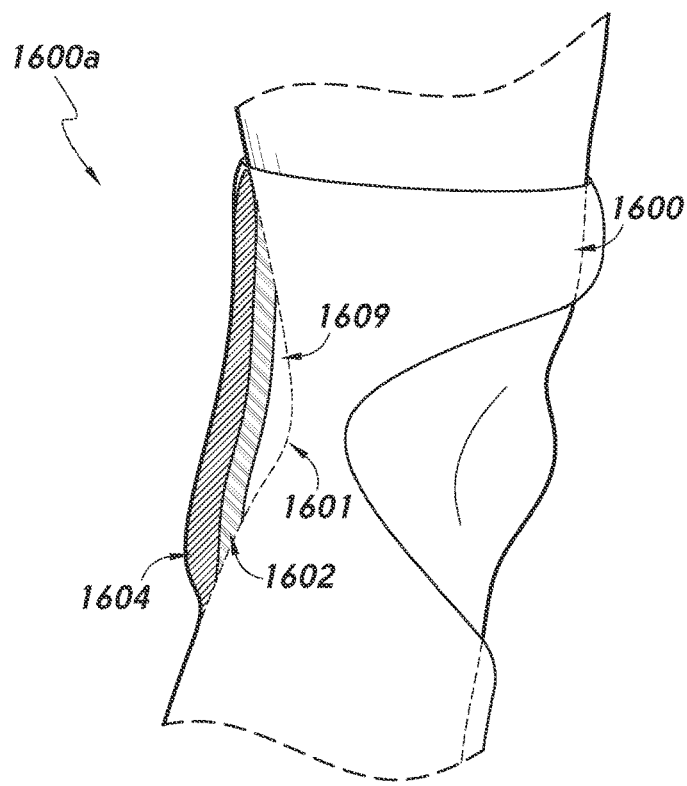
FIG. 16
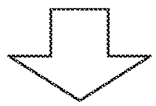
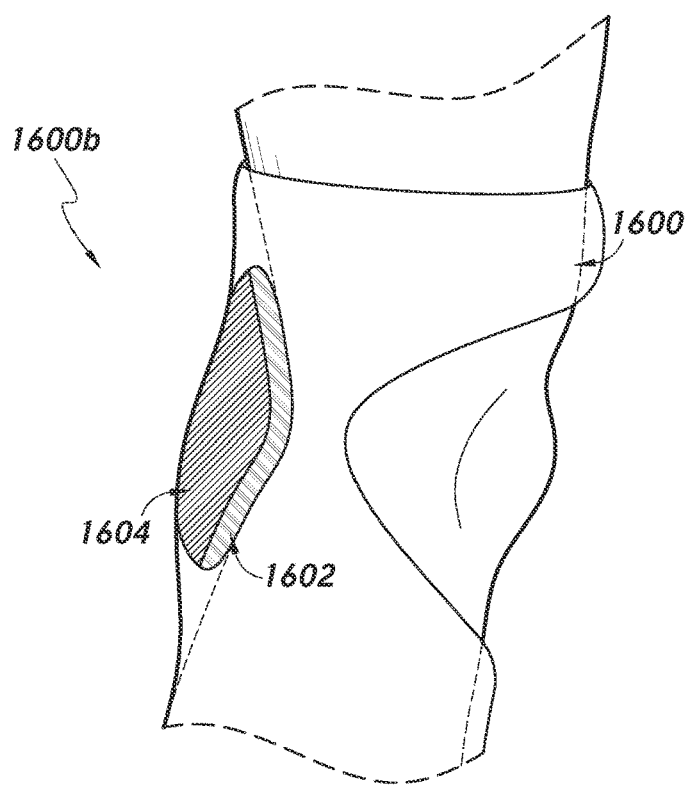

SLEEVE-BASED BODY TEMPERATURE REGULATION

RELATED APPLICATION

This application is a continuation-in-part of U.S. patent application Ser. No. 16/777,894, filed on Jan. 31, 2020, entitled PATIENT TEMPERATURE AND BLOOD FLOW MANAGEMENT, which claims priority to U.S. Provisional Application No. 62/799,479, filed on Jan. 31, 2019, entitled DEVICE FOR ENHANCING BLOOD FLOW AND MAINTAINING NORMOTHERMIA. This application further is a continuation-in-part of U.S. patent application Ser. No. 16/777,895, filed on Jan. 31, 2020, entitled REAL-TIME BODY TEMPERATURE MANAGEMENT, which claims priority to U.S. Provisional Application No. 62/799,507, filed on Jan. 31, 2019, entitled REAL-TIME ASSESSMENT AND REGULATION OF CORE BODY TEMPERATURE. The disclosures of each of the foregoing are hereby incorporated by reference in their entirety.

BACKGROUND

Field

The present application relates to medical devices and methods. More specifically, the application relates to methods, devices and systems for regulating body temperature of a mammal.

Description of Related Art

Each year, over 60 million surgical procedures are performed in the United States. Patient temperatures can drop precipitously during surgery, due to the effects of general anesthesia, lack of insulating clothing, and exposure to cold operating room temperatures.

SUMMARY

Described herein are one or more methods and devices for maintaining normothermia via compression and warming. In some implementations of the present disclosure, a system comprises a first warming element configured to apply warming to the popliteal fossa, a second warming element configured to apply warming to the sole of the foot and a compression element configured to apply compression to the calf.

Some implementations of the present disclosure relate to a system for maintaining normothermia via compression and warming, the system comprising a first warming element configured to apply warming to the popliteal fossa and/or other portion of a patient's body, a second warming element configured to apply warming to the sole of the foot and/or other portion of the patient's body, and a compression element configured to apply compression to the calf.

The first warming element may be configured to apply warming to the popliteal fossa and sole of the foot via conductive means. In some embodiments, warming is applied to the popliteal fossa and sole of the foot through the use of resistive heating. Warming may be applied to the popliteal fossa and sole of the foot through the use of a fluid-warmed bladder. In some embodiments, contact between the first warming element and the popliteal fossa is maintained through the use of a limb-biasing apparatus. The limb-biasing apparatus may comprise one or more of a foam element, a bladder, and a strap positioned between the warming element and an outer sleeve layer. In some embodiments, the limb-biasing apparatus is configured to cause the first warming element to be pressed against the popliteal fossa to establish direct surface contact between the warming element and the popliteal fossa.

In some embodiments, warming is applied to the popliteal fossa and sole of the foot via convective means. Thermally-treated gas or fluid may be provided to the first warming element and the second warming element by way of an air-tight and water-tight hose. In some embodiments, the air-tight and water-tight hose comprises a warming unit for providing a stream of temperature-regulated fluid through channels or bladders. The air-tight and water-tight hose may comprise a heater in the warming unit. In some embodiments, the air-tight and water-tight hose comprises a control circuit in the warming unit. The air-tight and water-tight hose may comprise a limb sleeve with perforation connected to the warming unit. In some embodiments, warming temperature of the first warming element and the second warming element is cyclical so to avoid burning of the skin. The first warming element and the second warming element may be configured to deliver heat that is controlled via pulse-width modulation. In some embodiments, the first warming element and the second warming element are configured to utilize a heat application cycle that may be synced (with some offset) in time to compression cycles of the compression element.

Some implementations of the present disclosure relate to a limb sleeve comprising a first anomaly indicative of knee placement, a second anomaly indicative of heel placement, and a first extendable and collapsible section configured to facilitate placement of the first anomaly and the second anomaly.

In some embodiments, the first extendable and collapsible section comprises an adjustable region to enable the first anomaly and the second anomaly to be stretched prior to application. The first extendable and collapsible section may comprise a self-adhering region. In some embodiments, the first anomaly and the second anomaly comprise one or more of physical, visible, or palpable features.

Some implementations of the present disclosure relate to a connector between a limb sleeve and a controller, the connector comprising an interface configured to create a hermetic seal between at least one of an internal fluid channel and an electric channel and maintain the hermetic seal to an external environment.

The interface may be configured to attach in either of two possible fixation orientations. In some embodiments, the interface can only be attached in a single orientation. The interface may be configured to create a hermetic seal between only one of the internal fluid channel and the electric channel.

Some implementations of the present disclosure involve a method of assessing a patient's risk of hypothermia. The method comprises receiving a first input from a sleeve administered to a patient, receiving a second input, determining a first risk value based at least in part on the first input, determining a second risk value based at least in part on the second input, determining a first relative risk value of the first risk value based at least in part on comparing the first risk value to the second risk value, determining a second relative risk value of the second risk value based at least in part on comparing the first risk value to the second risk value, and generating a risk score for the patient.

The first input may be one of a group comprising core temperature data for the patient, peripheral temperature data, and vital signal data for the patient. In some embodiments, the second input is one of a group comprising demographic data for the patient, comorbidity data/status for the patient, pharmacological data for the patient, procedural data relating to a procedure involving the patient, core temperature data for the patient, peripheral temperature data, environmental data, and vital signal data for the patient. The method may further comprise assigning a first weight value to the first input and assigning a second weight value to the second input. Determining the first relative risk value may involve comparing the first weight value to the second weight value. In some embodiments, the method further comprises adjusting a temperature of the sleeve based at least in part on the risk score. The method may further comprise computing a rate of core temperature change value based at least in part on the first input. In some embodiments, the method further comprises determining a core temperature prediction for the patient based at least in part on the rate of core temperature change value. The method may further comprise adjusting a temperature of the sleeve based at least in part on the risk score.

Some implementations of the present disclosure relate to a method comprising determining a set point core temperature value, measuring a present core temperature value of a patient being treated with a sleeve comprising one or more heating elements, comparing the set point core temperature value to the present core temperature value, in response to determining that the present value is not less than the set point value, comparing the present value to a sum of the set point value and a buffer value, in response to determining that the present value is not greater than the sum, maintaining a temperature setting at a first heating element of the sleeve, and in response to determining that the present value is greater than the sum, decreasing the temperature setting at the first heating element of the sleeve.

In some embodiments, the method further comprises, in response to determining that the present value is less than the set point value, measuring a heating element temperature of the first heating element and comparing the heating element temperature to a safety threshold value. The method may further comprise, in response to determining that the heating element temperature is not greater than the safety threshold value, increasing the heating element temperature. In some embodiments, the method further comprises, in response to determining that the heating element temperature is greater than the safety threshold value, comparing the heating element temperature to a maximum temperature value. The method may further comprise, in response to determining that the heating element temperature is not greater than the maximum temperature value, increasing the heating element temperature. In some embodiments, the method further comprises, in response to determining that the heating element temperature is greater than the maximum temperature value, decreasing the heating element temperature. The method may further comprise, in response to determining that the heating element temperature is greater than the maximum temperature value, comparing a compression frequency of a first compression element at the sleeve to a maximum frequency value. In some embodiments, the method further comprises, in response to determining that the compression frequency is not greater than the maximum frequency value, increasing the compression frequency. The method may further comprise, in response to determining that the compression frequency is greater than the maximum frequency value, maintaining the compression frequency.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

FIG. 16 provides side views of an inflatable sleeve in a deflated state and in an inflated state in accordance with one or more embodiments.

DETAILED DESCRIPTION

Figure 1:
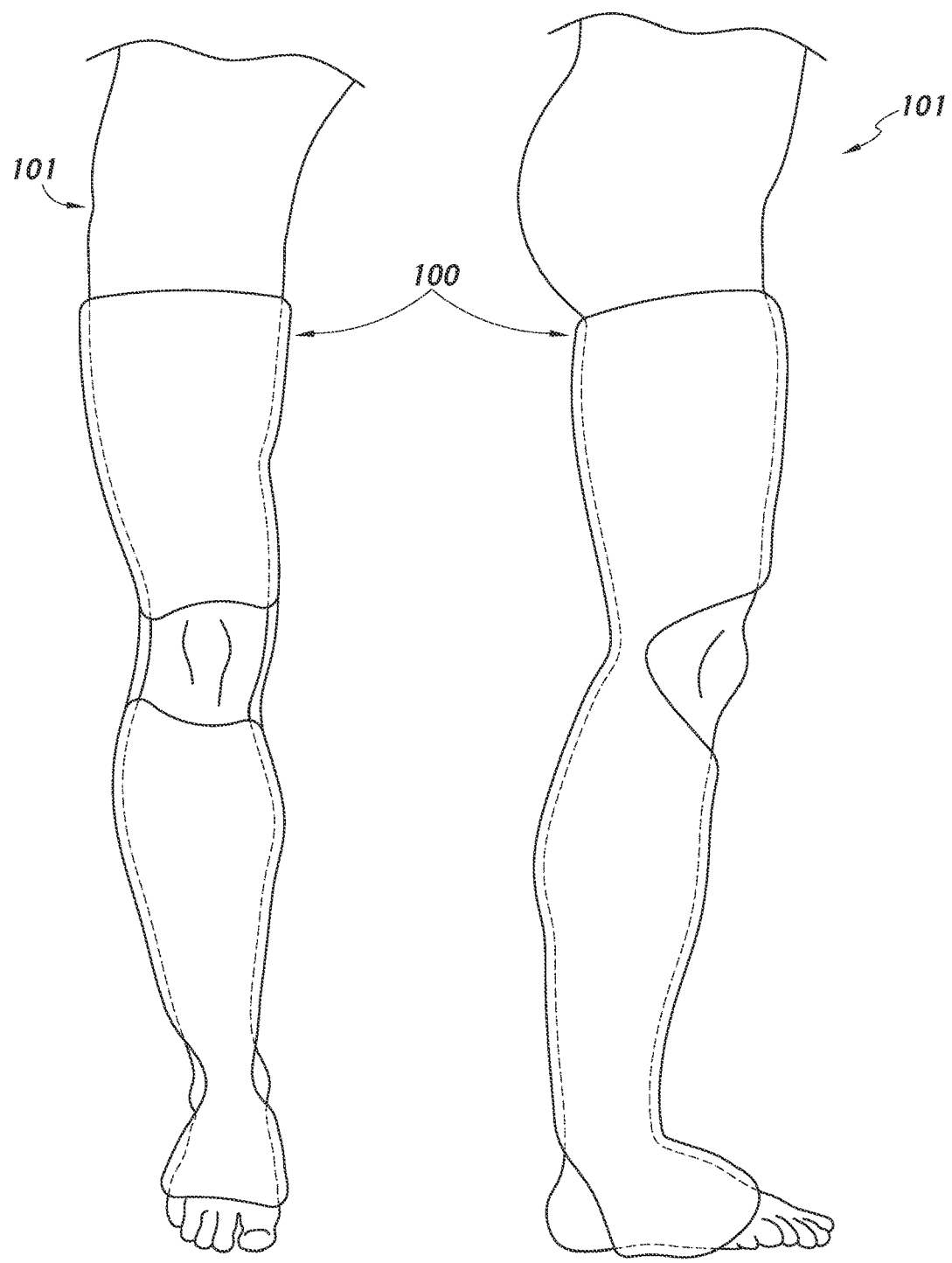
FIG. 1 provides front and side views of a sleeve configured to provide blood flow and/or compression therapy to a patient.

The headings provided herein are for convenience only and do not necessarily affect the scope or meaning of the claimed invention.

Overview

Each year, over 60 million surgical procedures are performed in the United States. While great care may be taken to prevent surgical complications, one commonly overlooked and under-addressed problem is the risk of developing hypothermia before, during, or after surgery (referred to as "inadvertent perioperative hypothermia" or "IPH"). Patient temperatures can drop precipitously during surgery due to the effects of general anesthesia, lack of insulating clothing, and exposure to cold operating room temperatures. Even with today's standard of care, 30-50% of surgical patients may develop hypothermia.

Hypothermia often causes much more than patient discomfort. Patients who suffer even mild IPH can face a significantly elevated risk of developing surgical site infections, cardiac morbidities, intraoperative bleeding, and other avoidable complications. Together, these complications can significantly increase recovery time and overall length of hospital stay, leading to increased costs for all parties. By some estimates, the unmanaged risk for IPH is a $15 billion problem in the United States alone, and yet it is largely overlooked.

Perioperative heat loss can occur predominantly via convective heat transfer, particularly through the palms of the hands, soles of the feet, and exposed surgical site surface area. During preoperative care, patients are often dressed solely in a gown and are often exposed to relatively cold waiting areas with little to no insulation. Although patients are generally only anesthetized at the start of surgery, patients often arrive at the surgical theater moderately hypothermic. This can put a patient at greater risk for developing severe hypothermia once anesthesia has been administered. Postoperative drops in core temperature can increase the likelihood of developing additional comorbidities, such as morbid cardiac outcomes, surgical site infections, and blood loss, any of which can prolong recovery and hospitalization.

Patients undergoing surgery can develop hypothermia during the surgical procedure itself, especially when the procedure involves the patient's core area, such as procedures involving the posterior or anterior sides of the thoracic, abdominal, and pelvic regions. Surgeries of the core involve the exposure of vital internal organs to the colder environment and thus carry a greater risk of hypothermia. Furthermore, core surgeries often necessitate uncovering of the trunk and chest, which render blankets and many other currently-available interventions inadequate. Once in the operating room, patients may be naked and exposed to a room temperature well below 36 degrees Celsius and to cold liquids used to wash the surgical site during sterilization preparation. At the onset of surgery, delivered anesthetics can immediately impair the normal autonomic thermoregulatory controls. Colder blood may be transferred from the peripheries of the body to the core through a phenomenon known as redistributive hypothermia. Vasodilatation and reduction in muscle tone can cause a significant drop in core temperature within the first half-hour of surgery.

Overall, compared to non-hypothermic patients, those who suffer from IPH experience greater rates of surgical site infections, bleeding, and cardiac complications. Such issues may require additional monitoring and/or increase the length of stay and/or subjective discomfort. The development of IPH is strongly correlated with a multitude of physiological organ system changes impacting the cardiovascular, respiratory, neurologic, immunologic, hematologic, drug-metabolic, and wound-healing mechanisms. The incidence of several post-surgical complications can be increased due to even mild hypothermia.

Intraoperatively, hypothermia can cause a decrease in cardiac output and heart rate, which can lead to ventricular dysrhythmias. Platelet functions can become impaired and there can be a decrease in coagulation factors, which can, in turn, lead to greater intraoperative bleeding and blood loss. Impaired immune functions can increase the rate of surgical site infections. Hypothermia is associated with a four-fold increase in surgical wound infection and twice as many morbid cardiac events. In select procedures such as colorectal, gynecologic, or spinal surgery, where infection rates are normally higher than other surgeries, hypothermia can be exceedingly dangerous to the intraoperative and postoperative recovery. These complications and others are supported in multiple studies and can result in both clinical and economic burdens.

Current methods of preventing hypothermia may not be completely effective. Even with the current interventions, up to 46% of patients are reported to be hypothermic at the start of surgery, and 33% are hypothermic upon arrival to the post-anesthesia care unit (PACU). Assuming the cost savings for maintaining normothermia in one patient is approximately $5,000 per patient, and approximately 30% of the 17 million high-risk surgical patients are hypothermic, a system-wide cost savings of $15 billion could be realized by keeping these patients normothermic. With rising healthcare costs and recent initiatives mandating the maintenance of perioperative normothermia, hospital administrators nationally are in need of new, efficacious and cost-effective devices to address perioperative hypothermia, a product space that has seen little innovation since the introduction of the forced-air warming blanket nearly three decades ago.

Some devices for perioperative warming may include forced-air temperature management devices (e.g., warming blankets). Some temperature management solutions utilize high-heat transfer conduction heating blankets and intraoperative hand-warming devices. However, such solutions can be associated with various key shortcomings including, for example: (1) undesirably high risk of contaminating the surgical field (e.g., forced-air methods can blow bacteria-containing air into the surgical field); (2) forced-air devices can get in the way (e.g., to warm the core, forced-air blankets may need to be in contact with the core, which may be near to the surgical site); and (3) operating room staff may turn down the temperature on a device due to their own comfort (e.g., staff members may turn down the patient's forced-air device due to the device heating the surrounding air). Moreover, certain devices may not be used in preoperative warming for one or more of the following reasons, among others: (1) some devices may immobilize the upper limbs, impeding patient mobilization; (2) devices may be cumbersome (e.g., a device may float on the patient and get blown off or fall off during use and/or transport, and they require large, predominantly floor-based blowers that may not be mobile; (3) they may not attach to the patient and/or can become dislodged during transport and obstruct the bed and other monitors and devices; and (4) they can require a conscious administrative decision to implement.

Embodiments of the present disclosure advantageously provide certain improved methods and systems for maintaining a patient's core body temperature before, during, and/or after surgery. Furthermore, embodiments described herein provide methods and systems for core body temperature management in an unobtrusive, effective, and easy-to-use (e.g., easy to set-up) manner. Some embodiments of the present disclosure can be suitable for use before, during, and/or after a surgical procedure and can be acceptable to the patient while awake in the preoperative and/or postoperative settings.

In some embodiments, lower limbs of patients may be leveraged to provide therapy and/or enable mobility. For example, some devices described herein may provide flexibility and/or one or more spaces around a knee, ankle, and/or other portions of a patient's body to allow the patient to flex and/or extend the limbs. Such patient mobility may provide a variety of benefits, including allowing patients to stand up to use the restroom without removing and reapplying the device.

Some embodiments of temperature management devices disclosed herein may be configured to provide warming to one or more arteries and/or veins passing along the patient's lower limbs, for example along the calf. Moreover, some embodiments may involve compression of one or more portions of the patient's body. For example, compression may be applied to the patient's calf. In some embodiments, compression may be performed in a sequential and/or gradient manner.

Some devices, methods, and systems herein advantageously provide for at least partially automated management of patient temperature, limiting the need for clinician input in maintaining patient target temperatures. For example, embodiments of the present disclosure advantageously provide closed-loop temperature-management solutions.

Closed-loop temperature-management may involve at least partially automated adjustment of heat transfer to the body in response to real-time measurement of patient temperature. The automated regulation of heat delivered to a patient may be suitable to improve temperature control through elimination of manual errors and/or improved efficiency (e.g. reduction in time required to adjust therapy). Methods, devices, and systems implementing or relating to the various temperature control determinations and processes disclosed herein for providing therapy automation can greatly reduce and/or potentially eliminate the need for certain types of clinician input and oversight in adjusting temperature and/or blood flow therapy settings/parameters and are well suited towards maintenance of patient temperature at a predetermined set point/value (or within a defined range) throughout the perioperative timeframe.

In some implementations, the present disclosure relates to devices, systems and methods directed toward automated application of warming and blood flow (WBF) therapy to a patient to help regulate body temperature, reduce blood stasis, deep vein thrombosis, pulmonary emboli, and/or optimize blood circulation. WBF therapy can be implemented in the systems, devices and methods described herein to dually increase patient temperature and improve circulation to the body's core from one or more extremities. Patient warming may be accomplished in several different ways, including but not limited to the conductive application of heat to areas on the skin surface of the body. Increased blood circulation may be accomplished in several different ways, including but not limited to intermittent compression, such as in the area of the patient's calf.

In some implementations, the present disclosure relates to systems, devices, and methods for determining patient risk for hypothermia in real-time in response to multiple inputs, including but not limited to core temperature measurement, anesthesia onset (e.g., timestamp), and/or patient demographic information age, sex, weight, etc.). WBF and intermittent compression therapy delivery can be modulated by the system/device(s) in response to patient risk for, detection of, and/or prediction of, oncoming hypothermia.

In some embodiments, systems, devices, and/or methods to enable the real-time determination of patient risk of developing hypothermia are provided. Such systems/devices can include one or more sensors or sensor arrays for continuous monitoring of patient peripheral temperature. Systems/devices of the present disclosure may further comprise one or more electronics modules/controllers configured to power and/or communicate with the sensor(s). Such electronics modules/controllers can include certain control circuitry, includes one or more processors and/or memory/data storage devices that may be configured to determine risk of patient hypothermia based on at least one temperature input, which may advantageously be continuously, periodically, and/or sporadically monitored, in some embodiments, the systems/devices may include one or more electronic visual display devices, interfaces, lights, or other type of visual output for indicating relevant patient metrics (e.g. hypothermia risk). The term. "control circuitry" is used herein according to its broad and ordinary meaning, and may refer to any collection of processors, processing circuitry, processing modules/units, chips, dies (e.g., semiconductor dies including come or more active and/or passive devices and/or connectivity circuitry), microprocessors, microcontrollers, digital signal processors, microcomputers, central processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further comprise one or more, storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry.

In some implementations, the present disclosure relates to systems, devices, and methods involving the application of a physiological heat transfer model to estimate patient tissue and core temperatures, derived from certain available input(s), including but not limited to, for example, peripheral temperature readings.

Some embodiments further utilize one or more sets of primary inputs including but not limited to medical procedural parameters, time-to and -from induction of anesthesia, and patient temperature readings (e.g., actual or estimated core temperature). Some embodiments further include secondary inputs including, for example, information available from a patient's electronic health record (e.g. demographics, comorbidity status, pharmacological agents) or other physiological (e.g. vital signs) or environmental (e.g. room temperature) monitors/parameters.

In some implementations, the present disclosure relates to systems, devices, and methods may include a controller comprising certain control circuitry configured to adjust WBF therapy parameters and/or control operations to maintain normal core body temperatures. In some embodiments, the system controller and/or associated control circuitry may be configured to adjust therapy parameters and/or control operations based at least in part on a determined patient risk level/value of developing hypothermia. In some embodiments, therapy adjustments made by the system/device(s) may be applied dynamically over time.

Although this invention has been described in more detail below, the scope of the invention as set forth in the following description should not be limited by the foregoing descriptions of various embodiments. Thus, it is intended that the scope of the present invention herein disclosed should not be limited by the particular disclosed embodiments, but should be determined only by a fair reading of the content presented herein/herewith.

Limb Sleeve Devices

In some implementations, the present disclosure relates to devices, systems and methods directed toward delivering warming therapy and/or blood flow therapy to a patient to help reduce blood stasis, deep vein thrombosis, and/or pulmonary emboli and/or to help regulate body temperature and/or optimize blood circulation. Warming and/or blood flow therapy can be used in the systems, devices, and methods described herein to help maintain normothermia and/or help return circulation to a body's core, including the heart and lungs, from one or more extremities/limbs. Blood flow therapy and/or blood circulation therapy may be accomplished in a number of different ways, including but not limited to intermittent compression. For example, in some implementations, intermittent compression may be performed through the execution of circumferential compression of one or more limbs. Warming therapy may likewise be accomplished in a variety of different ways, including without limitation through the use of ultrasound, electrical, mechanical, chemical, radiative and/or convective energy.

FIG. 1 provides front and side views of a temperature management sleeve 100 configured to provide blood flow and/or compression therapy to a patient. The term "sleeve" is used herein according to its plain and ordinary meaning and may refer to any device configured to be administered to one or more areas of a human body for delivery of heat and/or compression to the human body. For example, a "sleeve" may be a device configured to provide therapy to a limb or other body part at least in part through physical contact with the skin and/or other feature(s) of the body, wherein such physical contact provides therapy in and of itself or facilitates the provision of therapy through physically securing, positioning, or otherwise arranging one or more therapeutic devices, components, or features coupled to or otherwise associated with the sleeve. In some embodiments, the sleeve 100 may comprise a single continuous form or device and/or may be configured to apply therapy to a patient's thigh, knee, calf, and/or foot, and/or one or more other lower limb portions of a patient's body. The sleeve 100 may be applied to a patient's limb 101 (e.g., a leg, arm, and/or foot) and/or may be configured to deliver warming and/or to apply blood flow therapy to at least one area of the patient's limb 101. In some embodiments, the sleeve 100 may be configured to deliver heat to a majority of, or even the entire, limb 101 in conjunction with blood flow therapy. In some embodiments, the sleeve 100 may be configured to deliver heat to at least two different areas on the limb 101 while applying blood flow therapy between, adjacent to, and/or or overlapping the same areas.

Figure 2:
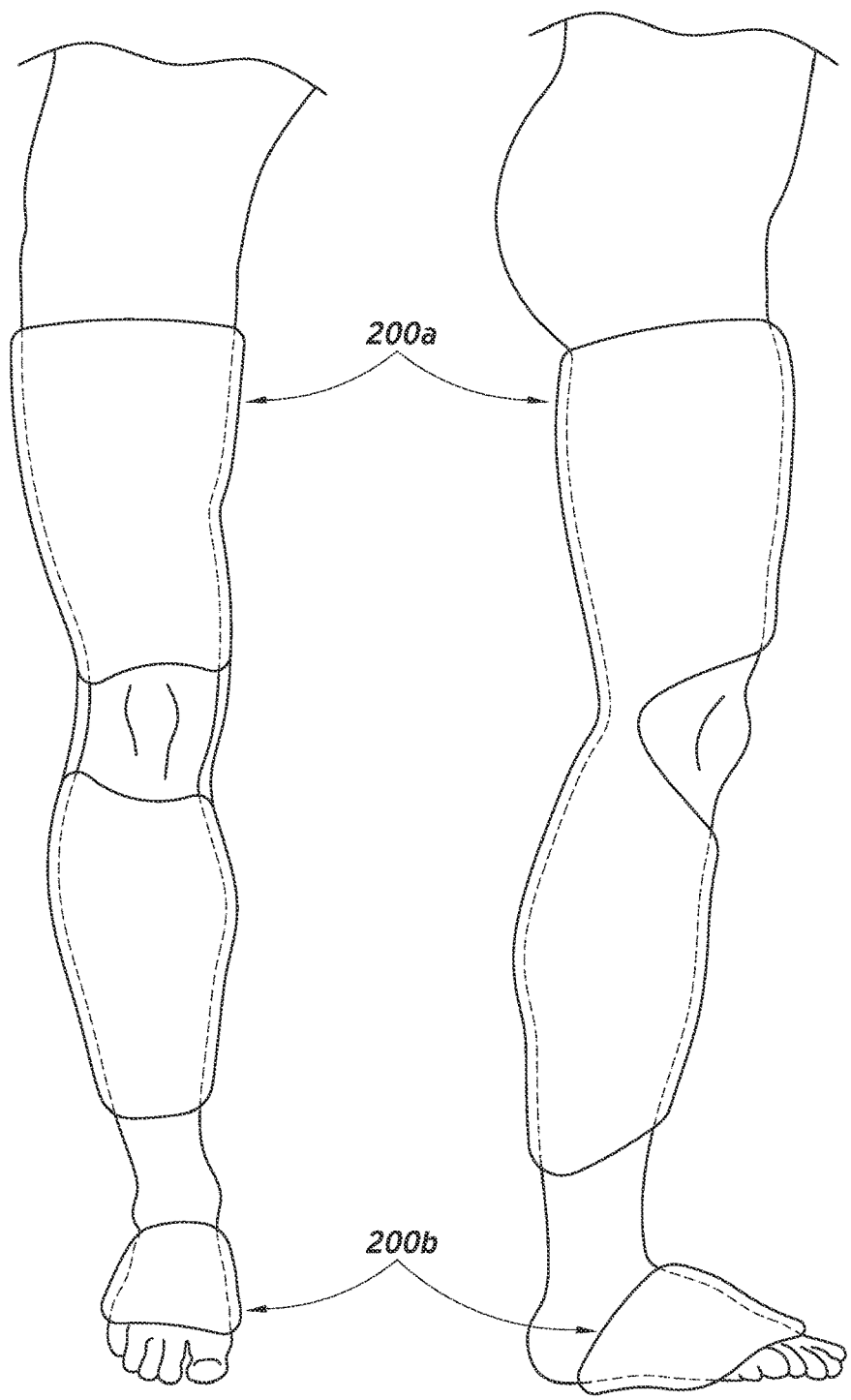
FIG. 2 provides front and side views of a non-continuous sleeve configured to provide blood flow and/or compression therapy to a patient.

FIG. 2 provides front and side views of a non-continuous sleeve configured to provide blood flow and/or compression therapy to a patient. The non-continuous sleeve may comprise at least two separate portions, which may include an upper portion 200a (e.g., configured to apply therapy to the patient's, thigh, popliteal fossa, and/or calf) and/or a lower portion 200b (e.g., configured to apply therapy to the sole of the patient's foot). In some embodiments, warming and/or compression therapy may be provided to a limb using either, but not both, of an upper portion and a lower portion, wherein such sleeve portion is configured to provide warming and/or compression functionality in accordance with aspects of the present disclosure.

Figure 3A:
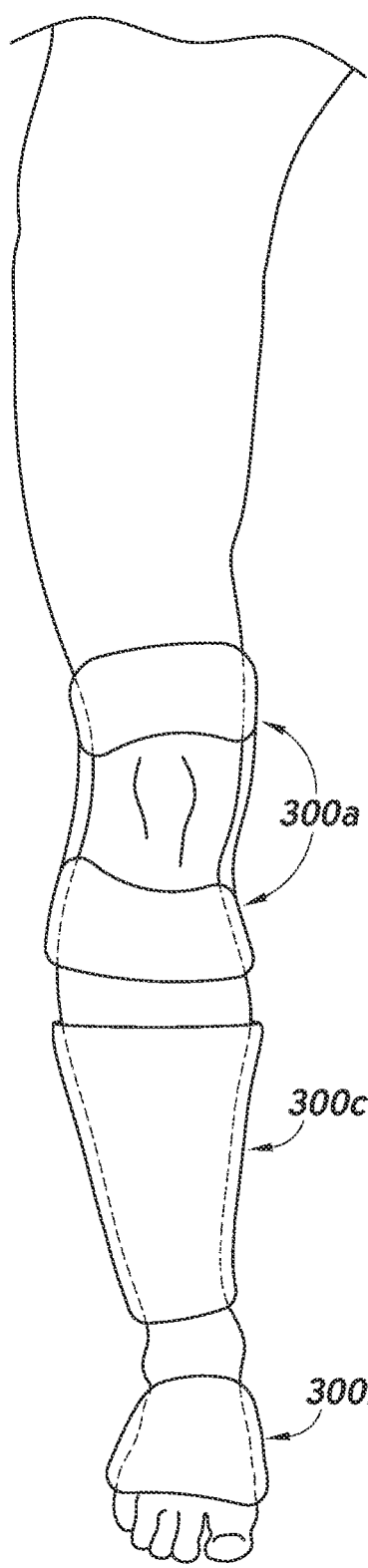
FIGS. 3A and 3B provide front views of a non-continuous sleeve configured to provide blood flow and/or compression therapy to a patient.
Figure 3B:
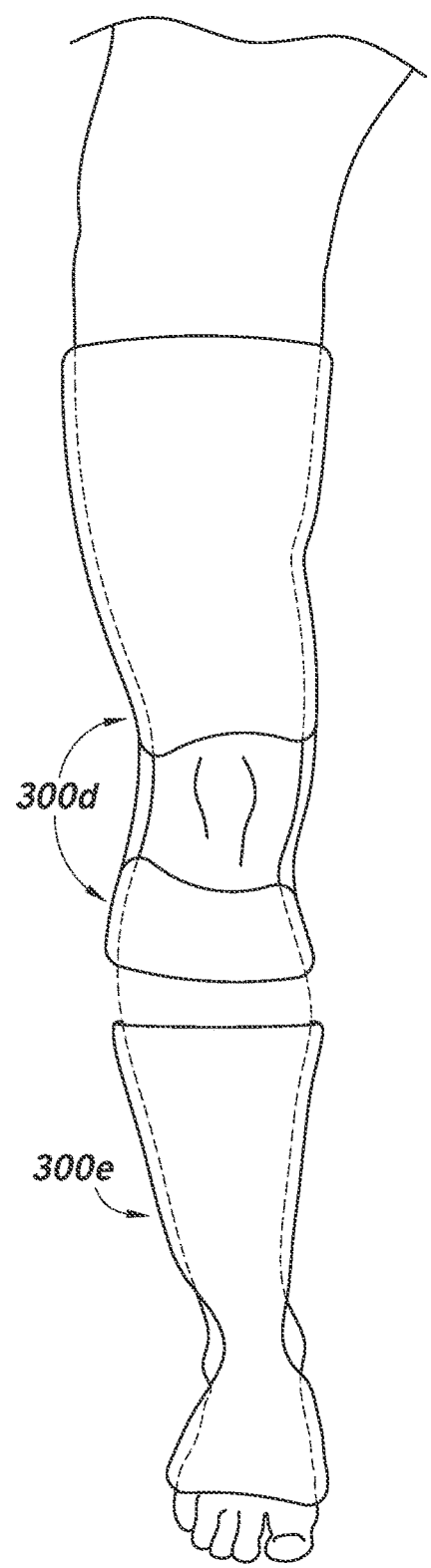

FIGS. 3A and 3B provide front views of non-continuous temperature management sleeves configured to provide blood flow and/or compression therapy to a patient. In the embodiment shown in FIG. 3A, a first portion 300a and/or a second portion 300b of the sleeve may be configured to deliver heat to an anatomical area over and/or comprising the popliteal artery and/or an anatomical area over and/or comprising the medial and/or lateral plantar arteries, while a third portion 300c of the sleeve may be configured to deliver blood flow therapy through intermittent compression to an area between the first portion 300a and the second portion 300b. In some embodiments, the second portion 300b and third portion 300c may be combined into a single continuous portion (300d in FIG. 3B). For example, in the embodiment shown in FIG. 3B, heat and/or blood flow therapy may be applied by the second portion 300e to at least some portions of the patient's foot and/or calf area. That is, rather than separate sleeve portions for each of the lower leg and the foot, a single sleeve portion/form may cover the lower leg and foot and provide warming and/or compression therapy thereto. In some embodiments, warming and/or compression therapy may be provided to a limb using any single one, or combination, of an upper portion, lower leg portion, and/or foot portion, wherein each of such sleeve portion(s) is/are configured to provide warming and/or compression functionality in accordance with aspects of the present disclosure.

With further reference to FIG. 3A, in some embodiments, the first portion 300a, second portion 300b, and/or third portion 300c may be configured to provide heat and/or compression. In some embodiments, (e.g., in the example shown in FIG. 3B), the upper portion 300d may be configured to extend along a patient's thigh to provide heat and/or compression to the patient's thigh. The upper portion 300a/300d may be configured to apply heat to at least a popliteal fossa portion of (e.g., behind) the patient's knee area.

Forced gas and/or fluid delivered through the knee/upper leg portion 300a/300d, calf portion 300c/300e, and/or foot portion 300b/300e may be configured to apply compression to one or more areas of the patient's body. In some embodiments, forced gas and/or fluid moving through one or more portions for compression may be heated to also or alternatively provide heating. However, in some embodiments, one or more portions of the sleeve may comprise separate channels for compression gas and/or fluid and heated gas and/or fluid.

In some embodiments, heating may only be applied to certain areas of the patient's limb (e.g., at the popliteal fossa of the knee but not at the kneecap). However, heating may alternatively be applied across the entire sleeve or portions of sleeve. In some embodiments, forced gas and/or fluid passing through one or more portions of the sleeve(s) may be configured to circulate within the sleeve and/or to exit the sleeve. The sleeve(s) may comprise one or more perforations to allow gas and/or fluid to exit the sleeve.

Portions of the sleeve(s) may be composed of or comprise one or more of a variety of fabrics and/or materials. In some embodiments, one or more portions of the sleeve(s) configured to interface with the patient's skin may be at least partially composed of hydrogel, mesh, and/or other materials. The sleeve(s) may be at least partially composed of a breathable material. For example, an inner layer or layers of the sleeve(s) may comprise at least partially breathable/porous material to facilitate the egress of warm gas and/or fluid in the direction of the patient's skin. In some embodiments, the sleeve(s) may comprise one or more flexible sheets and/or circuits. For example, such sheets/circuits may have certain conductive traces printed/disposed thereon, wherein such traces may have electrical current passed therethrough to generate resistive heating for temperature management according to aspects of the present disclosure. The sleeve(s) may be sized and/or positioned to minimize overall space covering the patient's body while maximizing heat and/or compression therapy applied to the patient's body.

Some embodiments of the present disclosure provide various advantages and/or benefits over alternative temperature management solutions, including cost benefits. For example, some sleeves described herein may require heating at only a knee portion and/or a foot portion of a patient's body to provide core heating to the patient. This may limit the number of required heating elements and/or energy exhausted for heat transfer/generation, thereby providing relatively reduced cost. Moreover, for each area of the patient's body where heating is delivered, the heated area may require monitoring to prevent burning and/or ensure sufficient heating/warming. For example, certain embodiments described herein may comprise one or more temperature sensors at the knee portion and/or foot portion. Thus, by reducing the amount of heated portions of a sleeve device/assembly and/or the patient's anatomy, the amount of monitoring necessary to sufficiently evaluate the risk of overheating/burning may be reduced as well. Moreover, heating and/or monitoring may be less precise as the surface heating area increases. For example, devices may comprise an inlet for heated gas and/or fluid to enter the sleeve; the temperature at and/or near the inlet may be higher than at other portions of the sleeve and/or at an outlet of the sleeve. The larger the area covered by one or more heating bladders/elements of the sleeve, the lower the uniformity of the temperature throughout the one or more heating bladders/elements. Thus, heating and/or monitoring precision may be improved as a result of the reduced heating area of the described embodiments.

Figure 4:
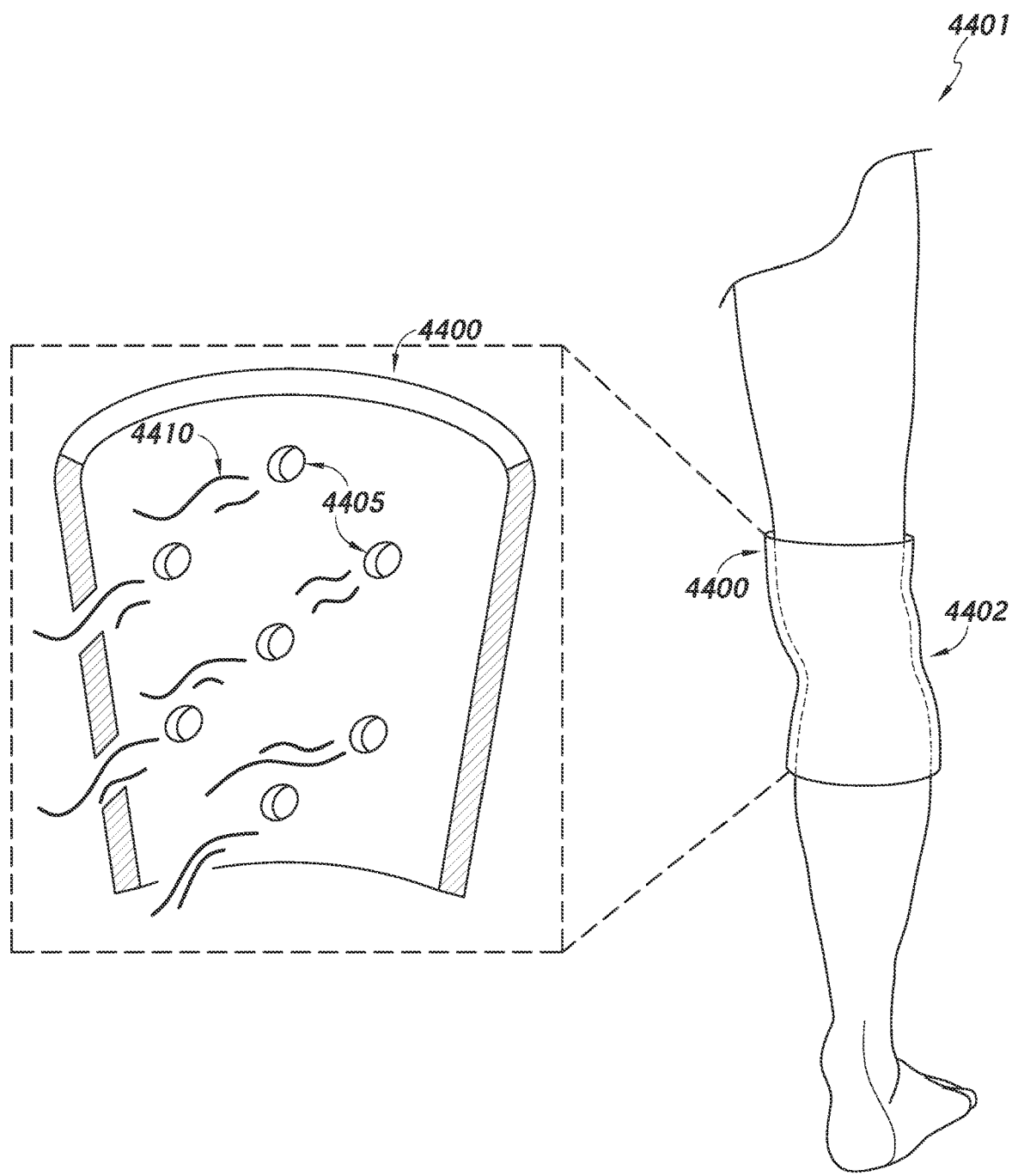
FIG. 4 provides a close-up view of at least a portion of a sleeve for providing heat and/or compression at or near a knee portion of a limb.

FIG. 4 provides a close-up view of at least a portion of a temperature management sleeve device/assembly 4400 for providing heat and/or compression at or near a knee portion 4402 of a leg/limb 4401 of a patient. The sleeve 4400 may be configured to provide warming through convective, conductive, and/or radiative heat transfer to the targeted area(s) of therapy. In some embodiments, the sleeve 4400 is configured to provide compression functionality in addition to heating. The targeted area(s) may include, for example, a popliteal fossa area of the limb. The sleeve 4400 may comprise one or more perforations 4405 at least over an inner surface (e.g., a skin-interfacing surface) of the sleeve 4400. The one or more perforations 4405 may be configured to allow heated gas 4410 to pass out of the sleeve 4400 to in the direction of the patient's skin.

Figure 5:
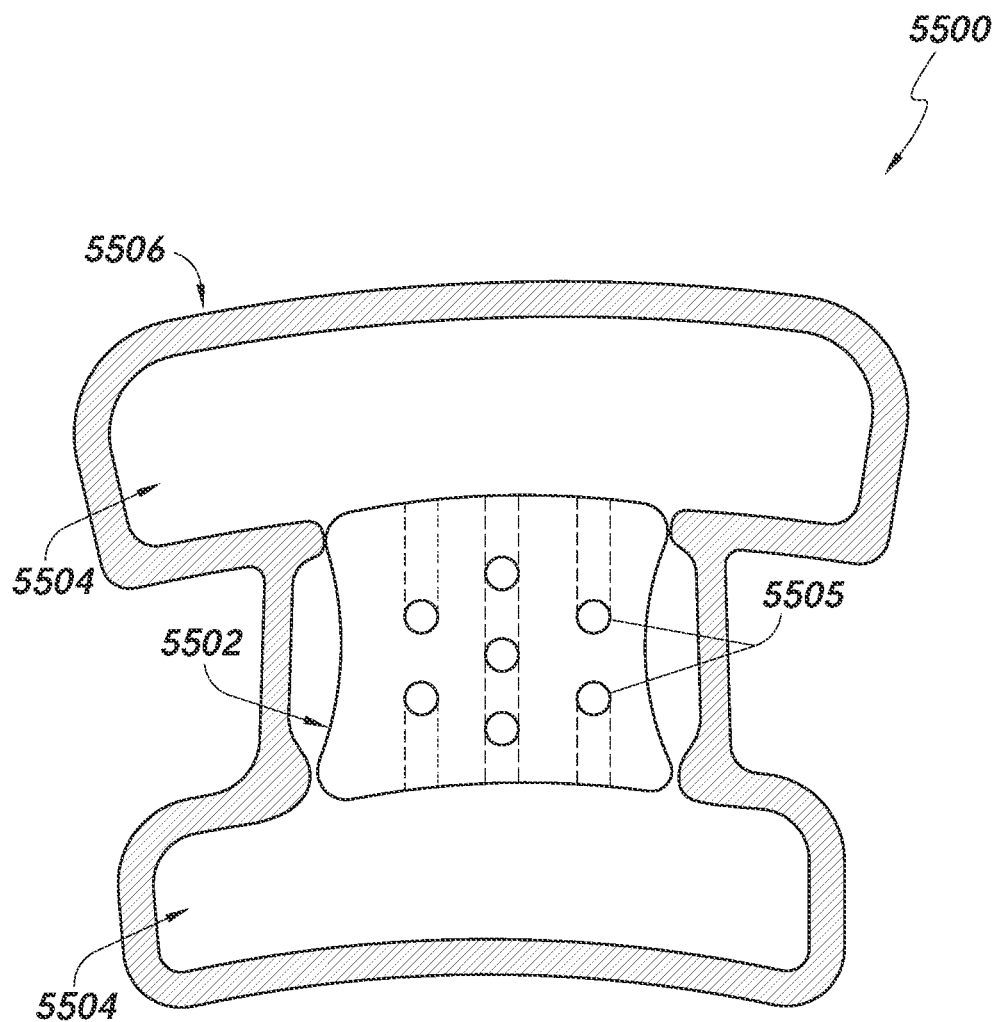
FIG. 5 illustrates at least a portion of a sleeve for providing heat and/or compression to at least one area of a patient's limb.

FIG. 5 illustrates at least a portion of a sleeve 5500 for providing heat and/or compression to at least one area of a patient's limb. The sleeve 5500 may comprise a warming portion/device 5502 configured to hold heated gas and/or fluid. The terms "warming portion," "warming element," "warming bladder," "heating/heated bladder," "heating portion," and "heating element" are used herein to refer to any portion, device, and/or element of a sleeve configured to transfer/deliver heat to an area of a human body. The terms "warming" and "heating" are used herein in accordance with their broad and ordinary meanings and are used substantially interchangeably in some contexts herein. Heat may be delivered by the warming portion 5502 convectively, conductively, and/or in any other suitable manner. In some embodiments, the sleeve 5500 may further comprise one or more perforations 5505 to allow heated gas and/or fluid to exit the sleeve and/or contact skin of the patient.

The sleeve 5500 may further comprise one or more compression portions 5504 configured to inflate with gas and/or fluid and/or to press against the patient's skin and/or compress the patient's limb. The terms "compression portion," "compression element," "bladder," "compression bladder," and "blood flow element" are used herein to refer to any portion and/or element of a sleeve configured to deliver compression to an area of a human body. The one or more compression portions 5504 may be configured to inflate sequentially with, for example, warmed (or non-warmed) fluid to compress the limb and/or provide warming to the patient. In some embodiments, gas and/or fluid used to fill the warming portion 5502 may also be used to fill the compression portions 5504. However, the gas and/or fluid in the warming portion 5502 may be separate and/or independent from any gas and/or fluid in the compression portions 5504.

In some embodiments, the warming portion 5502 and/or fluid channels within the warming portion 5502 may have any of a variety of shapes, sizes, configurations, alignments, orientations, and the like. For example, the warming portion 5502 and/or a fluid channel configured to carry heated fluid and/or gas within the warming portion 5502 may have an at least partially coiled and/or spiraling structure. The partially coiled and/or spiraling structure may comprise one or more elements configured to allow bending, stretching, deformation, and/or other adjustments to the warming portion 5502 to conform the warming portion 5502 to a patient's limb surface. In some embodiments, the channel(s) may be configured to double-back one or more times in one or more generally straight vertical and/or horizontal paths.

The warming portion 5502 and/or compression portion 5504 may be configured to provide warming through conductive/radiative heat transfer to various targeted areas of therapy. In some embodiments, compression may be maintained during warming of the targeted area(s). Fluid and/or gas inflating and/or deflating the compression portions 5504 within the sleeve 5500 limy be heated to provide warming to the limb. For example, the sleeve 5500 may be configured to provide heating across the warming portion 5502 and the compression portion(s) 5504 while only the compression portions 5504 may be configured to provide compression. In some embodiments, the sleeve 5500 may comprise an adhesion portion 5506 configured to attach and/or hold the sleeve 5500 to the patient's limb (e.g., skin thereof). The adhesion portion 5506 may comprise an outer portion of the sleeve 5500 and/or may comprise and/or may be coated with any of a variety of adhesive materials.

Figure 6A:
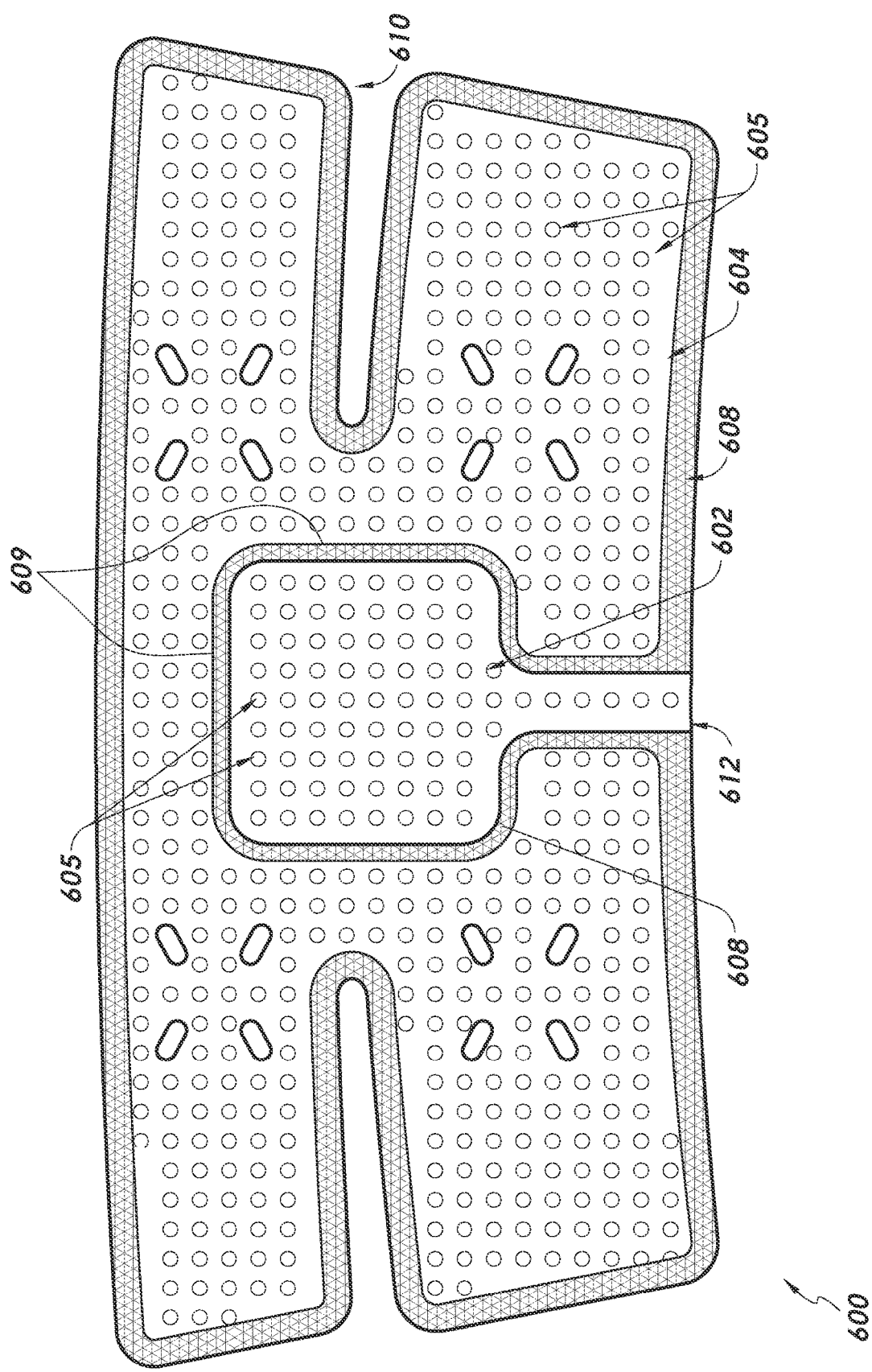
FIG. 6A illustrates an inner surface of at least a portion of a sleeve in accordance with some embodiments.

FIG. 6A illustrates an inner surface of at least a portion of a sleeve 600 in accordance with some embodiments of the present disclosure. The inner surface may comprise a warming portion 602 and/or a non-warming portion 604 (e.g., a compression portion). The warming portion 602 and/or non-warming portion 604 may be configured to contact and/or otherwise interface with a patient's skin. In some embodiments, the warming portion 602 and/or the non-warming portion 604 may comprise one or more perforations 605 configured to allow heated gas and/or fluid contained within, for example, the warming portion 602 (e.g., one or more fluid channels thereof) to pass out of the sleeve and into contact with the patient's skin. The non-warming portion 604 may not be configured to provide, heat to the patient and/or may be configured to provide compression to the patient through tightening and securing of the strap portions 610 to one another. In some embodiments, one or both sides of the straps 610 include adhesive, Velcro, and/or other fastening features for fastening the straps over and/or around a limb of the patient.

In some embodiments, the warming portion 602 may be configured to provide heat to the patient via conductive, radiative, and/or convective heat transfer. For example, one or more wires, traces, and/or other conductive heating elements may be disposed within the warming portion 602, wherein such heating elements may be electrically powered using one or more wires electrically coupled thereto through an opening/channel 612 associated with the warming portion 602. When activated (e.g., when electrical current is passed therethrough), the conductive heating elements may beat-up, wherein such heat may radiate in the direction of the patient's skin and/or heat the material in contact/proximity with the patient's skin to thereby warm the patient's skin and surrounding tissue (e.g., at or near the popliteal fossa). In some embodiments, warmed gas and/or fluid may be passed through the warming portion 602 and out of the warming portion through perforations 605 therein to warm the patient's body (e.g., at or near the popliteal fossa). The warming portion 602 and/or non-warming portion 604 may comprise heating and/or compression bladders and/or foam or similar materials configured to contact the patient's skin.

The sleeve 600 may comprise closed-off borders 608 configured to surround the warming portion 602 and/or the non-warming portion 604. In some embodiments, the thickness of the sleeve at the borders 608 may be less than a thickness of the sleeve 600 at more central portions of the warming portion 602 and/or the non-warming portion 604. For example, the borders 608 may not comprise bladders and/or foam or similar materials. In some embodiments, the borders 608 do not generally contact the skin of the patient, at least with respect to certain portions of the borders 608, such as portions 609 that physically and/or fluidly isolate the warming portion 602 from the non-warming portion(s) 604. The borders 608 may represent gaps in the bladder(s) and/or foam or similar materials of the warming portion 602 and/or non-warming portion such that the borders 608 may allow the sleeve 600 to more easily be bent and/or otherwise shaped to fit a patient. The patterns of the borders 608 illustrated in FIGS. 6A and 6B are exemplary and other patterns of borders 608 and/or sizes and/or shapes of the warming portion 602 and/or non-warming portion 604 may be utilized.

The sleeve 600 may comprise one or more straps 610 configured to be wrapped around an area of the patient's limb. For example, the straps 610 may be configured to wrap around areas above and below the patient's knee, respectively, to allow the sleeve 600 to be secured such that the warming portion 602 is positioned at or near the popliteal fossa region of the patient's limb.

Figure 6B:
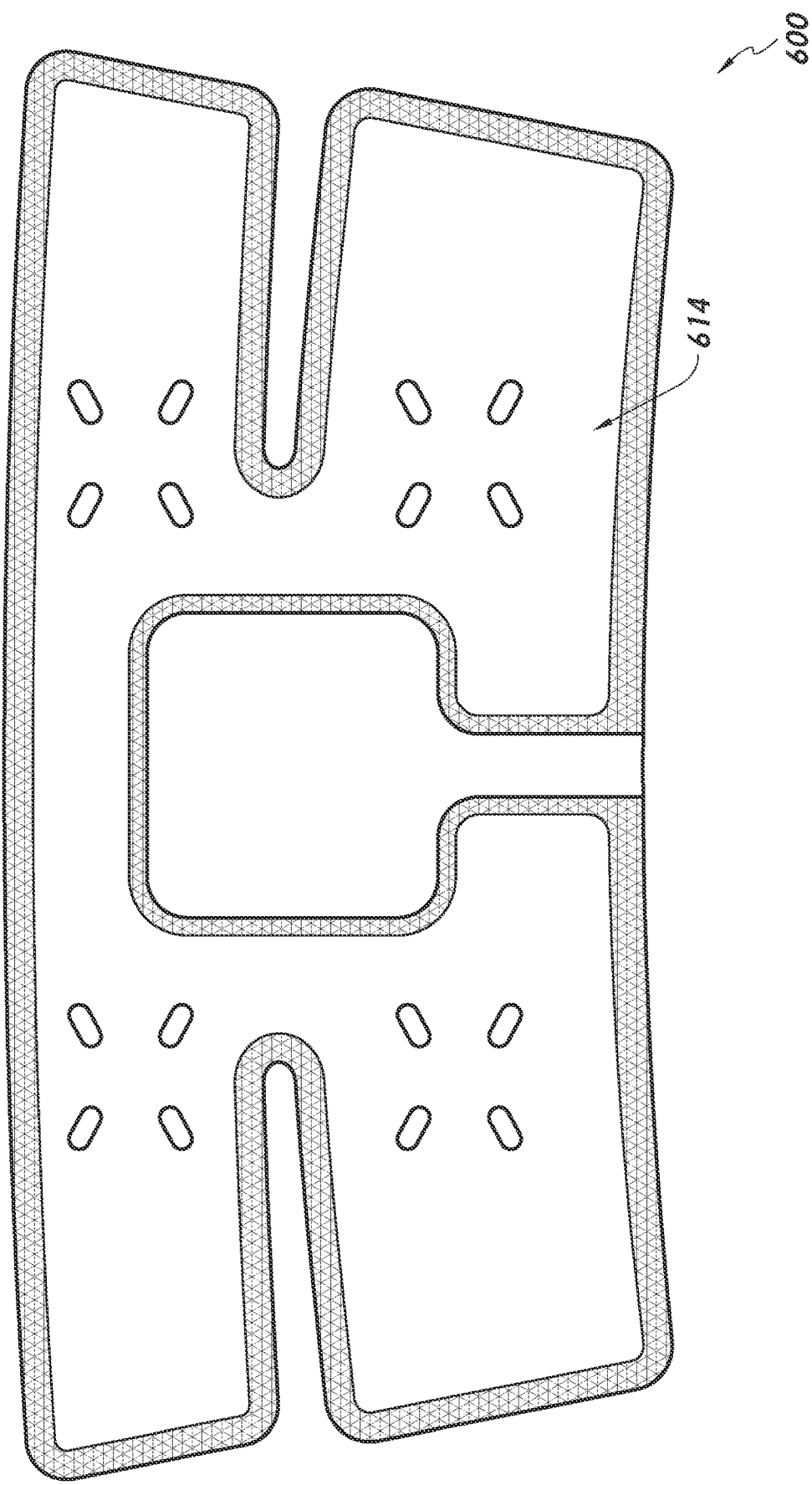
FIG. 6B illustrates an outer surface of at least a portion of a sleeve 600 in accordance with some embodiments.

FIG. 6B illustrates an outer surface 614 of at least a portion of a sleeve 600 in accordance with some embodiments. For example, the side of the sleeve 600 shown in FIG. 6B may generally be outward-facing when the sleeve is secured on the patient's limb. The outer surface 614 may comprise any of a variety of materials and/or may be configured to prevent heat from escaping. For example, one or more outer layers of the sleeve 600 may be disposed between any heating elements and/or compression and/or heating air chambers of the sleeve and the outside of the sleeve, wherein such layer(s) is/are fluid-tight. It should be understood that references herein to heat transfer through the use of gas as a heat transfer medium, or compression through the use of gas-filled bladders/chambers, any type of fluid may be used instead of, or in addition to, gas (e.g., air), including any suitable or desirable type of gas or liquid (e.g., water, such as heated water, or other liquid solution).

Figure 7:
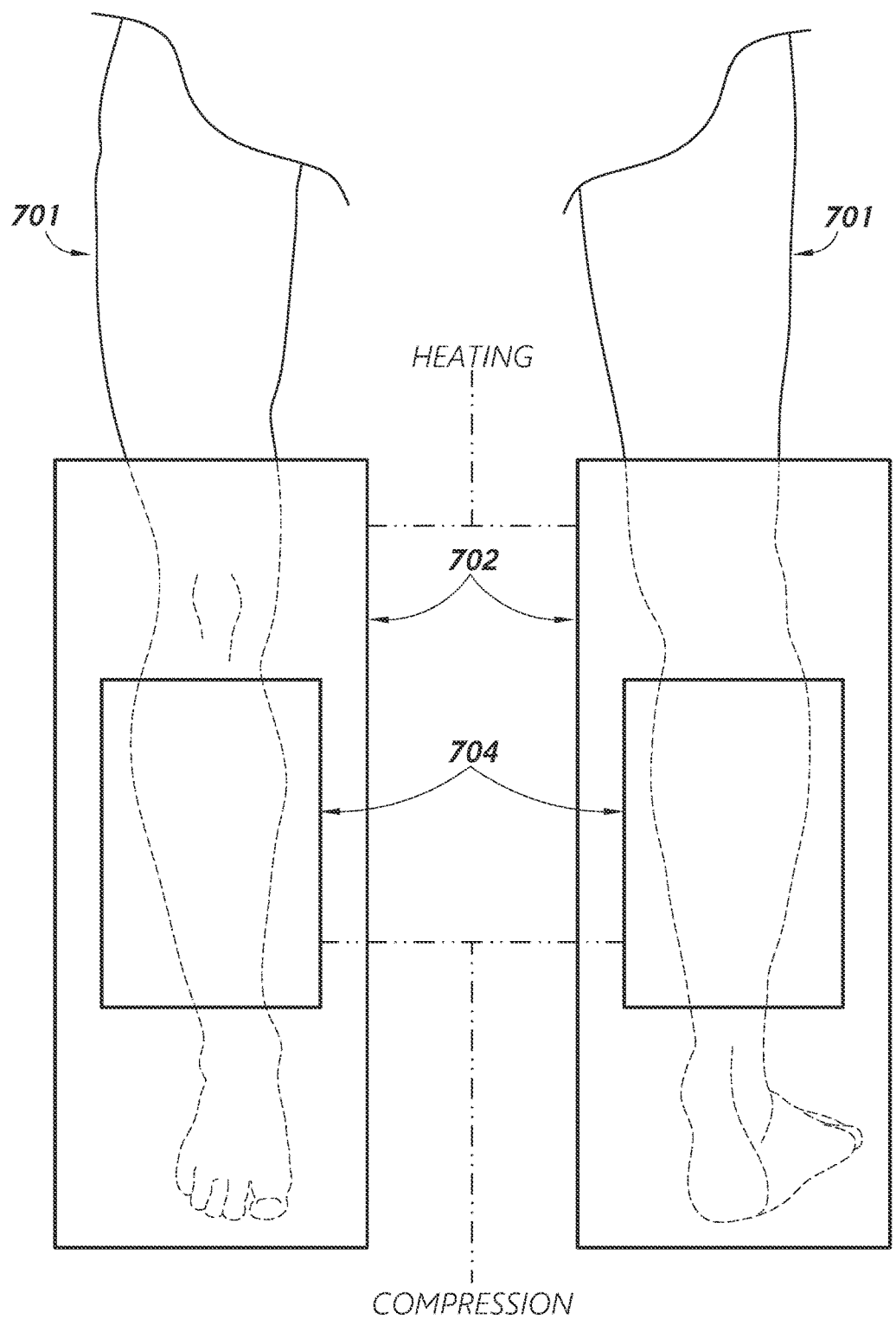
FIG. 7 provides a diagram illustrating heating and compression areas in accordance with one or more embodiments.

FIG. 7 provides a diagram illustrating general heating and compression areas of one or more sleeves described herein. In some embodiments, both heating therapy and blood flow (i.e., compression) therapy may be applied to the same areas of a patient's body. For example, as shown in FIG. 7, heating may be applied to a first area 702 covering a substantial portion of a patient's limb 701, including at least the knee and/or foot areas, while compression may be applied to a second area 704. For example, the first area 702 may include areas covering at least portions of the patient's foot, calf, knee (e.g., the popliteal fossa and/or knee cap), and/or thigh, while the second area 704 may include the calf.

Figure 8:
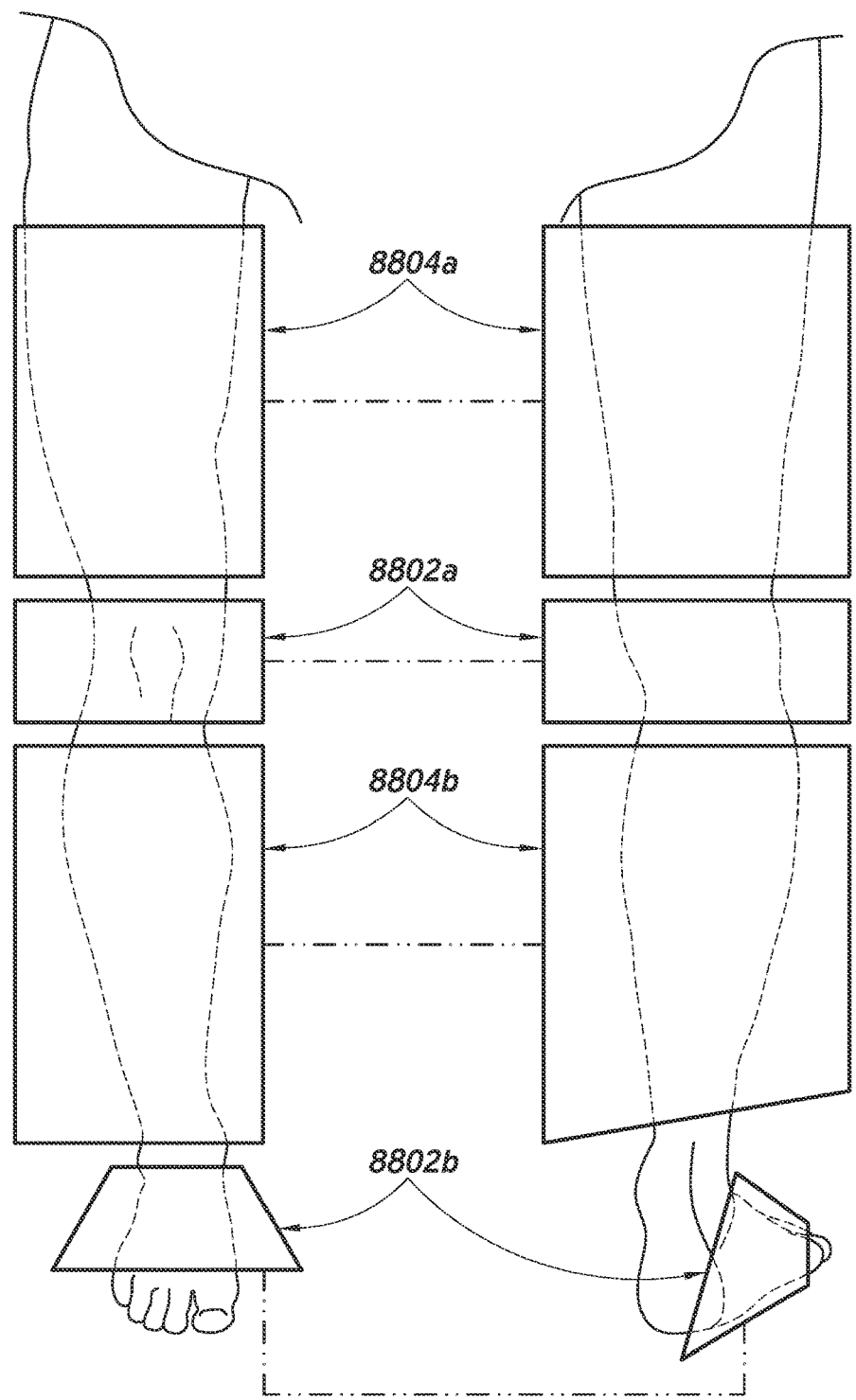
FIG. 8 provides another diagram illustrating heating and compression areas in accordance with one or more embodiments.

FIG. 8 provides another diagram illustrating heating and compression areas that may be associated with any of the embodiments of sleeves described herein. As shown in FIG. 8, in some embodiments, sleeves may deliver heat or compression to different areas of the patient's body. For example, heating may be provided to a first area 8802a (e.g., at or around the patient's knee) and/or a second area 8802b (e.g., a foot, such as at or around a sole of the patient's foot), while compression may be provided to a third area 8804a (e.g., at or around the patient's thigh) and/or a fourth area 8804b (e.g., at or around the patient's calf).

The inflation and/or deflation sequence of warming portions of sleeves in accordance with aspects of the present disclosure may be different from compression portions. For example, the warming portions (e.g., warming bladders, channels, and/or areas/compartments) may be configured to not completely deflate such that the warming portions maintain consistent skin contact. Moreover, the warming portions may be configured to maintain a lower maximum pressure compared to compression portions to avoid blood flow restriction. The warming portions may be configured to inflate and deflate at more rapid cycles than the compression portions to maintain a desired temperature profile at the desired heating location. In some embodiments, fluid providing compression and fluid providing warming may be separate fluids, may travel in distinct channels, and/or may remain isolated from each other within a sleeve.

Warming and Compression Elements/Mechanisms

Figure 9:
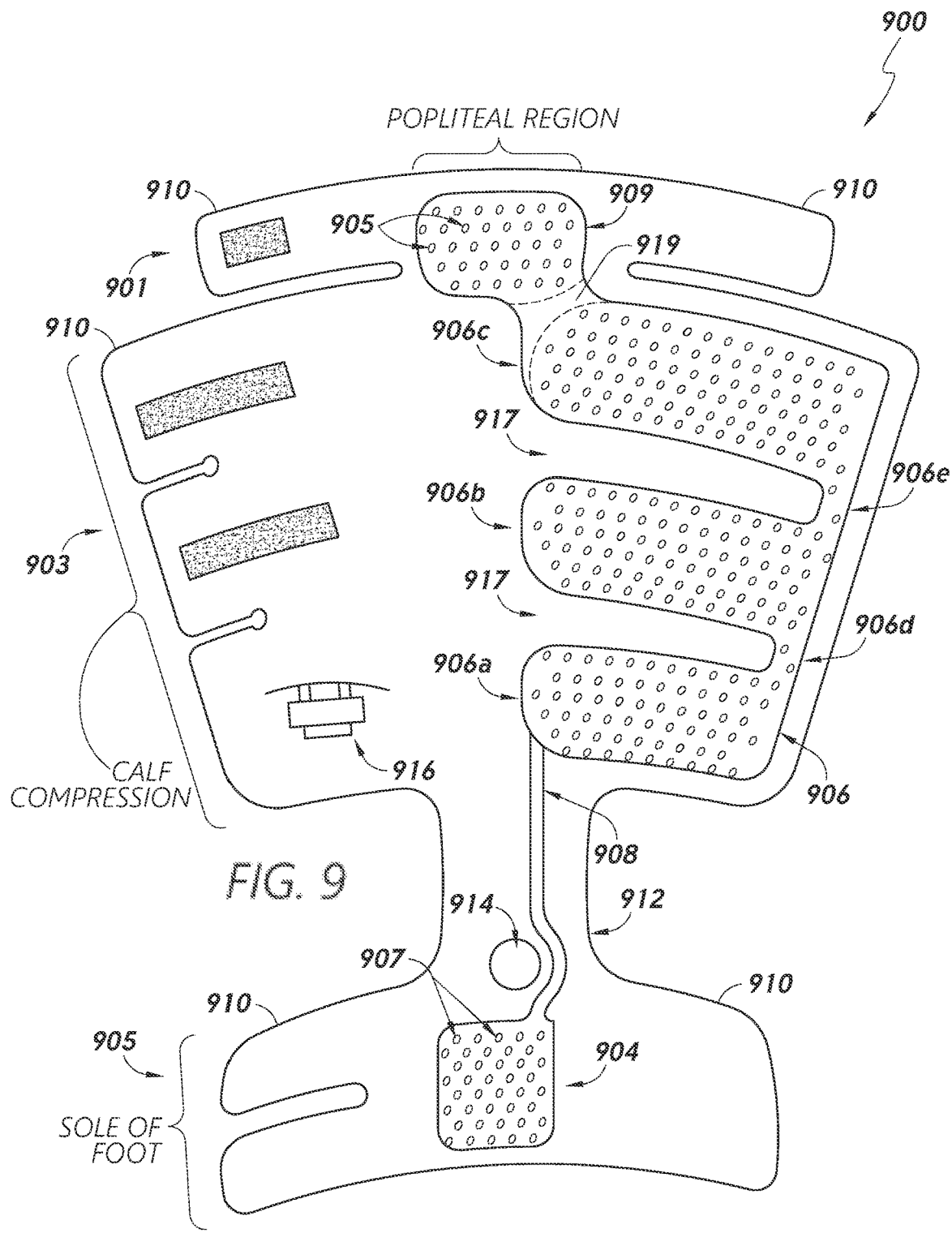
FIG. 9 provides a view of a sleeve configured to provide heating and/or compression via a first portion configured to contact a calf of a patient and a second portion configured to contact a sole of a foot of the patient in accordance with one or more embodiments.

FIG. 9 provides a view of a sleeve 900 configured to provide heating and/or compression via a first portion 901 configured to contact the back of a knee of a patient, a second portion 903 configured to contact a calf of a patient, and/or a third portion 905 configured to contact a foot of the patient. In some embodiments, the sleeve 900 may be configured to provide heat therapy using convective and/or other heating methods. The sleeve 900 may comprise one or more heating and/or compression bladders 906 which may be connected (e.g., in fluid communication) and/or may be separated (e.g., fluidly isolated) from each other. In some embodiments, one or more channels 908 may be configured to provide transport of fluid (e.g., gas) to one or more bladders 906, 904, 909 for delivering heating and/or compression. The one or more bladders 906 may comprise one or more perforations 905 positioned and configured to pass heated gas/fluid to targeted areas of the patient's body (e.g., the popliteal region and/or the sole of the foot). Although referenced using separate reference numbers, in some embodiments, two or more of the bladders 904, 906, 909 are in fluid communication with one another.

The sleeve 900 may comprise multiple portions configured to contact and/or provide heat and/or blood flow therapy to one or more areas of a patient's limb. For example, the sleeve 900 may comprise a first portion 901 configured to provide heat and/or compression to a patient's knee (e.g., at the popliteal fossa) and/or thigh, a second portion 903 configured to provide heat and/or compression to a patient's calf and/or surrounding areas, and/or a third portion 905 configured to provide heat and/or compression to a patient's foot (e.g., the sole of the foot) and/or the surrounding areas.

In some embodiments, channels 908 and/or bladders 906 for providing blood flow and/or compression therapy may not have perforations in at least one or more portions thereof. Bladders 906 for compression may utilize flowing gas for sequential compression. Bladders (e.g., 904 and/or 909) configured to provide heating may have perforations 907 and/or may be configured to provide a relatively continuous stream of heated gas/fluid for compression and/or heating therapy. In some embodiments, skin/tissue contact may be achieved without compression bladders 906. For example, one or more inserts (e.g., foam insert(s)) may be disposed in or on the sleeve 900 to press the bladders 906 and/or the perforations 905 against the patient's skin to establish and/or maintain surface contact between the sleeve 900 and the patient's skin at least in certain desired areas. The number and/or size of the perforations 905 can affect compression. For example, gas may escape more easily with a greater number and/or size of the perforations 905, thereby affecting the pressure within the sleeve 900.

With respect to the compression bladders 906, in some embodiments, some bladders 906 may not start filling until other bladders 906 reach a certain pressure. For example, fluid may be provided to the bladders 906 through the channel 908, initially passing into the lower/first bladder portion 906a. The first bladder portion 906a may be fluidly coupled to the second/intermediate bladder portion 906b via an interconnection channel 906d. In some embodiments, fluid may not propagate through the channel 906d into the second bladder portion 906b in substantial amounts until the fluid in the first bladder portion 906a reaches a certain pressure level due to the filling of the first bladder portion 906a. That is, the fluid entering the bladder 906a may sequentially fill the first bladder portion 906, then the second bladder portion 906b, and then the upper/third bladder portion 906c (via the interconnecting channel 906e). Although a certain amount of fluid may pass into the second 906b and third 906c bladder portions prior to the first bladder portion 906a reaching a maximum or threshold volume and/or pressure, the degree to which the first bladder portion 906a fills with fluid may be greater initially compared to the other bladder portion(s). Likewise, the second bladder portion 906b may fill to a greater degree and/or more quickly than the third bladder portion 906c prior to the second bladder portion 906b reaching a maximum or threshold volume and/or pressure. The heat-transfer fluid may further pass to the popliteal bladder portion 909. In some embodiments, the popliteal bladder or other type of heating element may be isolated from the bladder portions 906, such as by a break or barrier portion 919. The interconnection channels 906d, 906e may be sized/dimensioned to produce/control desired sequence/timing of sequential filling of the respective bladder portions 906.

In other embodiments, the first bladder portion 906a, second bladder portion 906b, and/or third bladder portion 906c may be independent of other bladder portions 906. For example, the first bladder portion 906a may not be connected to the second bladder portion 906b by a first interconnection channel 906d and/or the second bladder portion 906b may not be connected to the third bladder portion 906c by a second interconnection channel 906e. Moreover, in some embodiments, one or more bladders 906 may be pressure-controlled independently by an individual fluid channel 908. For example, the sleeve 900 may comprise multiple fluid channels 908 in which at least one of the multiple fluid channels 908 may provide pressure control to only one of the bladders 906.

In some embodiments, one or more bladders 906 may have various features to enable easier wrapping of the sleeve 900 around the patient's limb. For example, a bladder 906 may comprise dimples and/or other features. Furthermore, the bladders 906 may be separated by break portions 917.

In some embodiments, one or more channels 908 for delivering heated gas and/or fluid may not have perforations 905 and/or may act as bladders that may be configured to inflate/deflate with a single port. Gas can be cycled in and out of a heated bladder on a higher frequency than compression bladders 906. For example, if compression bladders 906 are cycled 1-2-3, heated bladders (e.g., 909, 904) may be cycled with each compression cycle 1-1-1. A cycle may have a duration of approximately sixty seconds but may be adjusted depending on an amount of heat dissipation. In some embodiments, the sleeve may comprise a single bladder 906 utilizing intermittent compression.

Compression may be controlled such that whenever heating is active, compression at target heating areas may be maintained. For example, compression at or near the popliteal fossa and/or the foot may be maintained during heating cycles to ensure that the generated heat is transferred to the popliteal fossa and/or foot. Compression bladders 906 may be filled with additional gas/fluid when pressure at the compression bladders 906 is detected below a threshold pressure value. In some embodiments, a foam pad may be utilized to establish and/or maintain surface contact between the heating bladders and the target areas.

Heating may be delivered via a sheet-type heating element/device, which may utilize either a convective or conductive configuration. Compression bladders 906 may be separate from the heating sheet. In some embodiments, the compression bladders 906 may be configured to maintain an ON state in which the compression bladders 906 continuously press inward in the direction of the skin of the patient. In some embodiments, one or more foam pads may be utilized in place of one or more compression bladders 906.

In some embodiments, heating may be delivered at least in part by fluid escaping and/or passing through perforations 905 of the sleeve 900, which may or may not be associated with the compression bladder portions 906 in addition to the heating portions 904, 909. In some embodiments, the sleeve 900 may comprise one or more straps 910 configured to be wrapped at least partially around a knee and/or other portion of a patient's limb. The arms 910 may be adjustable to allow for wrapping around patients of different sizes. For example, the straps 910 may include Velcro or other types of fastening features for fastening the straps 910 to one another around the patient's limb. Moreover, the length of the sleeve 900 may be adjusted (e.g., at a neck portion 912 between the second portion 903 and the third portion 905) by extending and/or tightening portions of the sleeve 900 and/or by folding and/or securing portions of the sleeve 900 onto and/or to other portions of the sleeve 900.

In some embodiments, the second portion 903 may be configured to provide heating and/or compression to the calf of the patient. A single supply or multiple supplies of heated or nonheated fluid may be used to provide heating to the various bladder portions 906 of the sleeve 900.

The sleeve 900 may comprise one or more features configured to enable easier application of the sleeve 900 to patients. For example, the sleeve 900 may comprise a heel locator 914 configured to be positioned at/over the patient's heel. The heel locator 914 may comprise an opening/cavity and/or visual marker in the sleeve 900. In some embodiments, the sleeve 900 may comprise an inlet and/or outlet port 916 configured to receive fluid, gas, and/or electricity from an external source (e.g., a controller) and/or have fluid drawn therefrom. As shown, the port 916 may be accessible outside of the sleeve to allow for engagement therewith using a corresponding connector associated with a fluid and/or electrical supply device.

Like other embodiments of devices described herein, the sleeve 900 may provide various advantages compared to certain alternative temperature management solutions, including ease of application and/or positioning of the devices on patients. Such devices may include various features (e.g., visual and/or physical indicators) for helping users avoid mistakes in application.

Figure 10:
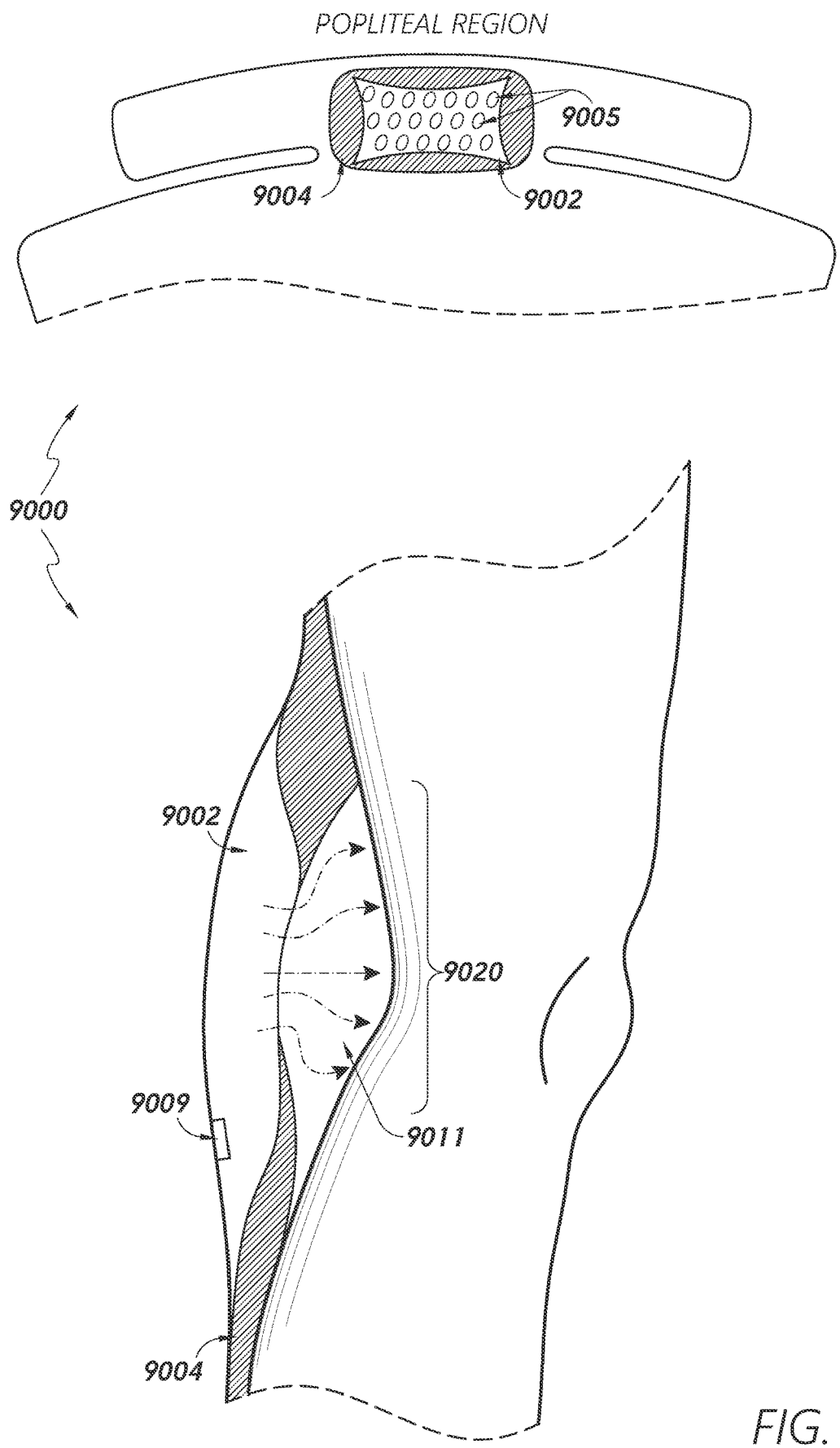
FIG. 10 provides multiple views of at least portions of a sleeve configured to provide heating and/or compression to areas of a patient's limb in accordance with one or more embodiments.

FIG. 10 provides multiple views of at least portions of a sleeve 9000 configured to provide heating and/or compression to areas of a patient's limb. The sleeve 9000 may comprise a warming portion 9002 configured to provide heat transfer to a target area of skin. The warming portion 9002 may comprise one or more perforations 9005 configured to allow heated gas to escape from the warming portion 9002 and contact/warm a patient's skin.

One or more supporting portions 9004 may be positioned adjacent to, near, and/or surrounding the warming portion 9002, as shown in FIG. 90. The supporting portions 9004 may be configured to be inflated with gas/fluid to provide contact with the patient's skin (e.g., at the tissue surrounding the popliteal fossa) and/or to form an unoccluded region 9011 (i.e., cavity or empty space) between the warming portion 9002 and the patient's skin (e.g., at the popliteal fossa 9020). In this way, the unoccluded region 9011 between the warming portion 9002 and the patient's skin may be filled with heated fluid. In some embodiments, the supporting portions 9004 may be configured to at least partially overlap with the warming portion 9002 to be situated between at least a portion of the warming portion 9002 and at least a portion of the patient's skin. In this way, the supporting portions 9004 may be configured to more effectively create separation between the warming portion 9002 and the patient's skin so that the warming portion 9002 does not burn the patient's skin.

The supporting portions 9004 may comprise inflatable bladders around the warming portions 9002 and/or may be configured to provide an adequate distance of the sleeve 9000 away from the skin so to avoid occlusion of the perforations 9005 of the warming portion 9002. The supporting portions 9004 may be configured to be inflated to a pressure that is sufficient to provide spacing for convective heat transfer without undesirably limiting blood flow. For example, the supporting portions 9004 may be inflated to a pressure that is less than an inflation pressure of a compression portion of the sleeve 9000 (e.g., configured to compress the patient's calf areas; not shown in FIG. 90).

In some embodiments, the warming portion 9002 may comprise at least one temperature sensor 9009. In some embodiments, the sensor 9009 may be configured to be positioned at or near the geometric center of the warming portion 9002 to measure the temperature of the warming portion 9002 and/or the heated skin. As with any of the embodiments disclosed herein, in some embodiments, the sleeve 9000 may comprise two or more temperature sensors (e.g., thermistors), which configured to measure the temperature of both the warming portion 9002 and the heated skin simultaneously. Multiple temperature sensors (e.g., thermistors) may be placed along the edges of the warming portion 9002 to measure the temperature gradient across the warming portion 9002 and respective contacting skin region. In some embodiments, the thermistors may be embedded directly into the warming portion 9002. Temperature sensors may be utilized to help regulate the temperature of the warming portion 9002 below a maximum temperature and/or above a minimum temperature. In some embodiments, the temperature of the warming portion 9002 may be maintained such that the temperature remains within a temperature range and/or oscillates between a maximum and minimum temperature at a predetermined period or frequency.

The supporting portions 9004 may not comprise perforations 9005 as the supporting portions 9004 may not be configured to deliver heat. The warming portions 9002 and/or the supporting portions 9004 may be configured to be filled with heated and/or unheated gas. As the heated gas fills the unoccluded region 9011, the heated gas may hold the unoccluded region 9011 open and/or may maintain separation between the warming portion 9002 and the patient's skin.

Figure 11:
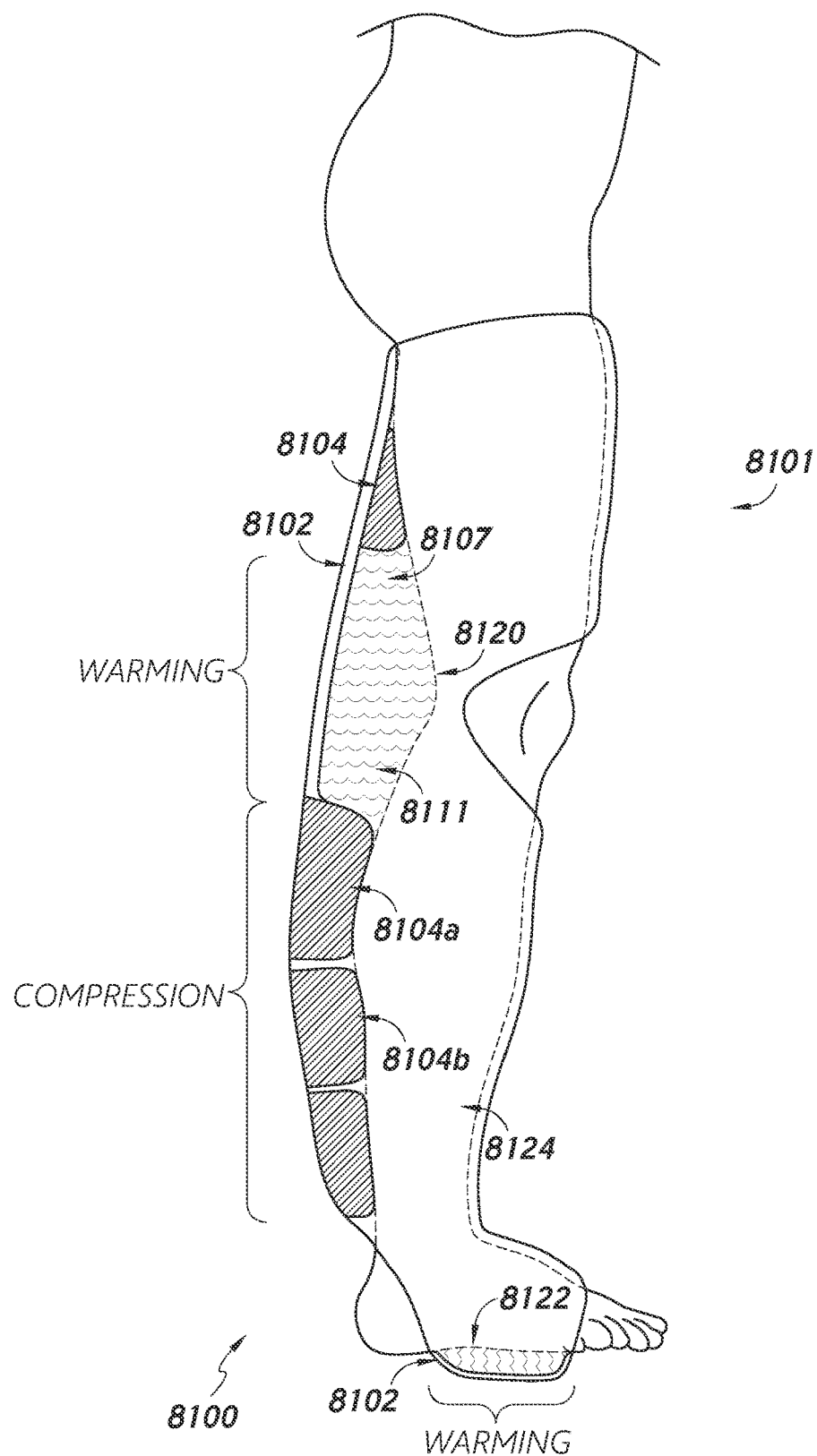
FIG. 11 provides a side view of a sleeve configured to provide heating and compression to a patient's limbs in accordance with one or more embodiments.

FIG. 11 provides a side view of a sleeve 8100 configured to provide heating and compression to a limb of a patient. The sleeve 8100 comprises warming portions 8102 configured to deliver heated gas/fluid 8107 to target areas (e.g., the popliteal fossa 8120 and/or the sole of the foot 8122) of the patient's limb 8101. The sleeve 8100 may further comprise one or more compression portions 8104 configured to create separation between the warming portions 8102 and the patient's skin and/or to provide compression therapy to targeted areas (e.g., the calf area 8124) of the patient's limb. In some embodiments, different compression portions 8104 may be configured to have different pressure levels. For example, a first compression portion 8104a near a warming portion 8102 may be configured to have a lower pressure than a second compression portion 8104b. In this way, the first compression portion 8104a may be configured to effectively create and/or maintain an unoccluded region 8111 between the warming portion 8102 and the patient's skin without substantially restricting blood flow, while the second compression portion 8104b may be configured to provide compression therapy to the targeted areas.

Figure 12:
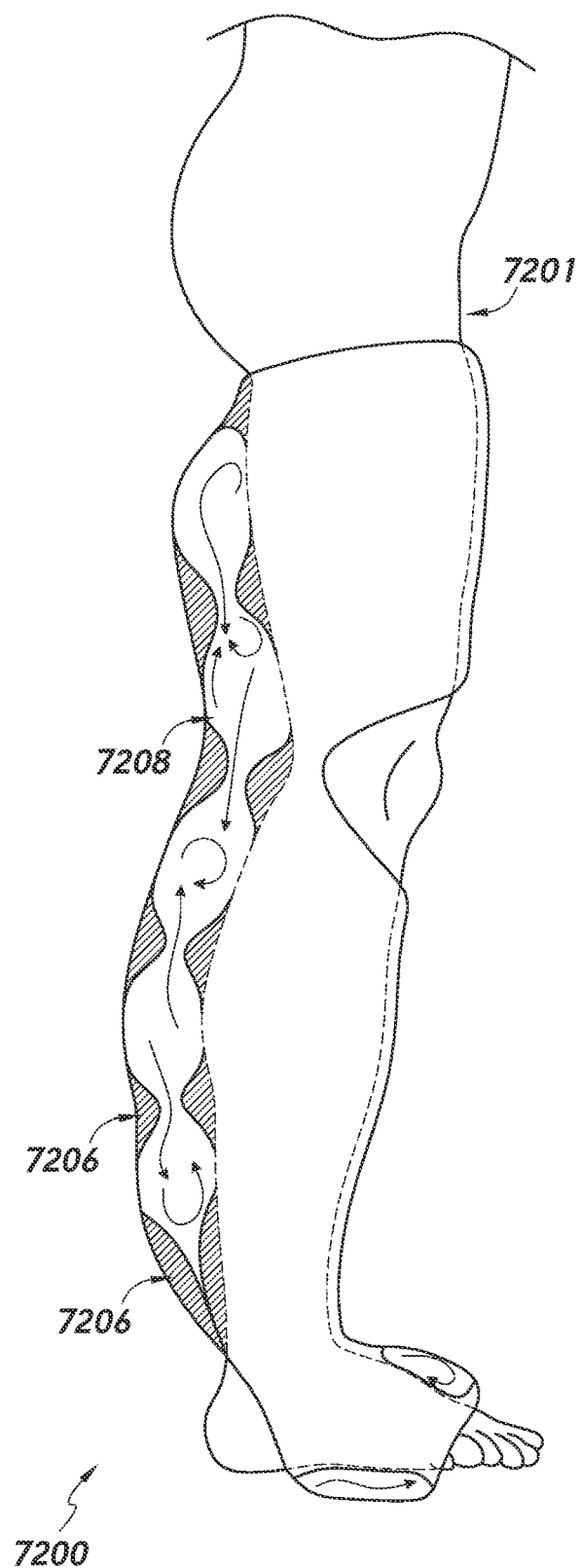
FIG. 12 provides a side view of a sleeve configured to provide convective heating and/or compression to a limb of a patient in accordance with one or more embodiments.

FIG. 12 provides a side view of a sleeve 7200 configured to provide convective heating and/or compression to a limb 7201 of a patient. The sleeve 7200 may comprise one or more bladders 7206 configured to be inflated with gas and/or fluid. The sleeve 7200 may further comprise one or more fluid chambers or channels 7208 configured to carry heating and/or compression fluids/gases. For example, the one or more chambers 7208 may be configured to fill with heated fluid to deliver warming therapy to various areas of the patient's limb 7201. In some embodiments, the gas and/or fluid passing through the one or more chambers 7208 may be configured to deliver compression to various areas of the limb 7201. In the example shown in FIG. 72, the sleeve 7200 may comprise a single fluidly-connected chamber/channel 7208. However, the sleeve 7200 may comprise any number of chambers 7208. The flow of the heated fluid through the channel(s)/chamber(s) 7208 can improve the heat transfer characteristics of the sleeve through convective effects of the moving fluid.

Figure 13:
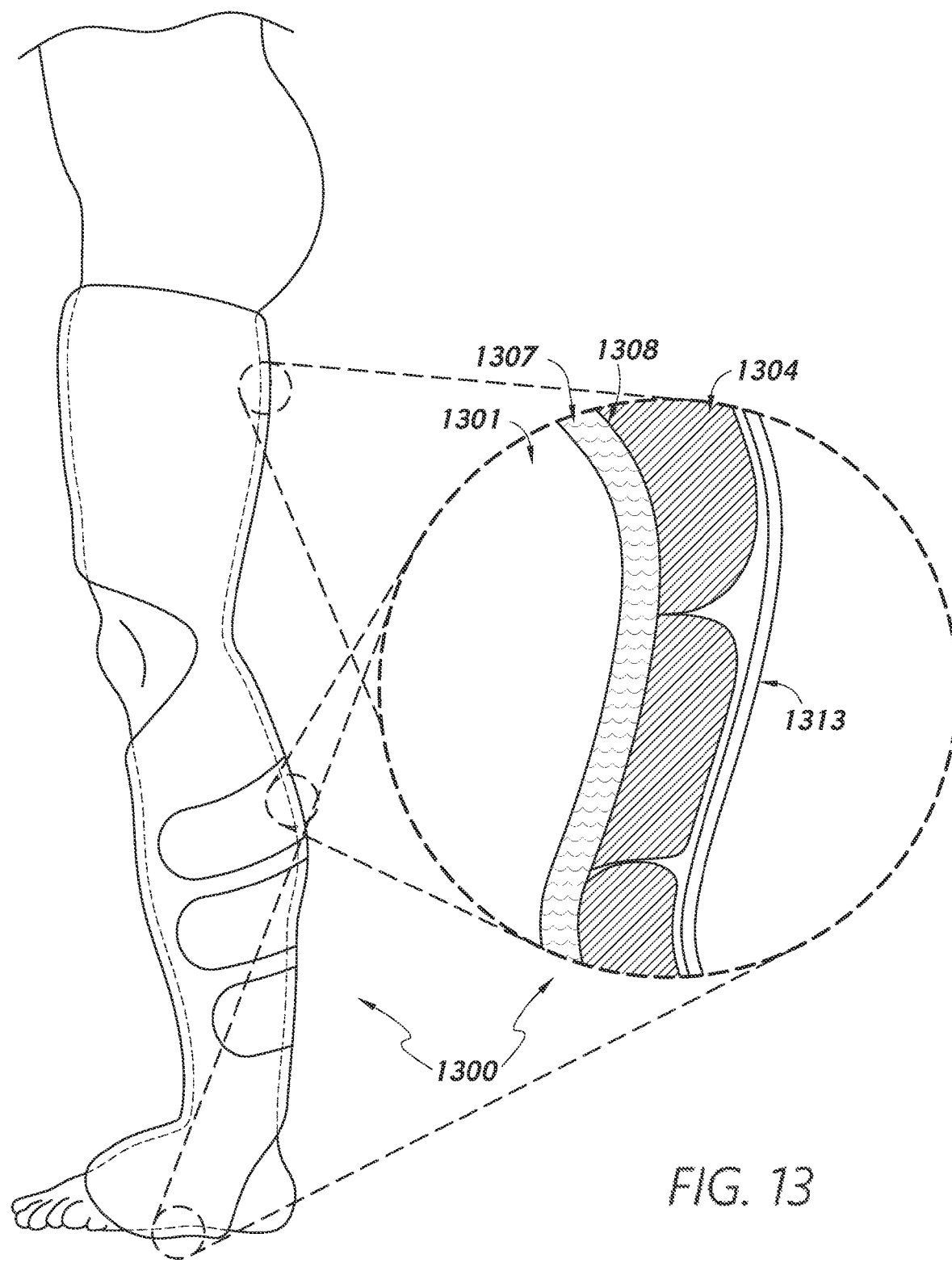
FIG. 13 provides a close-up view of a sleeve configured to provide heating and/or compression to one or more areas of a patient's limb in accordance with one or more embodiments.

FIG. 13 provides a dose-up view of certain portion(s) of a sleeve 1300 configured to provide heating and/or compression to one or more areas of a patient's limb. In some embodiments, the sleeve 1300 may be configured to apply warming throughout some or substantially all of the patient-contacting portions of the sleeve 1300 that are associated with heating elements) 1307. In some embodiments, the warming may be generated through the same material that houses the compression elements or through a separate layer disposed at least in part between the compression element(s) and the patient's skin (i.e., internal to the compression element(s)). For example, one or more compression elements 1304 may be configured to be inflated with heated gas and/or fluid, which may cause heated gas 1307 to fill a chamber 1308 in contact with the patient's skin 1301 and/or adjacent to the one or more compression elements 1304. In some embodiments, the heating element/chamber 1308 may be at least partially composed of one or more thermoelectric or resistive-heating pads or devices. In some embodiments, the heating element/chamber 1308 may be patterned and/or configured to allow for desirable physical deformation during compression, such as to accommodate certain anatomical features. In some embodiments, the heating element/chamber 1308 and/or other warming portions may be independent of the compression elements 1304, wherein the element/chamber 1308 may be applied directly to the patient prior to the placement of the compression elements 1304 to the respective limb. The elements/chambers 1308 may be configured to provide heating using one or more of electrical resistance, exothermic chemical reaction, ultrasound, and radiation. The element/chamber 1308 may be directly affixed to the patient using one or more of adhesives, retention members, and electromagnetic forces.

The compression elements 1304 and/or an outer layer 1313 of the sleeve 1300 may at least partially overlap and/or cover the heating element/chamber 1308 to enhance the effectiveness of heat transfer from the element/chamber 1308 to the desired anatomical region (e.g., the popliteal fossa and/or sole of the foot). In some embodiments, the use of a compressible material at the compression elements 1304 posterior (i.e., behind) to the chamber 1308 may improve skin contact and help provide an even distribution of warming. The compressible material may be immediately behind/external-to the chamber 1308 and internal to the outer layer 1313 where various sleeve fixation elements may be located. The material thickness of at least some portions of the sleeve 1300 may be, for example, between 5 mm and 15 mm but can range from 1 mm to 40 mm, or thicker.

In some embodiments, single or multiple compression elements 1304 (e.g., bladders) may be positioned behind/posteriorly-to the heating element/chamber 1308 to enhance skin contact of the heating element/chamber 1308. The compression element(s) 1304 may be configured to remain perpetually in an inflated state and/or may be inflatable at fixed or varying intervals and/or for fixed or varying durations. In some embodiments, a compression element(s) 1304 may have a non-uniform shape to accommodate the anatomy of the heating element/chamber 1308. The use of an adhesive substance on the internal surface of the element/chamber 1308 may be applied to enhance the efficacy of heat contact to the anatomical location. In some embodiments, the sleeve 1300 may comprise a heating element pattern, form, or material that may remain sufficiently biased towards the anatomy of a patient without the assistance of additional biasing members.

In some embodiments, the heating element/chamber 1308 may be configured to stretch and/or the outer layer 1313 may be configured to stretch or not to stretch. The compression elements 1304 may be configured to press the heating element/chamber 1308 against the skin 1301 to create and/or maintain surface contact between the skin 1301 and the chamber 1308 and/or the compression elements 1304 may be configured to induce circulation and/or increase flow of blood in the patient's limb. In some embodiments, the compression elements 1304 may be configured to be intermittently inflated and deflated to create intermittent contact between the element/chamber 1308 and the skin 1301.

Figure 14:
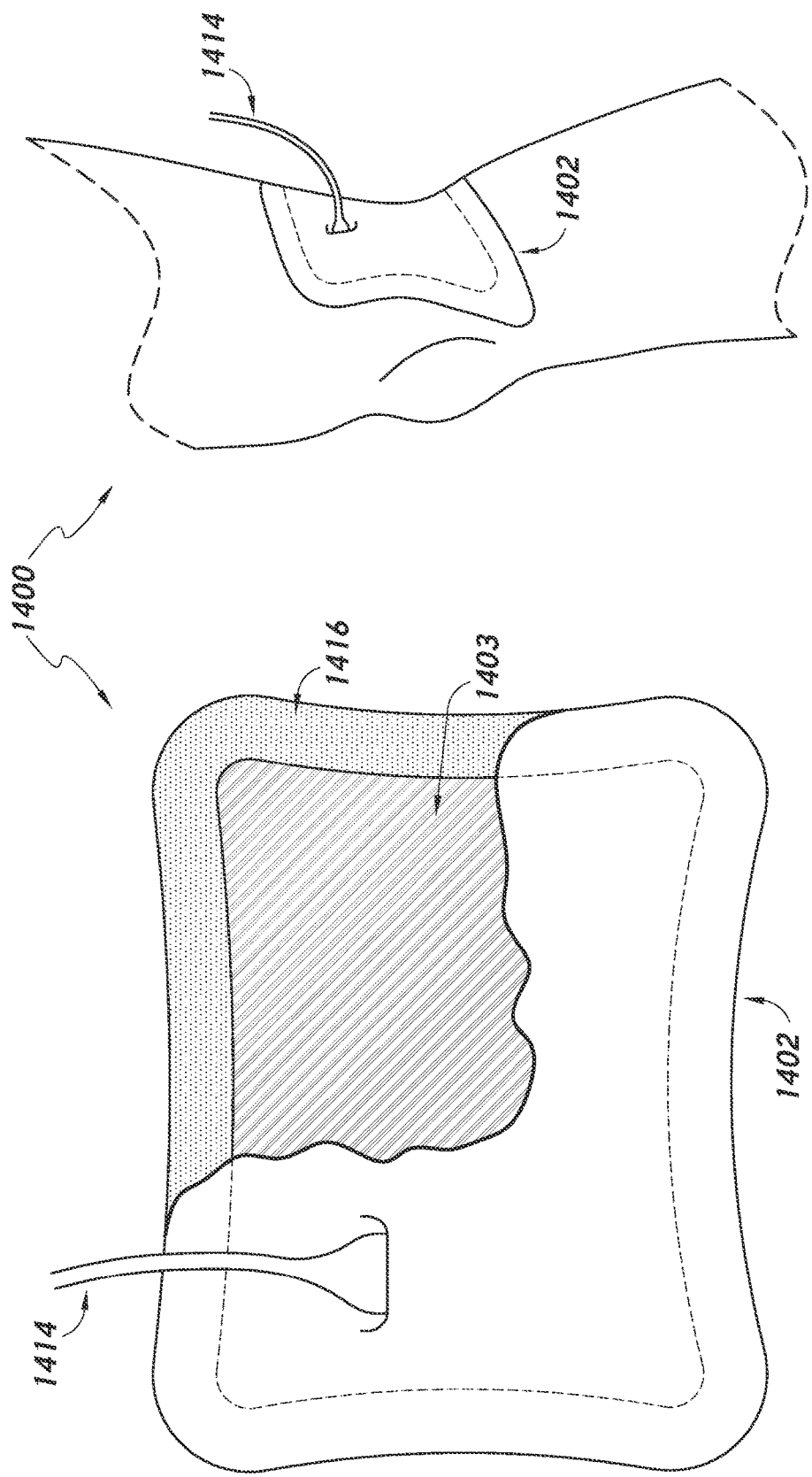
FIG. 14 provides an illustration of at least a portion of a sleeve for maintaining or increasing the body temperature of a patient in accordance with one or more embodiments.

FIG. 14 provides a cutaway view of at least a portion of a temperature management sleeve or patch device 1400 for maintaining or increasing core body temperature of a patient. In some embodiments, the sleeve/patch 1400 may include an electrical connection interface channel/connector 1414 configured to be connected between a heating element 1402 and an energy source for the heating element 1402. The electrical connection 1414 to the heating element 1402 may be configured to be biased medially or laterally along an edge of the heating element. In some embodiments, a sleeve/patch 1400 configured for providing heat to a sole of a foot may include the electrical connector 1414 proximally located along a vertical edge and distally biased so to lay flat on the patient bed during use. The electrical connector 1414 may be disposed/positioned in a laterally offset position, as shown, so as to remain free from the posterior region of the limb, for example, the sole of the foot or the popliteal fossa. In some embodiments, the electrical connector 1414 may include a stress-relief feature just proximal to the electrical connector 1414. The stress-relief feature and electrical connector 1414 may be further configured to maintain a hermetic seal, which may be achieved through mechanical interference, one or more O-rings, gaskets, adhesives, sealants, grease, and plugs, or the like.

In some embodiments, the sleeve/patch 1400 may comprise an adhesive 1416 around an outer border of the heating element. In some embodiments, the adhesive portion 1416 may be configured to seal the sleeve/patch 1400 to an area of skin of the patient. In some areas, the adhesive portion 1416 may be configured to overlap with a warming region 1403 of the sleeve/patch 1400. The adhesive 1416 may comprise hydrogel and/or other suitable substance. In some embodiments, the adhesive 1416 may be at least partially thermally conductive. In optional embodiments, the adhesive 1416 may be heated and/or may be used as a heating element in the warming region 1403.

The electrical connector 1414 may be configured to be coupled to an interface of one or more compression bladders and/or fluid transferring members. For example, the electrical connector 1414 may be coupled to fluid tubing and/or electrical wire(s)/trace(s). In some embodiments, the electrical connector 1414 may comprise at least one fluid-transferring channel, at least one heating energy (e.g., electrical energy) channel, at least one sensor feedback transmission line, and/or at least one ground interface, wherein the electrical connector may be configured to maintain hermetic seals to each other and/or to the external environment. Furthermore, the heating, sensor, and ground channels/interfaces of the multi-channel electrical connector 1414 may be configured to provide electrical connectivity achieved through electrical connector(s) to either a device controller at one end and a connecting cable at the other, or a connecting cable at one end and a device sleeve/patch on at other, or a device controller at one end and a device sleeve/patch at the other. In some embodiments, the sleeve/patch 1400 may comprise at least one multi-channel connector configured to support at least one compression element, at least one heating element 1402, and/or at least one temperature sensor. The sleeve/patch 1400 may be configured to be connected to more than one device controller through more than one electrical connector 1414. Each controller may be configured to deliver the same modalities (compression and/or heating) or different modalities.

Ease-Of-Use Features of Limb Sleeve Devices

In some embodiments, the sleeves described herein may be configured to fit into an existing hospital workflow. For example, a sleeve device may be configured to functionally drive sequential compression and/or provide heat to various target areas of a patient (e.g., the sole of the foot and/or the popliteal fossa). In some embodiments, the sleeve may allow for at least limited patient mobility (e.g., a patient may walk around while wearing the sleeve). One or more sleeves may be configured to provide a universal fit (e.g., no left-/right-bias). Some sleeves may be configured for single-use and/or multi-use. Moreover, the approximate operating life of a sleeve may be at least eight hours.

Figure 15:
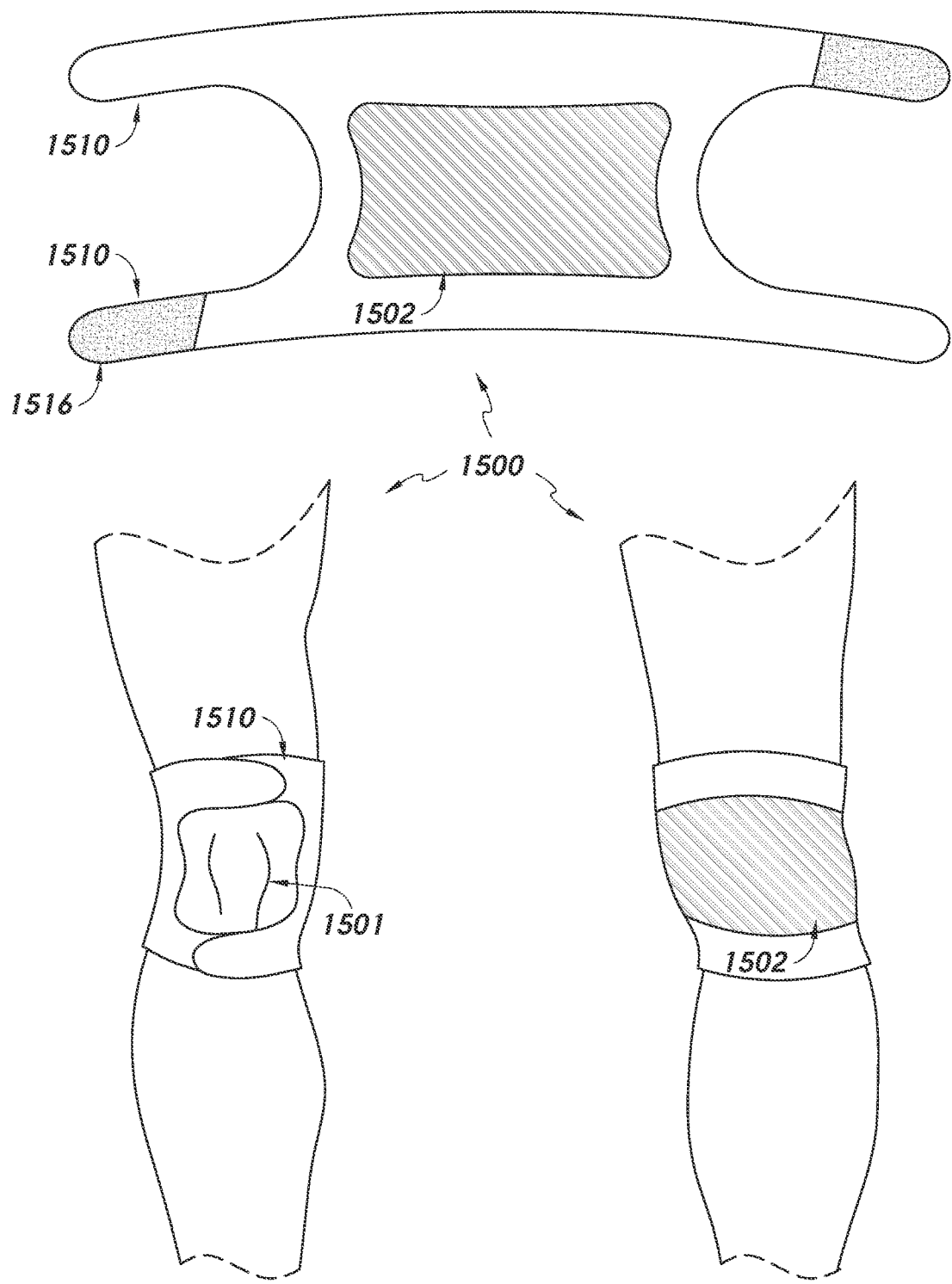
FIG. 15 provides views of a sleeve configured to provide improved ease-of-use in accordance with one or more embodiments.

FIG. 15 provides views of at least a portion of a sleeve 1500 configured to provide improved ease-of-use. In some embodiments, the sleeve 1500 may comprise a warming portion 1502 configured to deliver heat to a target area (e.g., the popliteal fossa) when the sleeve 1500 is placed over a patient's knee and/or other body part(s). The sleeve 1500 may also comprise one or more straps 1510, some of which may comprise a attachment/fastening feature 1516 (e.g., Velcro, adhesive, clip(s), hook(s), or the like) to allow the sleeve 1500 to be adhered to skin of a patient and/or to other portions of the sleeve 1500 (e.g., at the strap(s) 1510).

The sleeve 1500 may comprise various decals, icons, and/or other visual indicators indicating proper orientation of the sleeve 1500, such as at desired area(s) of a patient's limb. In some embodiments, the sleeve 1500 may be configured such that the straps 1510 surround the kneecap 1501 of the patient, as shown. For sleeves 1500 configured for application at/on a foot of a patient, the sleeve 1500 may comprise a heel locator, for example.

In some embodiments, the warming portion 1502 may be configured to be placed against the skin of the patient, whether or not the warming element associated therewith is covered by one or more layers of material/fabric or not. The warming portion 1502 may comprise a compressible foam pad and/or other materials configured to maintain constant surface contact and/or pressure of the sleeve 1500 and/or warming portion 1502 against the skin. In alternative embodiments, the sleeve 1500 may comprise one or more compression bladders. Such compression bladder(s) may not be intermittently pumped and/or may be fully inflated for the duration of the operation.

The sleeve 1500 may comprise an elastic material such that the sleeve 1500 may be configured to stretch to maintain surface contact and/or pressure at the skin. Such elasticity may present a substantially constant force against one or more areas of the skin when the sleeve 1500 is configured on the patient's limb. In some embodiments, the sleeve 1500 may comprise one or more elastic strips welded or otherwise attached/coupled to the sleeve 1500. The straps 1510 of the sleeve 1500 may be configured to be position at various angles and/or tensions to change the stretch and/or compression point from an edge of the warming portion 1502 to a center position of the sleeve 1500.

In some embodiments, the sleeve 1500 may comprise a compression element configured to be situated at a top portion of a calf muscle of the patient. A compression element may comprise an assembly consisting of multiple welded/coupled compression bladders. Each compression bladder may be configured to be connected to an independent channel of the sleeve connector and/or gas/fluid may be pumped into and/or out of the bladders to create compression on the encapsulated/proximate, limb portion. In some embodiments, compression bladders may have "dimpled" elements (e.g., periodic holes welded, pressed, and/or cut in the bladder) to improve compression uniformity around the target limb portion. For example, the compression element may be a pre-assembled part that may be integrated into the sleeve 1500 in the final assembly.

FIG. 16 provides side views of an inflatable sleeve 1600 in a deflated state 1600a and in an inflated state 1600b. The sleeve 1600 may comprise a warming portion 1602 configured to contact a patient's skin and/or deliver heated gas to the patient's skin. In some embodiments, the sleeve 1600 may comprise a compression portion 1604 configured to be inflated with gas/fluid. The gas/fluid may be heated to provide warming functionality as described herein.

In the deflated state 1600a, a curvature of the popliteal fossa 1601 region of the patient's knee area may create a gap 1609 between the warming portion 1602 and the skin of the patient and/or may otherwise prevent the warming portion 1602 of the sleeve form contacting the skin in a uniform manner. However, when the compression portion 1604 is inflated in the inflated state 1600b, the compression portion 1604 may be configured to press the warming portion 1602 to create and/or maintain contact between the warming portion 1602 and the skin 1601 at the popliteal fossa. The warming portion 1602 may include any type of heating element(s), including one or more heating pads (e.g., comprising one or more resistive heating conductors), heated-fluid channels, chemical heating materials, and/or the like.

Figure 17:
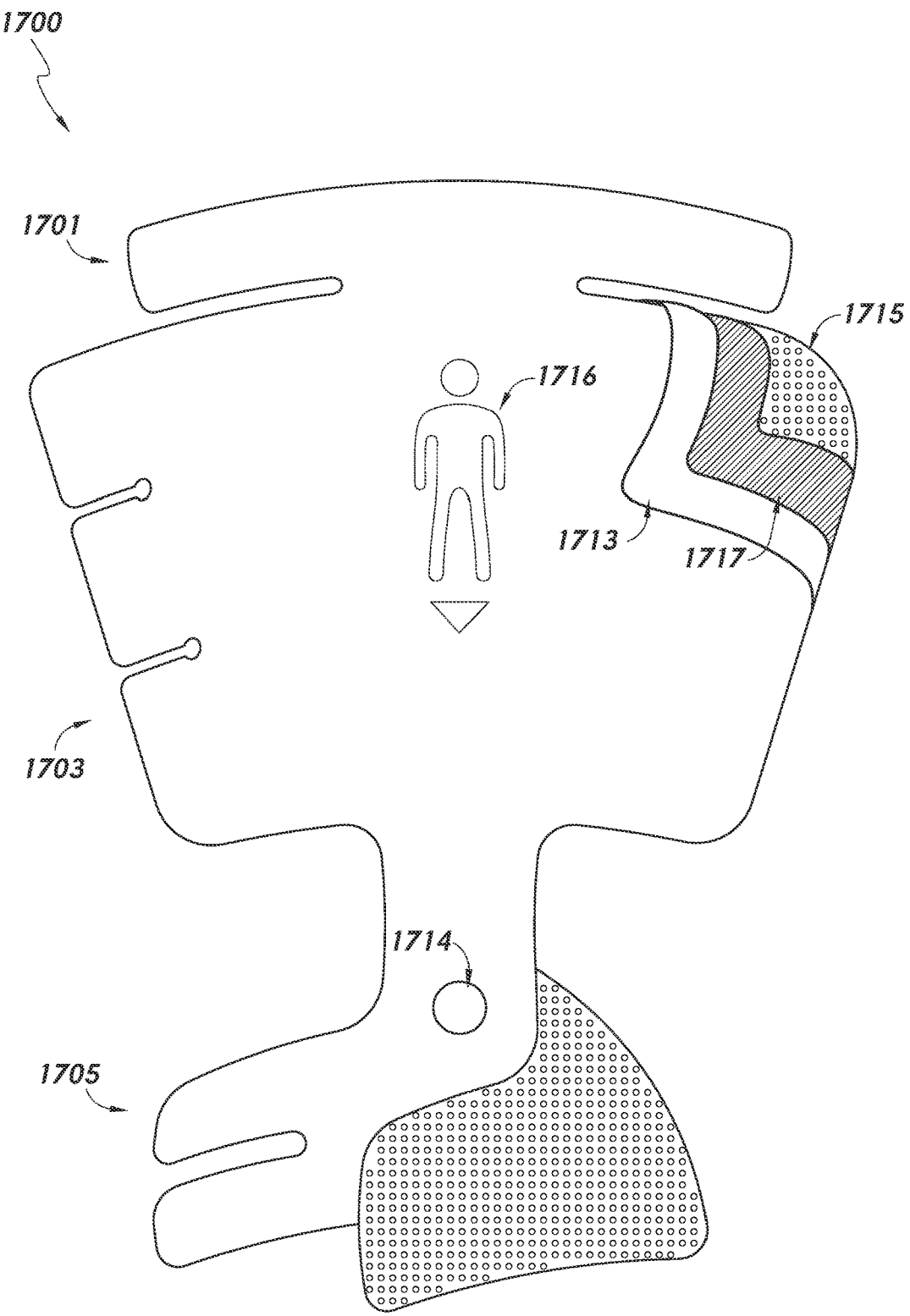
FIG. 17 illustrates an example sleeve comprising various physical, visible, and/or palpable anomalies or markers to improve the ease-of-use of the sleeve in accordance with one or more embodiments.

FIG. 17 illustrates an example sleeve 1700 comprising various physical, visible, and/or palpable anomalies or markers to improve ease-of-use of the sleeve 1700. In some embodiments, the sleeve 1700 may comprise a heel locator 1714 (e.g., a cavity and/or opening in the sleeve 1700) to indicate a specific anatomical placement for the patient's heel. Other anomalies and/or markers may include a cavity and/or opening in the sleeve 1700 for the patient's knee. The sleeve 1700 may include extendable and/or collapsible sections (e.g. dimensionally adjustable and/or elastic regions that enable the knee region, ankle, and foot region to be stretched to the desired length prior to application) within the sleeve 1700 body that may enable universal placement of a single-size sleeve 1700 on a majority of the adult patient population. In some embodiments, a sleeve 1700 may comprise one or more adhesive regions (including, e.g., self-adhering sections such as Velcro, buttons, etc.) to allow portions of the sleeve 1700 to adhere and/or attach to other portions of the sleeve 1700 to collapse and/or compress the sleeve 1700.

Various features of the sleeve 1700 may be configured to facilitate correct placement of the device to a patient's limb. Such features may include visual marks, surface variations, cavities for anatomical landmarks, and/or unique form factors. In some embodiments, the heel locator 1714 may comprise a hole, slit, or similar opening in the sleeve that is designed to be placed specifically around the heel. The heel locator 1714 may additionally or alternatively be marked by one or more visual indicators (e.g., text and/or graphics) that may be sufficiently distinguishable by the human eye. Such visual indicators may be included independently of, or in conjunction with, the described anatomical hole, slit, or similar opening. In some embodiments, placement features may be adapted to any of the knee, elbow, wrist, shoulder, and/or other key anatomical landmarks/features. In some embodiments, the sleeve 1700 may comprise differing materials, textures, and/or colors distinguishing between an inner surface 1713 (e.g., a skin-contacting surface) and an outer surface 1715 (e.g., an environment-facing surface).

In some embodiments, the sleeve 1700 may include an orientation indicator 1716 indicating correct orientation of the sleeve 1700 with respect to the patient and/or the patient's limb. The orientation indicator 1716 may be configured to indicate correct placement of the sleeve 1700. In some embodiments, a first portion 1701 and/or second portion 1703 of the sleeve 1700 may be larger in diameter than a third portion 1705 of the sleeve, as the first portion 1701 and/or second portion 1703 may be configured for placement over larger areas of the patient's limb (e.g., the thigh, knee, and/or calf) while the third portion 1705 may be configured for placement at the patient's foot and/or ankle. The orientation indicator 1716 may comprise one or more visual indicators, which may include text and/or graphics. In some embodiments, the orientation indicator 1716 may be printed at an outer surface of the outer layer 1713. The outer layer 1713 and/or outer surface of the outer layer 1713 may comprise features configured to increase surface friction of the sleeve 1700 to prevent slipping. For example, the outer layer 1713 limy comprise, various materials (e.g., silicone strips) and/or textures printed and/or embedded into the outer layer 1713 and/or outer surface of the outer layer 1713 (e.g., at the third portion 1705 which may be configured to be placed over the sole of the foot) to increase surface friction.

The inner layer 1715 may comprise mesh or similarly breathable material. The outer layer 1713 may comprise any suitable material. In some embodiments, the outer layer 1713 may comprise one or more materials configured to attach to Velcro and/or other attachment materials and/or mechanisms. The sleeve may comprise a middle layer 1717 between the inner layer 1715 and the outer layer 1713. In some embodiments, the middle layer 1717 may comprise a wicking material and/or other at least partially breathable material. In some embodiments, the inner layer 1715 may be configured to contact a patient's skin and/or may be at least partially temperature-controlled. In some embodiments, the inner layer 1715 middle layer 1717, and/or outer layer 1713 may be configured to allow for layer deformation in support of deep vein thrombosis (DVT) prophylaxis.

Figure 18:
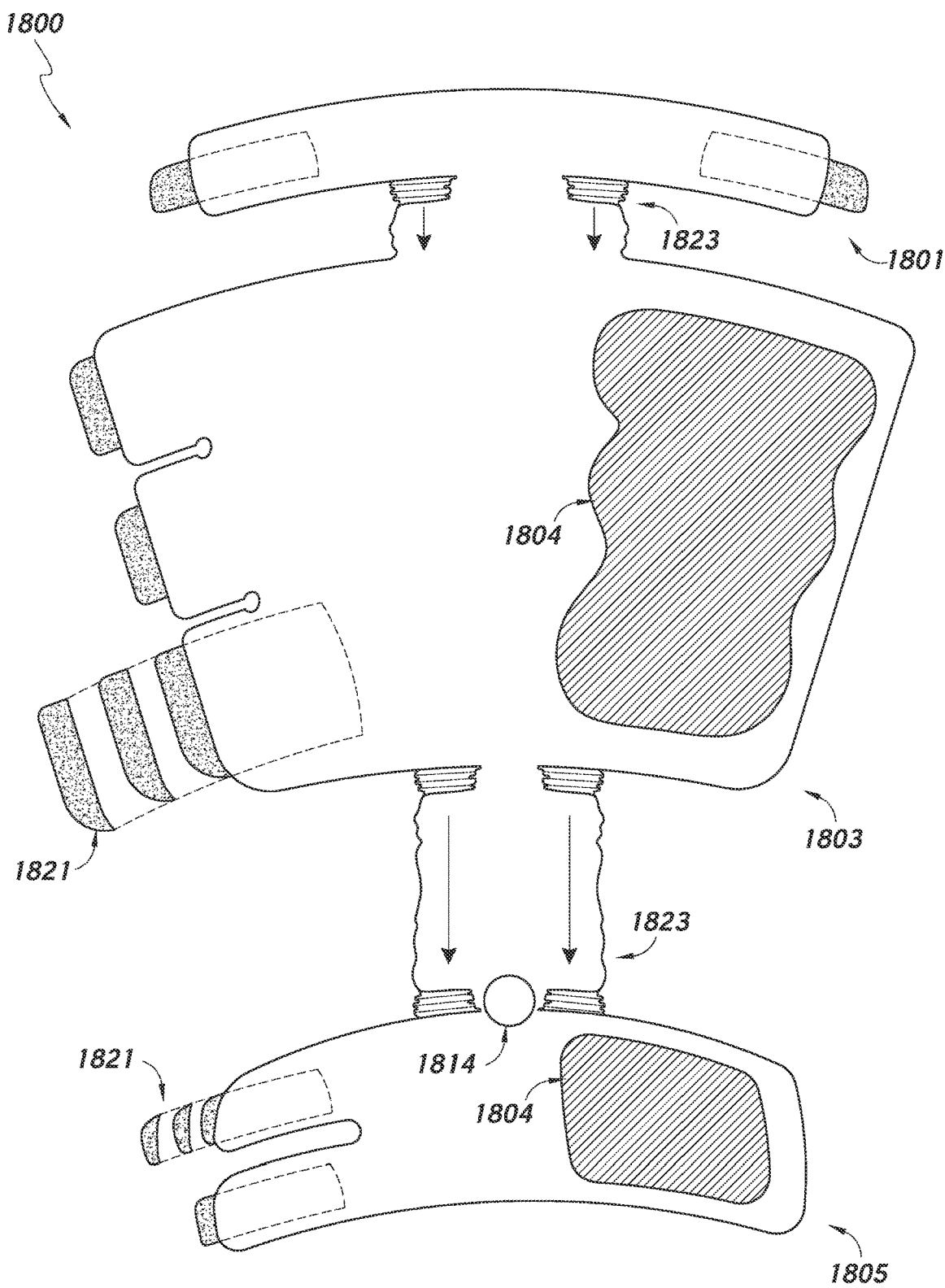
FIG. 18 illustrates an adjustable sleeve configured to provide heating and/or compression to one or more areas of a patient's body in accordance with one or more embodiments.

FIG. 18 illustrates an adjustable sleeve 1800 configured to provide heating and/or compression to one or more areas of a patient's body. The sleeve 1800 may comprise one or more compression elements 1804, which may include inflatable bladders. In some embodiments, the sleeve 1800 may be configured to deliver pneumatic sequential compression of various target areas (e.g., the calf and/or foot). The sleeve 1800 may be configured to receive pneumatic (e.g., heated) gas and/or other fluid for conductive heat transfer in support of core body temperature regulation. In some embodiments, temperature and/or pressure regulation functionality for the sleeve 1800 may be managed at a controller (e.g., 50.5 C exiting the controller, 40 mmHg/130 mmHg feedback).

The sleeve 1800 may be configured to provide compression and/or heating to one or more of the patient's thigh (or at least above-the-knee areas of the patient's leg), knee, calf, and/or foot. The one or more compression elements 1804 may be configured for placement at, for example, the calf and/or sole of the foot. The compression elements 1804 may be configured to be sequentially inflated and/or deflated to compress the tissue and drive venous return. In some embodiments, the sleeve 1800 comprises a compression element configured to be positioned behind the knee to provide a heated surface to the popliteal fossa.

Gas and/or fluid provided to the sleeve 1800 may be heated within a controller or associated device to a specified temperature set point before delivery to the sleeve 1800. In some embodiments, the fluid may be selectively heated so that only compression elements 1804 covering certain target areas (e.g., the sole of the foot and/or popliteal fossa) may be elevated in temperature to reduce power requirements. Heat control may be open-loop (e.g., toggled on-off and to specified temperatures by a clinician) or closed-loop from an external temperature probe (e.g., core body temperature—esophageal, tympanic, etc.).

In some embodiments, the sleeve 1800 may be configured to inflate and/or deflate in multiple sequences. For example, an inflation/deflation sequence of the sleeve 1800 at a first portion 1801 and/or third portion 1805 may be different from the inflation/deflation sequence of the sleeve 1800 at a second portion 1803. In some embodiments, to maintain surface contact with the skin tissue, one or more compression elements 1804 may not completely deflate. For example, to avoid restricting blood flow, a compression element 1804 configured to be placed at or near a knee of a patient may have a lower maximum pressure compared to compression elements 1804 configured for placement at a calf and/or foot portion of the patient. Inflation/deflation cycles may be relatively rapid (e.g. every 10 seconds) to maintain high temperatures. It should be understood that, as with any of the other embodiments disclosed herein, in some implementations, the knee portion 1801 and foot portion 1805 do not have compression bladder(s) and/or are not designed for compression therapy, whereas the calf portion 1803 includes one or more compression bladders or other compression components.

In some embodiments, the compression elements 1804 may comprise one or more pneumatic bladders configured to adjust the position of the sleeve 1800 and lower limb for optimal heat transfer. The sleeve 1800 may comprise one or more perforated channels or areas used to provide convective heat transfer to various target areas (e.g., the popliteal fossa and foot sole) in support of core body temperature regulation. The one or more perforated channels may be patterned into the sleeve 1800 (e.g., at the sole of the foot and the back of the knee) for heat transfer. In some embodiments, the sleeve 1800 may comprise additional compression/bladder elements (e.g. above the knee and/or at the heel and/or ball of the foot) to provide spacing of the one or more perforated channels away from the skin (e.g., to allow convective flow).

The compression elements 1804 may be inflated/deflated according to pressure sequences that may be advantageous for DVT prophylaxis (e.g., approximately one minute on-off cycle). The gas and/or fluid in the compression elements 1804 may be heated and/or may be uncontrolled for temperature. The inflation level of the compression elements 1804 may be controlled by pressure sensors located in a controller.

One or more of the compression elements 1804 may be utilized as supporting bladders for one or more warming elements. Accordingly, one or more compression elements 1804 may be inflated to a lower pressure than other compression elements 1804 to provide spacing but not cut off blood flow. The compression elements 1804 may be inflated when heating is turned on and/or may be deflated when no heating is required.

One or more perforated channels may be provided with heated gas (e.g., air) by a controller. When in heating mode, the controller may provide a continuous supply of heated gas at a defined set point. Gas and/or fluid temperature may be monitored/controlled using a temperature sensor (e.g., thermocouple, resistance temperature detector, thermistor, etc.) residing in the controller device. The flow rate of the gas and/or fluid may be tuned to match the perforations of the sleeve 1800 so that the channels may be continuously in a partially inflated state.

Temperature regulation of the gas and/or fluid may be manually controlled by a clinician (e.g., using an on/off toggle) and/or automatically via an external temperature probe (e.g., providing information about core body temperature).

In some embodiments, the compression elements 1804 may be circumferential or non-circumferential. For example, compression elements 1804 utilized as supporting bladders may take the form of a "pillow" that may not wrap entirely around the patient's limb but may instead protrude at or near one or more outer edges of the sleeve 1800. The sleeve 1800 may comprise one or more supporting bladders that may be composed of a compressible material (e.g., foam). Such supporting bladders may not utilize intermittent compression unlike other compression elements 1804.

One or more target areas of the patient's body may be heated and/or compressed using a single channel or multiple channels. For example, an area behind the knee and the sole of the foot may be heated using a single channel or may be independently operated. In some embodiments, temperatures at different portions of the sleeve may be independently adjustable.

The sleeve 1800 may be configured to apply heating at various target areas (e.g., the popliteal fossa and sole of the foot) using, for example adhered heating patches which have any of a variety of forms. For example, the sleeve 1800 may comprise (1) an inflatable heating bladder for fluid-based, conducting heating, (2) a wire-based patch for resistive, conductive heating, (3) a battery-operated, wireless patch for resistive, conductive heating, and/or (4) a topical chemistry configured to generate an exothermic reaction for chemical, conductive heating. Heating patches may be configured to be adhered directly to the skin (e.g., forming an air-tight and/or water-tight seal). Some embodiments may involve the heating patches being placed and/or attached as an additional piece to a DVT prophylaxis sleeve, and/or may be positioned separately as independent sleeves/wraps. In some embodiments, temperature sensors may be integrated into heating patches and/or may reside within a controller. In the case of chemical application, no temperature sensor may be required.

In some embodiments, the sleeve may be configured to be adjustable to varying sizes to accommodate varying sizes of patients' limbs. However, a single size may be manufactured with features enabling the placement of the sleeve 1800 across a wide range of anatomical sizes. The sleeve 1800 may have adjustable features including tightening straps 1821 and/or collapsible/extendable regions 1823. The adjustable features may be situated either along the entire device or in specific segments along the device and/or may allow universal placement of a single sleeve 1800 design. For example, in one embodiment, a third portion 1805 area of the device immediately proximal to a heel locator 1814 may be intentionally oversized in length so that it may be configured to be folded upon itself to accommodate limbs of different lengths. In some embodiments, the third portion 1805 may contain a clasp or adhesive feature to hold the excess material, if any, in place. The third portion 1805 may be replaced by a material with dynamic physical properties that can enable the device to elongate and accommodate limbs of different lengths and/or sizes. For example, at least a portion of the sleeve 1800 may be configured for two-way (i.e., single-axis) and/or four-way (multi-axis) stretching. In such an embodiment, the sleeve 1800 may have a greater elongation in the vertical direction than the horizontal direction. Varying elasticity or elongation properties of the device or specific segments of the device may be manufactured from the same or different material with same or different material properties as the remaining portion(s) of the sleeve 1800.

The sleeve 1800 may comprise various fixation elements which may be utilized for intuitive placement through the unique placement, shape, materiality, and color of the fixation elements. In some embodiments, a first portion 1801 may be placed above, below, or circumferentially around a knee with a form factor such that when pulling the strap superiorly and around the kneecap, the strap may secure only horizontally around the kneecap and not at an angle. In this way, a first arm of the first portion 1801 may be configured to at least partially overlap with a second arm of the first portion 1801. In some embodiments, the first portion 1801 may be configured to create force based at least in part on the angle of placement at the patient's limb. For example, the angle of placement of the first portion 1801 may be configured to prevent an upper edge of the sleeve 1800 from sliding down the patient's limb. The sleeve 1800 may comprise a plurality of wraps that can be applied to a patient's limb whereby each one of the pluralities of wraps may further comprise tightening straps 1821. In some embodiments, individual compression elements 1804 may not be joined along their full lengths so that when they are applied, one can be crossed over the other, as to allow the angulation of the application of the upper bladder to accommodate the calf area horizontally.

In some embodiments, the sleeve 1800 may be configured to be placed using a combination of fixation members and/or self-fixating regions. The sleeve 1800 may comprise multiple independent circumferentially closed, self-fixating regions that can be applied directly over the entire limb and pulled up to the desired location on the limb. The sleeve 1800 may be configured to self-contract or expand so as to maintain sufficient contact with the limb and remain sufficiently fixated in position. In some embodiments, the sleeve 1800 may be entirely circumferentially closed with no additional fixating members.

Interfacing Between Limb Sleeve and Control Unit

Figure 19:
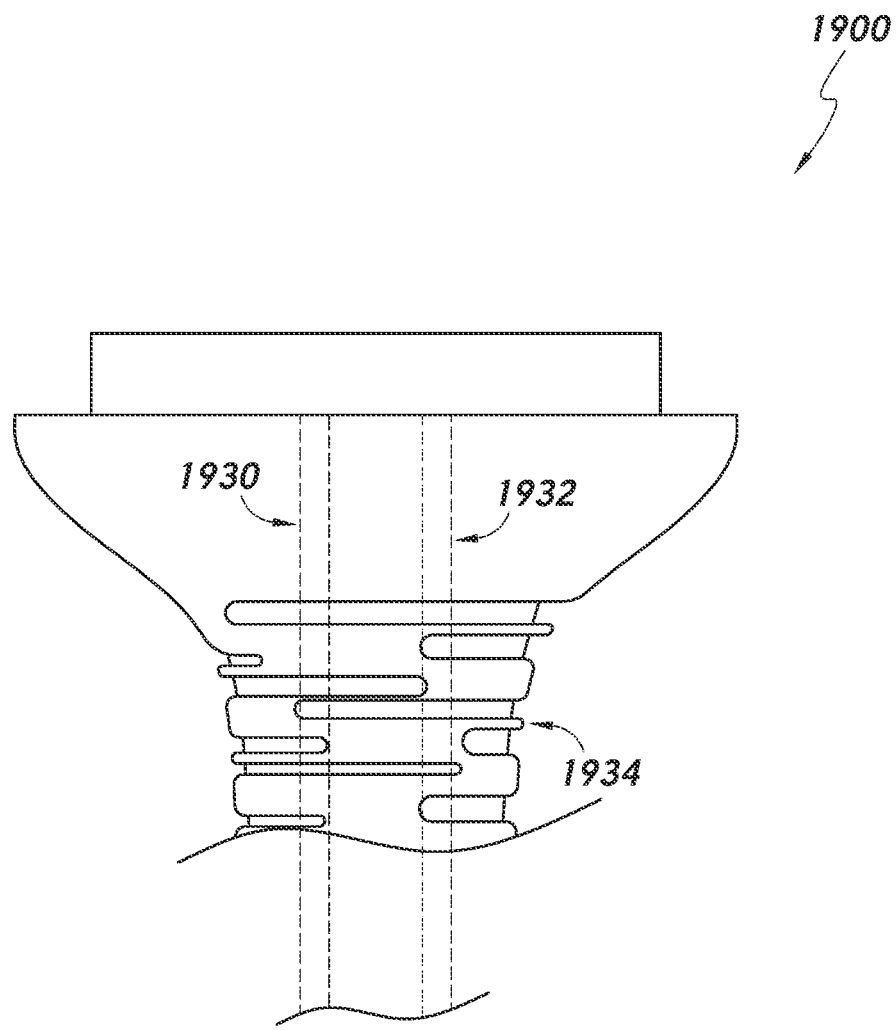
FIG. 19 illustrates an interface for connecting one or more sleeves to a controller in accordance with one or more embodiments.

FIG. 19 illustrates an interface connector 1900 for connecting one or more sleeves to a controller. The interface 1900 may be configured to attach between a sleeve and the controller such that the interface 1900 can maintain a hermetic seal for delivering one or more channels, which may include an internal fluid channel 1930 and/or an electric channel 1932. The interface 1900 may be configured to maintain the hermetic seal to the external environment. In some embodiments, the interface 1900 may be configured to be attached in either of multiple possible fixation orientations or in a single orientation.

In some embodiments, inflation level of one or more compression elements at a sleeve may be controlled by pressure sensors located in a controller and the sleeve. Fluid temperature may be monitored and/or controlled using a temperature sensor (e.g., a thermocouple, RTD, thermistor, etc.) residing in the controller and/or the sleeve. In some embodiments, temperature regulation may be manually controlled by a user and/or automatically via an external temperature input. The interface 1900 may comprise a neck portion 1934 configured to be bent. For example, the neck 1934 may have built-in slack to allow for bending.

The neck portion 1934 may protect one or more of an electrical line 1930 and a fluid line 1932, which may provide for the reception and/or transmission of electric signals (e.g., data and/or power) and/or fluid (e.g., fluid pumping and/or provision). The neck portion 1934 may be configured to bend along one axis, two axes, or three or more axes. The connector 1900 may be a component of a sleeve or a connector.

Figure 20:
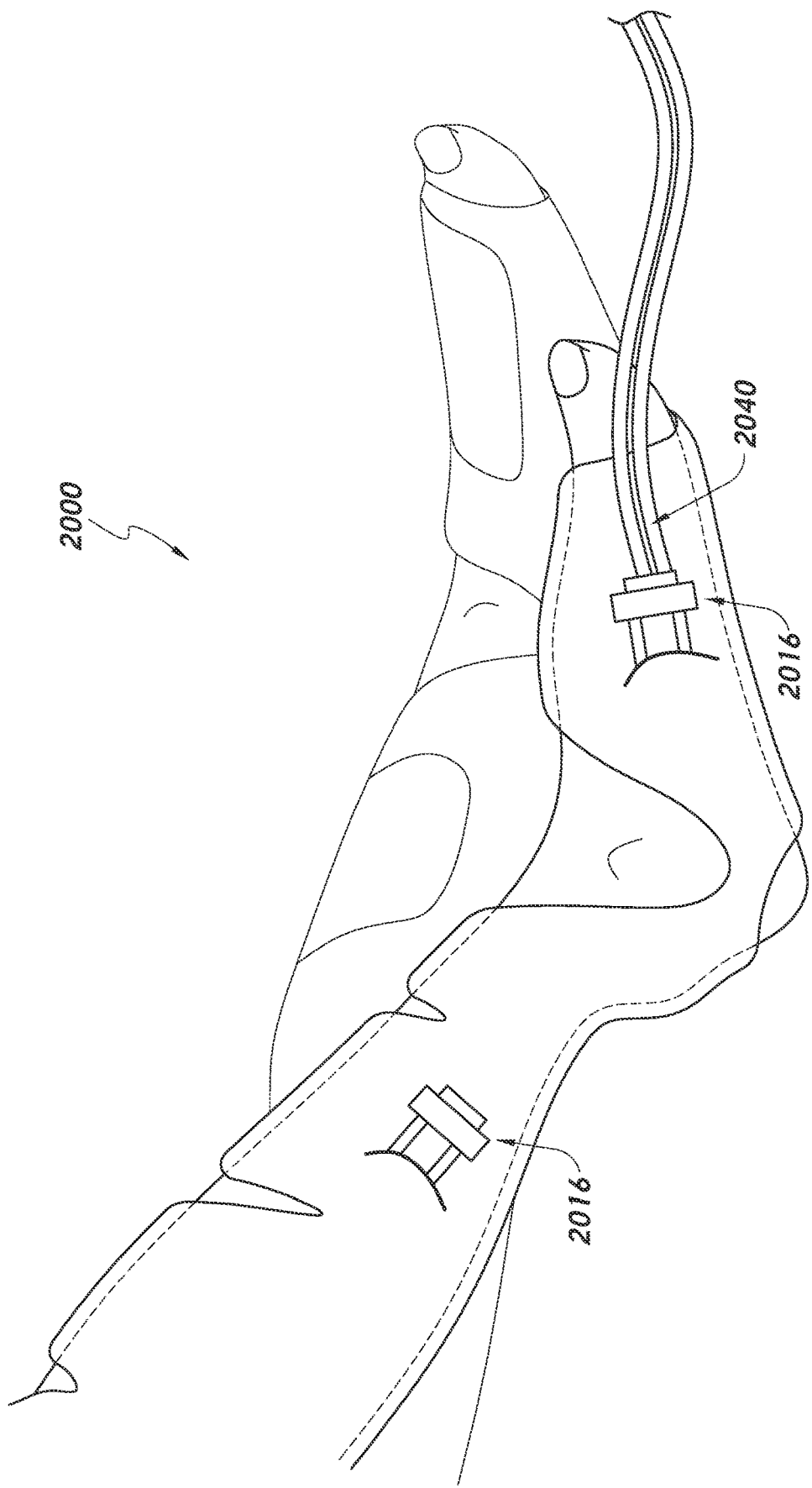
FIG. 20 illustrates sleeve comprising inlets configured to connect to a controller via an interface in accordance with one or more embodiments.

FIG. 20 illustrates sleeves 2000 comprising electrical and/or fluid connectors 2016 configured to connect to a controller via an interface. The sleeves 2000 may comprise various electrical cabling components, which may include one or more cabling components (e.g., two) per warming element and/or one or more cabling components (e.g., two) per temperature sensor (e.g., thermistor). The cabling components may be routed within the sleeve 2000 with enough length to provide strain relief for any stretch and/or bending applied to the sleeve 2000. Additional sleeve alignment features may be welded or otherwise attached/coupled in place to guide the cabling to preferred areas in the sleeve 2000. The alignment features may be configured to keep cabling away from pressure points (e.g., the patient's heel).

Cable routing may be designed to maximize patient comfort, minimize interference during a procedure, and/or minimize risk of injury (e.g., while the patient is mobile). For example, a foot sleeve may comprise a cable exiting next to the heel and/or a knee sleeve may comprise a cable exiting towards the heel. Cables may be bundled together to form a single cable per leg.

In some embodiments, one or more arms of the sleeve 2000 may be configured to be welded and/or otherwise attached to compression elements and/or compression sleeves. In some embodiments, multiple arms joined together may form a compression element above and/or below the kneecap of the patient.

Figure 21A:
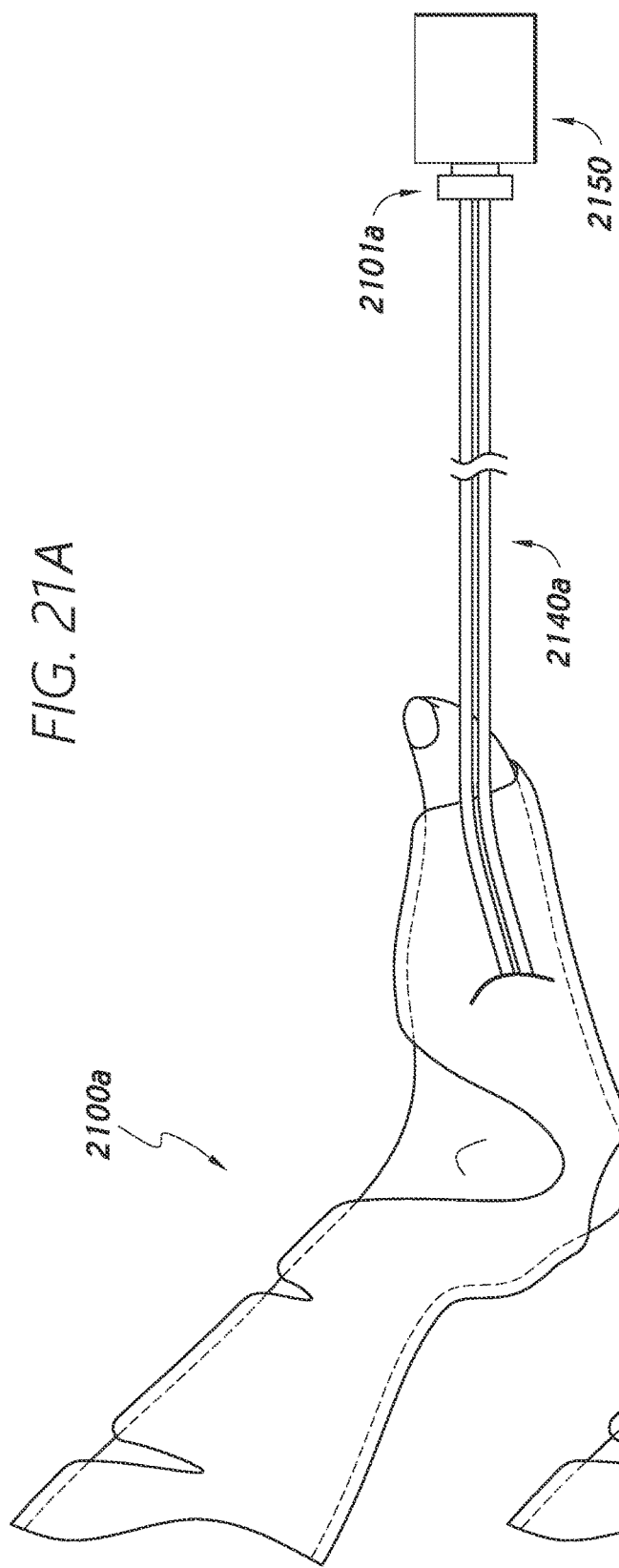
FIGS. 21A and 21B illustrate systems including one or more cable components connecting a sleeve to a controller in accordance with one or more embodiments.
Figure 21B:
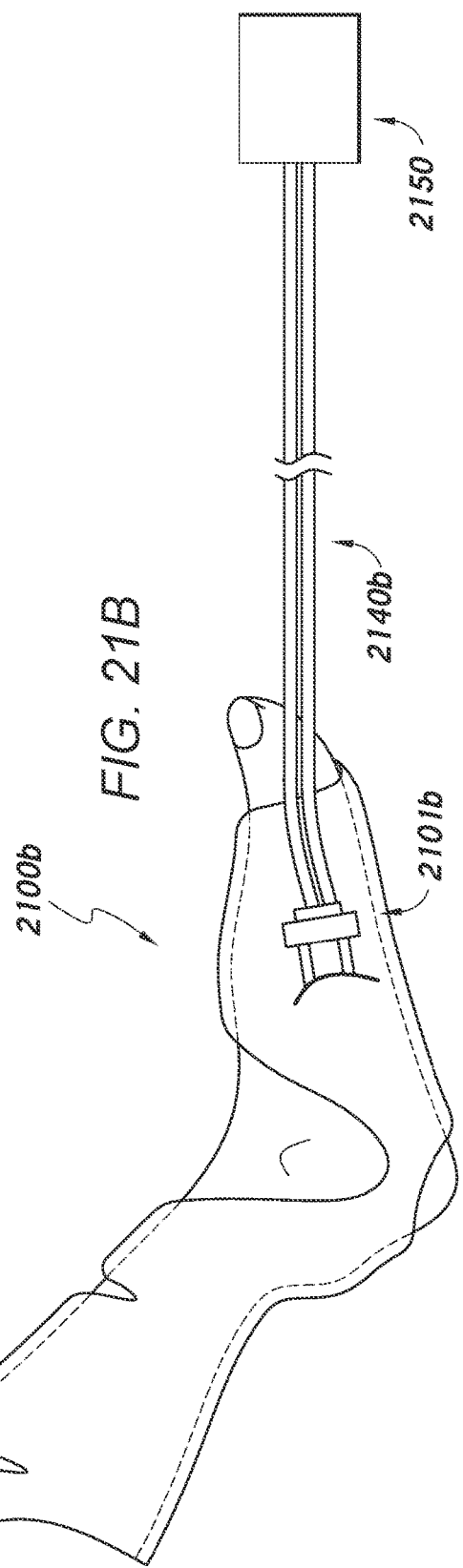

FIGS. 21A and 21B illustrate systems including one or more cables, wires, and/or tubes 2140 (referred to individually and/or collectively in the following description as "cable components") connecting a sleeve 2100 to a controller 2150. In some embodiments, fluid provided to the sleeve 2000 via the cable component(s) 2140 may be heated within the controller 2150 to a specified temperature before delivery to the sleeve 2100. The fluid may be selectively heated so that only bladders at the sleeve 2100 covering specific anatomical regions may be temperature modulated. In some embodiments, temperature control of the warming therapy may be open-loop (e.g., manually specified temperatures) or closed-loop (e.g., automatically controlled to maintain the desired temperature profile, such as in response to a sensor (e.g., temperature, pressure, etc.) feedback). For example, temperature feedback may be generated and/or provided relating to any of esophageal, tympanic, oral, inguinal urinary, and rectal temperatures.

In the illustrated configuration/embodiment of FIG. 21A the connector 2101a is associated with a distal end of the cable 2140, which is coupled to or integrated with the sleeve device 2100a, whereas in the illustrated configuration/embodiment of FIG. 21B, a connector 2101b associated with a distal end of a cable 2140b that is coupled to or integrated with the controller 2150b is connected to a corresponding connector of the sleeve 2100b. In some embodiments, a cable is used that has connectors at both ends thereof, wherein one of the connectors is configured to connect to a corresponding connector of a sleeve device and the other connector is configured to connect to a corresponding connector of a controller device.

Temperature management controllers and/or control circuitry, such as embodiments of the controllers 2150 in FIGS. 21A and 21B, may be configured to perform any type of functionality relating to the control of the devices 2100. For example, temperature management device control implemented in any of the embodiments of the present disclosure may include control related to any of the devices, systems, and/or processes disclosed in U.S. patent application Ser. No. 16/777,895, filed Jan. 31, 2020, and entitled REAL-TIME BODY TEMPERATURE MANAGEMENT, the disclosure of which is hereby expressly incorporated by reference in its entirety and constitutes part of the present disclosure.

Figure 22:
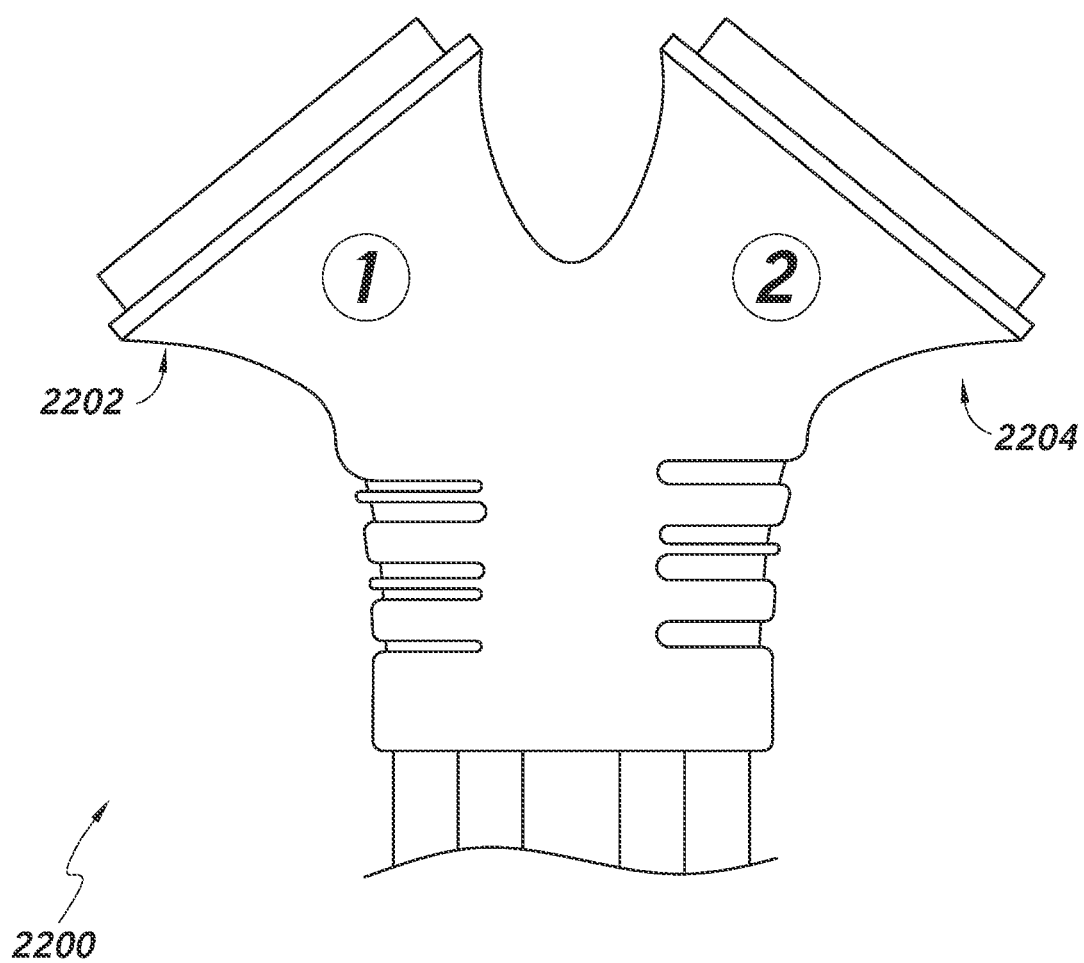
FIG. 22 illustrates a multi-channel interface for connecting one or more sleeves to a controller in accordance with one or more embodiments.

FIG. 22 illustrates a multi-channel interface 2200 for connecting one or more sleeves to a controller. The multi-channel interface 2200 may comprise at least two sections and may be configured to separate the heat delivery to a first channel 2202 and compression (e.g., fluid) delivery to a second channel 2204. In some embodiments, the interface 2200 may comprise at least two independent interface components, wherein each interface may be reserved for the same energy transferring channel types (e.g., heating or fluid) or a mix of both energy transferring channel types (e.g., heating and fluid). The multi-channel interface 2200 may comprise physical latching features to allow the patient contacting portion of the interface 2200 to be connected and disconnected with the sleeve. In some embodiments, the multi-channel interface 2200 may be an asymmetric interface and/or may include other physical and/or visual features designed to prevent the incorrect mating of the at least two separate portions of the interface. The interface 2200 may comprise physical design characteristics such that either fluid car heat transferring channels may be excluded in the final interface connection, as chosen by a user.

Temperature-Management Systems

Figure 23:
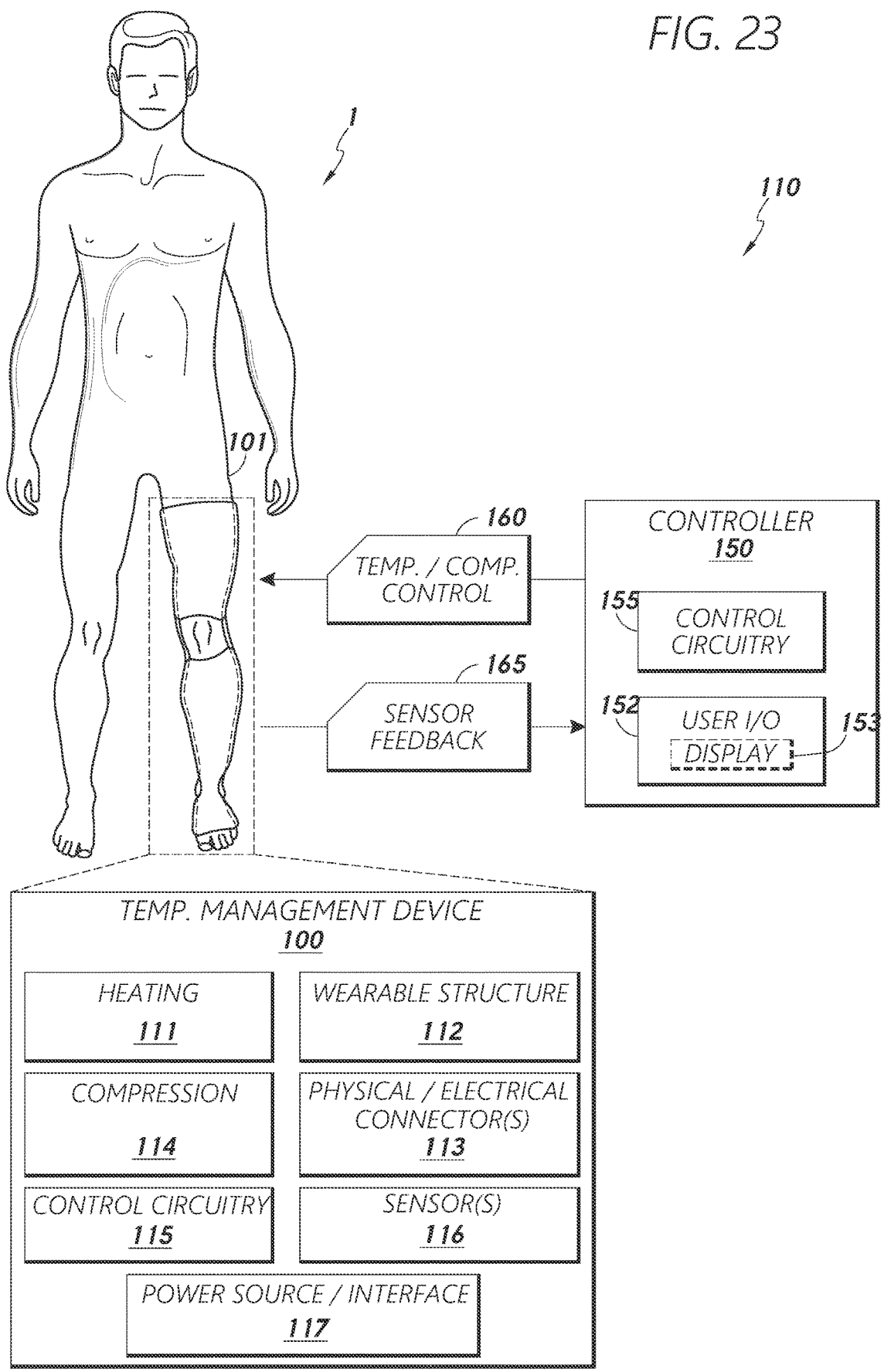
FIG. 23 provides front and side views of a sleeve configured to provide blood flow and/or compression therapy to a patient in accordance with some embodiments.

Disclosed solutions for managing temperature of a patient may be implemented in connection with a temperature-management system. FIG. 23 illustrates a system 10 for managing core temperature of a patient 1 in accordance with embodiments of the present disclosure. Although the description of FIG. 23 and other embodiments herein is generally presented in the context of temperature management, it should be understood that description of temperature-management and control herein is applicable to blood flow management solutions as well.

FIG. 23 shows a system 110 for managing temperature and/or blood flow in a patient 1 according to one or more embodiments. The patient 1 can have a temperature-management device 100 disposed on, for example, a limb and/or associated anatomy, of the patient 1. For example, the temperature-management device 100 can be disposed at least partially on the patient's leg 101. The temperature-management device 100 can include one or more sensors/sensor transducers 116, such as one or more microelectromechanical system (MEMS) devices, such as MEMS temperature sensors, or the like.

The system 110 can be used to deliver warming therapy and/or blood flow therapy to the patient 1 to help reduce blood stasis, deep vein thrombosis, and/or pulmonary emboli and/or to help regulate body temperature and/or optimize blood circulation. Warming and/or blood flow therapy can be used in the system 110 to help maintain normothermia and/or help return circulation to the patient's core, including the heart and lungs, from one or more extremities/limbs, such as the leg 101. Blood flow therapy and/or blood circulation therapy may be accomplished in a number of different ways, including but not limited to intermittent compression. For example, in some implementations, intermittent compression may be performed through the execution of circumferential compression of one or more limbs. Warming therapy may likewise be accomplished in a variety of different ways, including without limitation through the use of ultrasound, electrical, mechanical, chemical, radiative and/or convective energy.

The temperature-management device 100 may have any suitable or desirable shape, form, and/or configuration. For example, FIG. 23 provides a front view of an example temperature management sleeve device 100 configured to provide blood flow and/or compression therapy to a patient, which may represent an embodiment of a temperature-management device that may be used in connection with any of the embodiments disclosed herein. The term "sleeve" is used herein according to its plain and ordinary meaning and may refer to any device configured to be administered to one or more areas of a human body for delivery of heat and/or compression to the human body. For example, a "sleeve" may be a device configured to provide therapy to a limb or other body part at least in part through physical contact with the skin and/or other feature(s) of the body, wherein such physical contact provides therapy in and of itself or facilitates the provision of therapy through physically securing, positioning, or otherwise arranging one or more therapeutic devices, components, or features coupled to or otherwise associated with the sleeve. In some embodiments, the sleeve 100 may comprise a single continuous form or device and/or may be configured to apply therapy to a patient's thigh, knee, calf, and/or foot, and/or one or more other lower limb portions of a patient's body. The sleeve 100 may be applied to a patient's limb 101 (e.g., a leg, arm, and/or foot) and/or may be configured to deliver warming and/or to apply blood flow therapy to at least one area of the patient's limb 101. In some embodiments, the sleeve 100 may be configured to deliver heat to a majority of, or even the entire, limb 101 in conjunction with blood flow therapy. In some embodiments, the sleeve 100 may be configured to deliver heat to at least two different areas on the limb 101 while applying blood flow therapy between, adjacent to, and/or or overlapping the same areas.

In certain embodiments, the managing system 110 can comprise at least two subsystems, including a wearable subsystem or device 100 that includes the sensor(s) 116 (e.g., temperature sensor(s)), as well as control circuitry 115 comprising one or more microcontroller(s), discrete electronic component(s), and one or more power and/or data transmitter(s) (e.g., antennae). The temperature-management system 110 can further include a control subsystem including a controller module/device 150. The controller 150 may be configured to communicate data and/or power with the device 100 in any suitable or desirable manner, such as over a wired or wireless connection. For example, the control circuitry 155 may include certain connectivity circuitry including possibly a wireless transceiver that is electrically and/or communicatively coupled/couplable to the control circuitry 115 of the device 100.

In some embodiments, the temperature-management device 100 comprises one or more heating elements or mechanisms 111 (e.g., convective and/or conductive/radiative heating mechanism(s)), one or more flood-flow-inducing compression devices or mechanisms 114 (e.g., inflatable bladder(s)), one or more temperature sensors 116 (e.g., thermistors, surface temperature sensors, etc.) integrated with a functional wearable sleeve structure 112 including one or more sleeve portions. The temperature-management device 100 may further include one or more power sources or interfaces 117 as well as one or more electrical connectors for interfacing with a power source, fluid source, data source, and/or the like.

The sensor (s) 116 can comprise one or more MEMS sensors, optical sensors, piezoelectric sensors, electromagnetic sensors, strain sensors/gauges, accelerometers, gyroscopes, and/or other types of sensors, which can be disposed in a manner so as to be positioned on or in proximity to the skin of the patient 1 when the device 100 is worn by the patient 1. The sensor(s) 116 may be associated with the wearable structure 112, such that at least a portion thereof is contained within, or attached to, the wearable structure 112. The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with embedded at least partially within, or otherwise physically related to the second feature, element, component, device, or member, whether directly or indirectly. The sensor(s) 116 is/are electrically and/or communicatively coupled/couplable to the control circuitry 115, which may comprise one or more application-specific integrated circuit (ASIC) microcontrollers or chips.

In certain embodiments, the sensor (s) 116 can be configured to generate electrical signals that can be wirelessly transmitted to the controller 150. In order to perform such wireless data transmission, the temperature-management device 100 can include radio frequency (RF) transmission circuitry, such as a signal processing circuitry and an antenna. The control circuitry 115 of the temperature-management device 100 can comprise, for example, one or more chips or dies configured to perform some amount of processing on signals generated and/or transmitted using the device 100. However, due to size, cost, and/or other constraints, the temperature-management device 100 may not include independent processing capability in some embodiments.

In certain embodiments, the control circuitry of the temperature-management device 100 and/or the controller 150 includes some amount of volatile and/or non-volatile data storage. For example, such data storage can comprise solid-state memory an array of floating-gate transistors, or the like. The control circuitry may utilize data storage for storing sensed data collected over a period of time.

The control circuitry 115 of the temperature-management device 100 may be configured to receive sensor signals from the sensor(s) 116 (e.g., temperature sensor(s)) 116 and transmit sensor feedback data 165 to the controller 150. The controller 150 may in turn utilize the control circuitry 155 to generate certain control signals 160 and provide the same to the temperature-management device 100 to thereby direct operation thereof at least in part. The controller 150 may include certain user input/output (I/O) component(s) 152, such as one or more electronic displays 153, lights, buttons, and/or the like. The control circuitry 115, 155 of either or both of the device 100 and the controller 150 may be configured to implement any of the temperature-management functionality disclosed herein, including with respect to any of the operations, modules, elements, components, and/or other features associated with FIGS. 24-32 and described below. Although the controller 150 is shown in FIG. 23 as separate from the temperature-management device 100, it should be understood that any or all of the components and/or functionality described herein as associated with the controller 150 may be implemented as part of the temperature-management device 100 and any or all of the components and/or functionality described herein as associated with the temperature-management device 100 may be implemented as part of the controller 150. Examples of temperature-management devices and related/associated features that may be implemented in connection with any of the embodiments of the present disclosure are disclosed in U.S. patent application Ser. No. 16/777,894, filed on Jan. 31, 2020, and entitled PATIENT TEMPERATURE AND BLOOD FLOW MANAGEMENT, the disclosure of which is hereby expressly incorporated by reference and is considered part of the present disclosure.

Hypothermia Risk Determination

In some implementations, the present disclosure relates to systems, devices, and methods for combining risk assessment/determination for patient hypothermia with a temperature management/therapy sleeve to enable automated regulation of patient core body temperature and prevention of hypothermia may include. Such systems/devices may include, for example, control circuitry configured to operate and/or generate heating and/or compression control signals based on and/or in response to one or more of: temperature readings/data (e.g., set(s) of temperature-relevant inputs); hypothermia risk determinations or parameters (e.g., from a risk-weighted, self-adjusting computation process for determining a patient's risk for developing hypothermia); and certain control logic (e.g., proportional-integral-derivative—(PID) derived control algorithm(s) configured to integrate with the heat and/or intermittent compression elements of the temperature-management sleeve/device).

Various inputs and/or datatypes may be utilized in controlling a patient's temperature to avoid hypothermia. For example, in some embodiments temperature control may involve generating step function control signals to adjust temperature for patient warming. Through use of a risk-weighted/based computation/calculation process for controlling temperature, embodiments described herein may allow users to set a temperature management device and the device may be configured to automatically manage various patient-warming devices based on a variety of risk-related data structures/signals with or without additional user input.

In some embodiments, a patient's core temperature may be estimated or determined based at least in part on surface temperatures of the patient and/or ambient temperatures, such as may be determined based on signals from the sensor(s) 116 shown in FIG. 23. Such measured temperature(s) may provide an indication of how the patient's temperature may change over time. For example, surface temperatures may be utilized in determining, by control circuitry, a time value parameter indicating how long a period of time is expected until a patient may be in a range of hypothermia given current (e.g., sensor-based) conditions.

Additional parameters on which temperature-management signals may be based include parameters related to administration of anesthesia. When anesthesia is administered, a patient's brain may lose the ability to manage its body temperature to some degree. For example, in some situations, an anesthetized patient may experience dilated blood vessels even when the patient's body temperature is relatively low. When the patient's heart then pumps relatively cold blood from the patient's extremities, the patient's core temperature can be further lowered. In some embodiments, a clinician may provide input to a system (e.g., using the user 110 component(s) 152 shown in FIG. 23 and described above) indicating when anesthesia is administered. In some embodiments, a system may be configured to automatically determine that anesthesia has been administered. For example, given that heart rate generally drops with anesthesia, in some embodiments, a temperature-management system may be configured to determine that anesthesia has been administered automatically when it is determined (and/or in response to such determination) that a patient's heart rate has dropped below a predetermined threshold level or by a predetermined amount. Various inputs may be utilized in predicting a patient's future body temperature.

Determining a patient's risk for developing hypothermia may be based at least in part on various primary and/or secondary inputs/parameters (e.g., generated and/or stored parameter values, flags, or the like). Characterization as primary and secondary inputs/parameters can be further segmented/parsed as metadata types and/or data received and sent to sensors. In some embodiments, data from primary inputs may be utilized by the system for effective hypothermia prediction and prevention. That is, as used herein, "primary inputs" may refer to inputs that, according to some embodiments, are used to determine temperature control signals for managing patient temperature.

Figure 24:
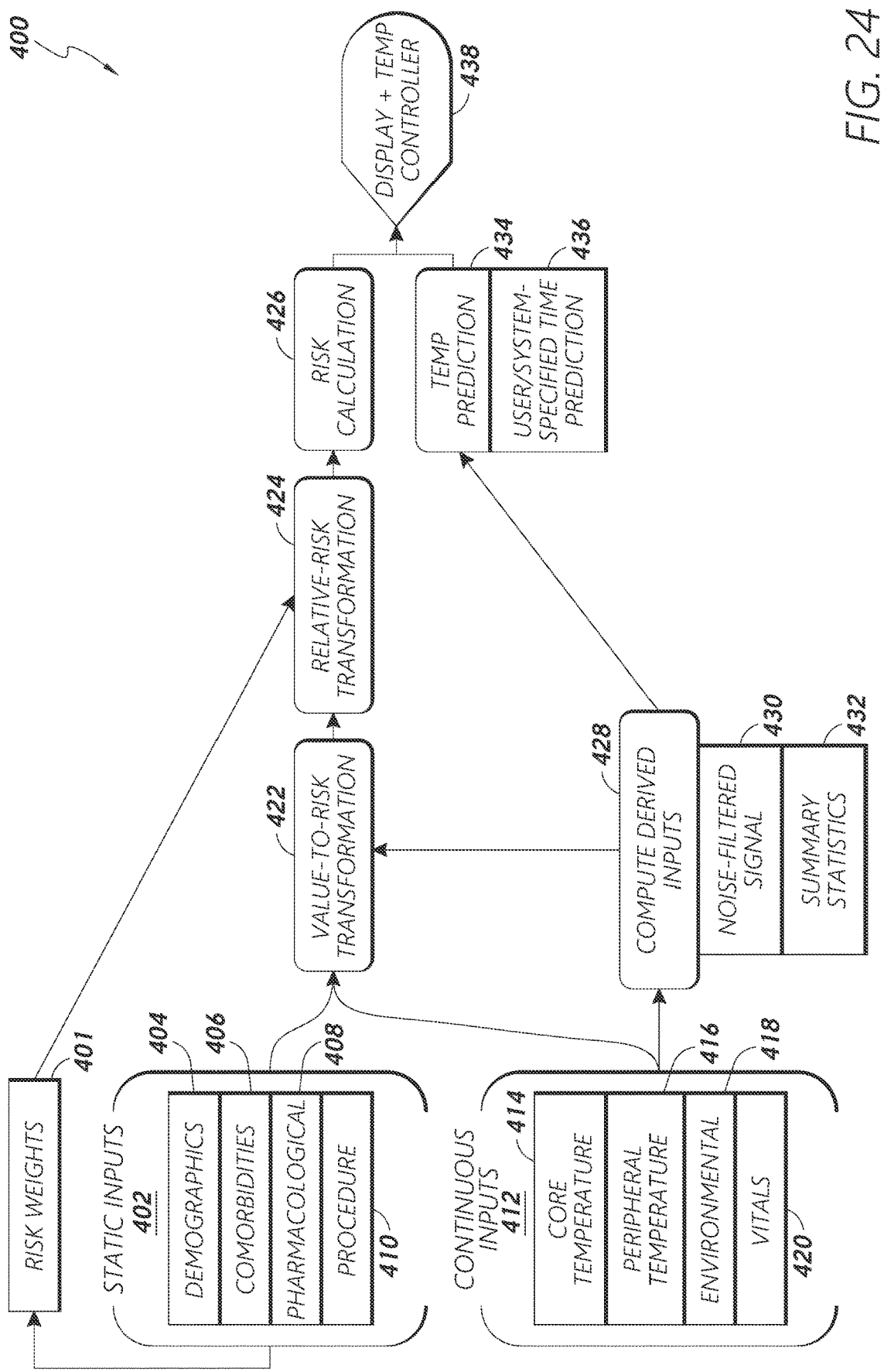
FIG. 24 provides an example risk-weighted self-adjusting calculation process for determining a patient's hypothermia risk in accordance with some embodiments.

In some embodiments, certain data inputs/parameters used to monitor a patient and/or dynamically manage temperature conditions for the patient are illustrated in FIG. 24, which provides an example risk-weighted self-adjusting temperature-management process 400. The process 400 may be implemented in whole or in part by certain control circuitry of a temperature-management system, such as by control circuitry associated with one or both of a temperature-management controller and a temperature-management device (e.g., wearable sleeve device), as may be similar in certain respects to corresponding components in the system 110 of FIG. 23, described in detail above. In some embodiments the process 400 can be implemented to determine a patient's hypothermia risk. Such data inputs/parameters may include, for example, static inputs 402 (e.g., procedure data 410, including procedure type and/or length) and continuous and/or time-varying inputs/parameters 412 from sensors, which may include, for example, stored and/or generated values indicating time-to-induction. (e.g., of anesthesia) and/or peripheral temperature readings 416 (e.g., supplied by the control circuitry of the temperature-management system).

Certain types of parameter data values may improve the accuracy of hypothermia risk determination while not being necessary for hypothermia risk determination. Such inputs/parameters may be referred to as "secondary" inputs/parameters. Although referred to below as "secondary" inputs/parameters, it should be understood that such parameters and/or associated values may be of any suitable or desirable type. In some implementations, the availability and/or inclusion of such secondary inputs may improve the accuracy of the calculation and/or temperature-management process 400, and by extension, the efficacy of prevention of hypothermia. Secondary static inputs 402 (e.g., metadata) may be sampled or determined/recorded at least once, such as prior to the relevant medical operation or during another period, and/or may not be sampled intraoperatively. Secondary static inputs 402 may include, for example, demographic data. 404 (e.g., age, body mass index (BMI), and/or sex of the patient), comorbidity status data 406 (e.g., American Society of Anesthesiologists (AS) grade and/or any of various risk factors including cancer and/or other disease risk, patient smoking habits, etc.), pharmacological agents 408 (e.g., premedication, anesthesia, and/or analgesia), procedure/timing-related data 410, and/or the like.

Secondary time-varying/dynamic parameter/input data 412 may be provided by and/or determined based on signals generated by sensors that may be a part of a temperature-management system. Secondary time-varying/dynamic parameter/input data 412 may include, for example, peripheral temperature 416 readings and/or environmental information 418 (e.g., temperature of the post-anesthesia care unit (PACU) and/or operating room, etc.). In some implementations, data collected in real time by one or more monitor devices and/or associated sensor(s) (e.g., a Philips anesthesia monitor) may be accessed intermittently, sporadically, periodically, on a delayed basis, and/or intraoperatively, wherein such data may serve as a basis for temperature management and/or hypothermia risk determination by system control circuitry. Types of time-varying data that may be used by control circuitry for temperature control and/or hypothermia risk determination may include, for example, core (and/or peripheral) temperature readings 414 (e.g., current value, rate of change, etc.), non-temperature vital signals 420 (e.g., heart rate, blood pressure, carbon dioxide level/values, oxygen level/values, and/or respiratory rate), and environmental information 418 (e.g., room temperature, use of heating measures, under-warming blanket, and/or intravenous line).

One or more parameters/inputs used in temperature-management process in accordance with aspects of the present disclosure may be assigned a risk weight 401. For example, a risk weight 401 may indicate how significant a given parameter/input may be in determining a patient's total risk of hypothermia. For example, while a patient's core temperature 414 and demographic information 404 (e.g., age) may both be parameters/inputs used in determining the patient's risk of hypothermia, the core temperature 414 of the patient may be relatively more determinative of risk than certain of the demographic information 404 and may accordingly be assigned a higher weighting. In some embodiments, a risk weight 401 may be time-varying. For example, the onset of anesthesia may be weighted with relatively greater risk of causing hypothermia immediately following administration of the anesthesia. In comparison to a relatively lower risk towards the end of a surgical procedure. Parameter-weight correspondence information may be stored in one or more data storage devices of the system and utilized by control circuitry to drive temperature management control signal generation and/or provision. In some embodiments, the one or more data storage devices may be configured to store personalized and/or otherwise associated risk profiles. For example, a patient-specific risk profile identifying particular risk weight values and/or risk factors may be associated with a particular patient.

The process 400 may involve one or more operations relating to determination of one or more value-to-risk transformations/determinations 422. For example, value-to-risk transformation/determination 422 may involve accessing stored data (e.g., lookup chart or other data structure(s)/type(s) stored in non-volatile or volatile data storage of the temperature-management system) to correlate measured parameter/input data to stored risk data. In some embodiments, risk data may provide a value between 0 and 1 to indicate how predictive/determinative each input may be of hypothermia risk and/or other issue(s).

In some embodiments, the temperature-management process 400 may further involve a relative-risk determination/transformation 424, which may be based at least in part on risk weight data 401 to indicate the relative risks of each parameter/input value relative to one or more other parameters/inputs. The relative-risk transformation 424 may be based at least in part on one or more of the static and/or dynamic parameters/inputs associated with the process 400. For example, demographic data 404 may be associated with a value-to-risk transformation 422 value of 0.7 (i.e., a score of 7 out of 10, with 10 being the highest risk of hypothermia). If demographic data 404 is the only parameter/input on which hypothermia risk determination is based, the patient may be determined to be associated with a risk value 426 of 0.7. In other words, demographic data 404 may be wholly determinative of the risk value 426 if demographic data 404 is the only parameter/input considered (or another parameter if such parameter is the only parameter considered). However, if other parameters/inputs are considered that have for example, a relatively higher weighting than demographic data 404, the demographic data 404 may have a relatively low effect on the risk value 426. The risk value 426 may represent various determinations/calculations which may be performed based on any of the various parameter/input and/or transformations in the process 400.

In some embodiments, the process 400 may involve determining various derived parameters/inputs 428. Derived parameters/inputs 428 may include various computations to indicate how a patient's temperature may change over a period of time. In some embodiments, derived parameters/inputs 428 may be determined based at least in part on past measurement(s) (including, e.g., noise-filtered signals 430 indicative of patient temperature values) and/or summary statistics 432.

Static parameters/inputs 402 and/or continuous parameters/inputs 412 may be utilized in the risk calculation 426. Static parameters/inputs 402 may be utilized with respect to hypothermia risk determination 426 prior to onset of temperature management/therapy. In some embodiments, parameters/inputs may be input/entered by a user via manual entry (e.g., by clinical staff) and/or electronically/automatically through integration with data records (e.g., patient health record (PHR) systems and/or 3rd party data-integration vendor(s) of said data records).

Dynamic parameters/inputs 412 may be provided by various devices of the temperature-management system (e.g., sleeve(s)) and/or from other sources. The system may be configured to collect peripheral temperature 416, environmental temperature 418, and/or core temperature 414 data. Vital sign data 420 and/or other external data may be collected from various data records, for example.

In some embodiments, various dynamic parameters/inputs 412 may be pre-processed by the system in order to generate noise-filtered signals 430 and/or summary statistics 432. Noise-filtered signals 430 may eliminate signal artifacts (e.g., to provide noise smoothing). Summary statistics 432 may comprise aggregated statistics of various measurements (e.g., baseline, rate of change, future value prediction) that may be required or desired/helpful for the risk value 426 determination. Summarizing statistics 432 can include, for example, signal noise smoothing (e.g., filtering to remove noise artifacts from a signal), signal baseline average of signals over time), rate-of-change estimations derivative of the signal over time), and/or value, predictions (e.g., use rate-of-change to project future state/temperature).

A patient temperature prediction 434 may be determined based at least in part on one or more derived parameters/inputs 428. In some embodiments, the risk value 426 may be based at least in part on the temperature prediction 434 and/or one or more user- and/or system-specific predictions 426 indicating how long until the patient may reach the predicted temperature, which may be specified in minutes or any other unit of time. The risk calculation 426, temperature prediction 434, and/or time prediction 426 may be displayed in a display 438 and/or may be used be a controller to adjust and/or maintain heating at one or more sleeves administered to a patient.

Figure 25:
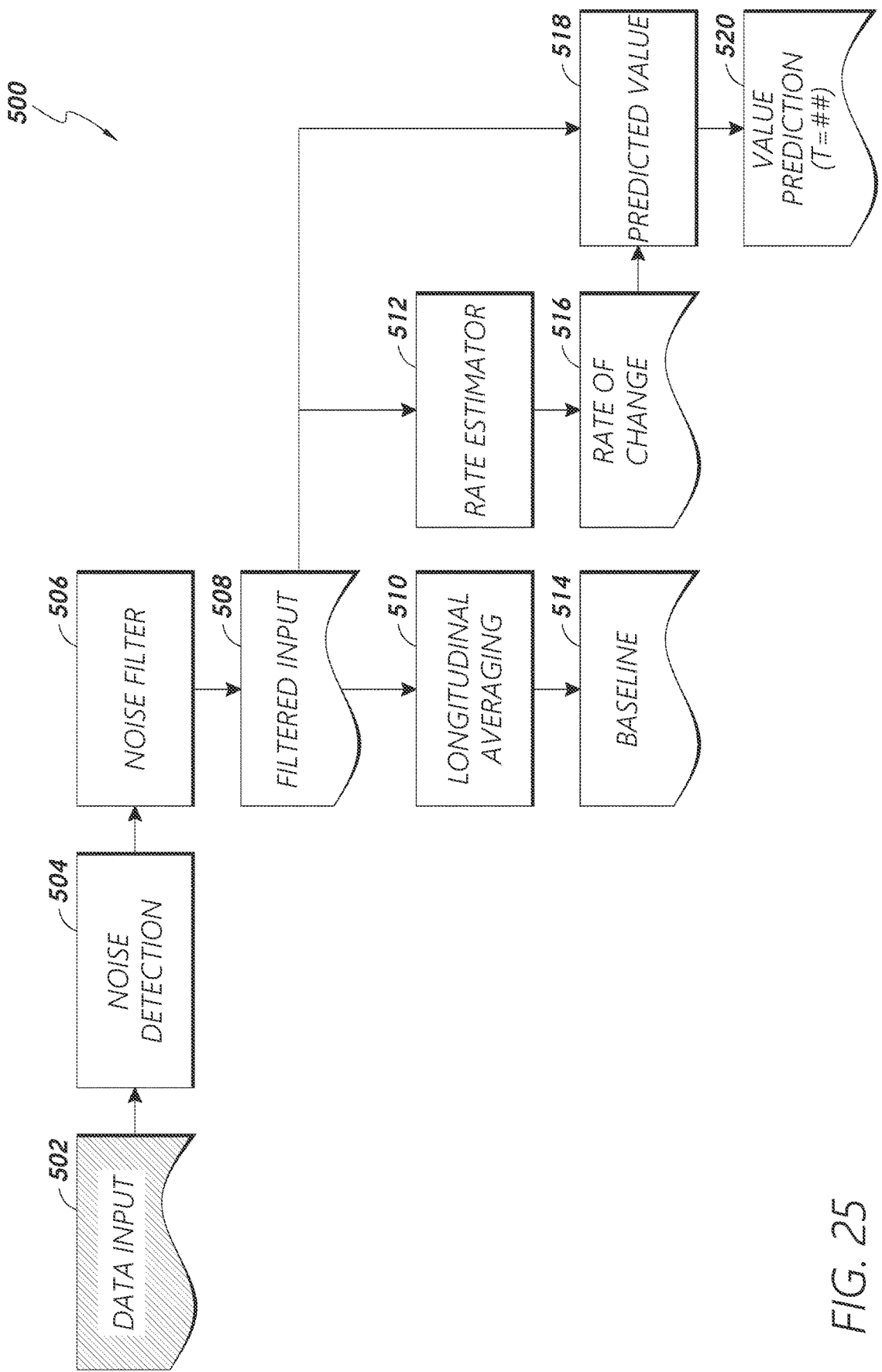
FIG. 25 illustrates a process for predicting a patient's future body temperature value given a raw/primary data input in accordance with some embodiments.

FIG. 25 illustrates a process 500 for predicting a patient's future body temperature value 520 given certain data input parameter(s) 502. The various functional modules and/or features relating to FIG. 25 and the process 500 can be performed at least in part by control circuitry of a temperature management device (e.g., wearable sleeve device) and/or a temperature management controller. Furthermore, the disclosed modules and features of FIG. 25 can represent implementation aspects relating to certain blocks of the process 400 of FIG. 24. The data input 502 may be a static input (e.g., a core temperature sample, as reported by various sensors such as esophageal, nasopharyngeal, bladder, tympanic, skin and/or other sensors) or a dynamic input. The process 500 may involve performing noise detection 504 and/or noise filtering 506 to generate a filtered input 508 (i.e., a noise-filtered signal). The filtered input 508 may represent a derived input and/or smoothed version of the data input 502. The process 500 may further involve generating rate-of-change value(s) 512 (e.g., in degC/min) and/or predicted temperature value(s) 518 (e.g., in Celsius) relating to a future time using the filtered input 508. In some embodiments, the rate-of-change value 516 may be computed through use of a rate-of-change estimator 512. The process 500 may further involve calculating a baseline metric 514 by evaluating a longitudinal averaging 510 over a period of time (e.g., a median temperature value as sampled over the last four hours). In some embodiments, the process 500 may involve generating secondary inputs (e.g., filtered inputs 508 rate-of-change values 516, baseline metrics 514, etc.) using various time-varying inputs/measurements including temperature, heart rate, oxygen concentration, and/or various vital signals.

Signal noise smoothing can be achieved through implementation of one or more filters (e.g., Kalman filter, or the like) applied to current and/or previous readings of a signal. The filter(s) may be configured to act as a recursive estimator which can compare the current (measured) value to the system's estimation (prediction) for the current value to identify and eliminate noise in the signal.

In some embodiments, a simple filter (e.g., a finite impulse response filter (FIR)) may be applied to various measurements. Filter coefficients may be designed to eliminate high frequency data from signals. A moving average (mean) filter may be utilized, in which a given number of measurements may be assigned the same weight in the filter.

The baseline 514 of a signal can represent a running average (mean) of the signal over a period of time (e.g., collected over the past 3 hours). In some embodiments, the baseline 514 can be computed on the smoothed signal to minimize influence of noise artifacts.

The rate-of-change 516 of a signal can represent the velocity of the signal over time. In some embodiments, the rate-of-change 516 can be computed from a rate estimator functional module 512 by comparing the current smoothed/filtered value 508 (x_k) to the next estimated value (x_klk). The formula may be the following:

$$dx)k/dt = [(x\_klk) - (x\_k)]/[\text{sampling time}] \quad (1)$$

In some embodiments, the rate-of-change 516 may be computed through application of a Savitzky-Golay filter. The Savitzky-Golay algorithm applies an FIR to the most recent n-samples of data to estimate the derivative over the observed period of time (n samples). This computed derivative may be less reactive to rapid swings when compared to other estimators (e.g., a Kalman estimator).

The predicted value 518 for a signal can be computed by summation of the current smoothed/filtered signal 508 (x_k) and the product of the rate-of-change 516 (dx_k/dt) and the amount of time to project into the future (e.g., 30 min). For example, the prediction calculation 520 can be the following:

$$\text{Prediction}\_k = x\_k + (30 * dx \; k/dt) \quad (2)$$

The filtered input 508, baseline 514, rate-of-change 516, and/or value prediction 520 may each represent derived inputs of the data input 502.

Risk transformations may represent conversions of real signals (e.g., temperature values) into a normalized risk value (e.g., 0-1). Examples of risk transformations can relate to the use of diagnostic tools like hospital scorecards in health care environments. Core temperature may be a direct risk input for hypothermia (by definition, hypothermia is defined by core temperature below 36° C.). In situations where the system has a dynamic/continuous reading of core temperature, both the current temperature and the trend in temperatures may have significant weight in the risk determination. For example, current temperature values below 36° C., between 36° C. and 37° C., and above 37° C. may correlate to risk transformation values of 10, 5, and 1, respectively. Rate-of-change 516 values in ° C./min of −0.01, −0.03, and −0.05 may correlate to risk transformation values of 1, 2, and 3, respectively, for example. Although certain risk values are disclosed herein, it should be understood that any types of risk values or scales may be implemented in embodiments of the present disclosure.

Peripheral patient temperature (e.g., skin surface temperature) may be an indirect predictor of hypothermia. Therefore, peripheral temperature values may serve as a non-zero-weighted parameter for hypothermia risk determination. For example, peripheral temperature may be associated with a risk value that is less than a risk value associated with core temperature. A similar risk index may be applied for any individual patient temperature readings. The individual risk values may be weighted relative to each other.

Risk-associated weighting of each parameter may be determined/translated based at least in part on pre-known clinically significant odds ratio when comparing patient populations. For example, patient ages of less than 15 years, between 15 and 64 years, and over 64 years (or any other age ranges) may be correlated with relative risk values of, for example, 1.00, 1.67, and 2.62, respectively, or any other values. American Society of Anesthesiologists (ASA) ratings of 1, 2, 3, 4, and 5 may correlate to relative risk values of, for example, 1, 1.8, 1.8, 3.2, and 19.9, respectively, or any other values. Body fat and/or body mass index (BMI) patient levels of n % may correlate to a relative risk value of 1+0.025*n, or any other relationship/values. Preoperative temperature values in C of less than 36 and greater than or equal to 36 may correlate to relative risk values of 1 and 0.3, respectively, or any other temperature ranges and/or risk values. Surgery magnitude designations of "minor," "intermediate," and "major" may correlate to relative risk values of 1, 5, and 10, respectively, or any other values or designations. Surgery duration values in hours of less than or equal to 2 and greater than 2 (or any other time periods) may correlate to relative risk values of 1.0 and 4.5, respectively, or any other values. Anesthesia types of regional, general, and combined (or any other type designations) may correlate to relative risk values of 0.22, 1, and 2.77, respectively, or any other values.

Various risk factors may be collected and determined/transformed from a measured (or derived) value (e.g., degC) to a risk metric with a value between 0 and 1. However, individual risk factors can generally have different impact on a patient's risk for hypothermia. For example, the environmental temperature (e.g., 25 C) may indicate a moderate risk (e.g., 0.75) for hypothermia, but relative impact of the environmental temperature may be small when compared to the patient's actual core body temperature (e.g., 36.7 C, translating to a risk metric of 0.3, for example). In this case, the relative weight of environmental temperature may be much smaller than the core body temperature reading. The relative risk may be calculated as a product of a given risk metric and the relative weight of the given risk metric.

The relative weights assigned to each metric may be dynamically configurable and/or may change depending on a number of factors. For example, the weights may be modified based on static inputs, such as patient demographic and operating mode (e.g., pre-op vs. Intra-op vs. post-op) data. For example, an older patient with elevated CVS risk (e.g., due to smoking) could have a different set of weights applied as compared to a 20-year old, patient with no additional demographic risk factors. Additional factors may include the quantity of anesthesia.

In some embodiments, risk index weights may shift based on operating mode as well as with patient/procedure demographic information. For example, a patient with cardiovascular system complications may have elevated blood pressure. The contribution of the cardiovascular system and/or blood pressure complications towards hypothermia risk in the patient may be lower than for a patient who has no heart disease and/or nominally normal blood pressure.

Some embodiments may involve performing a weighted and/or normalized summation on some or all available risk metrics. Relative weights may be preconfigured and/or may be modified based on hospital protocol, procedure type, and/or physician decision. An overall risk value for a patient may be calculated by dividing a summation of all relative risk values for a given metric by a summation of all metric-specific coefficients/weights using a relative weighting. The resulting overall risk value may be a value between 0-1 and/or may reflect the system's determination of a patient's risk for hypothermia. Such determination may be generated/performed at least in part by control circuitry of the temperature-management system as described herein.

Patient peripheral (e.g., limb) temperatures may be expected to be lower than the core body temperature. Some embodiments may involve implementing a model that accounts at least in part for the transfer of heat through lower limb tissue and vasculature to translate measured peripheral temperatures into estimates of tissue temperature (e.g., by depth and/or core body temperature).

Estimated core body temperature may be used in place of direct core temperature measurements when direct core temperature measurements may not be available. Furthermore, actual and/or estimated tissue temperatures may be used by the system to monitor patient burn risk, particularly in situations where an external heat source is applied to a peripheral limb. For example, tissue temperature data may be generated and/or provided by one or more temperature sensors (e.g., thermistors) integrated with a wearable sleeve device in accordance with aspects of the present disclosure.

In some embodiments, a patient's future core temperature may be predicted approximately thirty minutes, or other amount of time, in advance using one or more of the following parameters: the patient's current temperature, a temperature rate-of-change, and/or anesthesia depth. For example, the future temperature may be determined based at least in part on a sum of the current temperature, the temperature rate-of-change, and an anesthesia modifier factoring in the concentration of anesthesia.

In some embodiments, outputs of a risk value, determination may be used as inputs for a controller (e.g., the controller 150 of FIG. 23) to adjust the amount of heat transferred into the patient's body. In some implementations, heat transfer may be dually controlled by adjusting the temperature of heating element(s)/mechanism(s) associated with a wearable sleeve device disposed on the patient and/or the rate of venous return of implemented by compression element(s)/mechanism(s) associated with the sleeve device (e.g., adjusting rate-of-flow and/or inflation period/cycle for inflatable bladder compression). In certain situations, the temperature-management controller may be configured to control heating and compression elements together, treating them as a single mechanism/transducer. For example, at therapy initiation (e.g., device start), the device may rapidly reach the target temperatures and pressure.

The temperature-management controller may be configured to operate each heating element (e.g., 2 per limb for each of the sole of the food and the hack of the knee/popliteal fossa) independently while controlling the compression elements (e.g., 1 per limb for a calf portion of the sleeve device) together. Independent heating element control may advantageously allow for relatively finer tuning of heat transfer to the body. In some embodiments, a temperature-management controller may be configured to alternate, heating between, for example, foot and popliteal fossa locations to support higher device temperatures (e.g., increased heat transfer) without increasing tissue burn risk.

Figure 26:
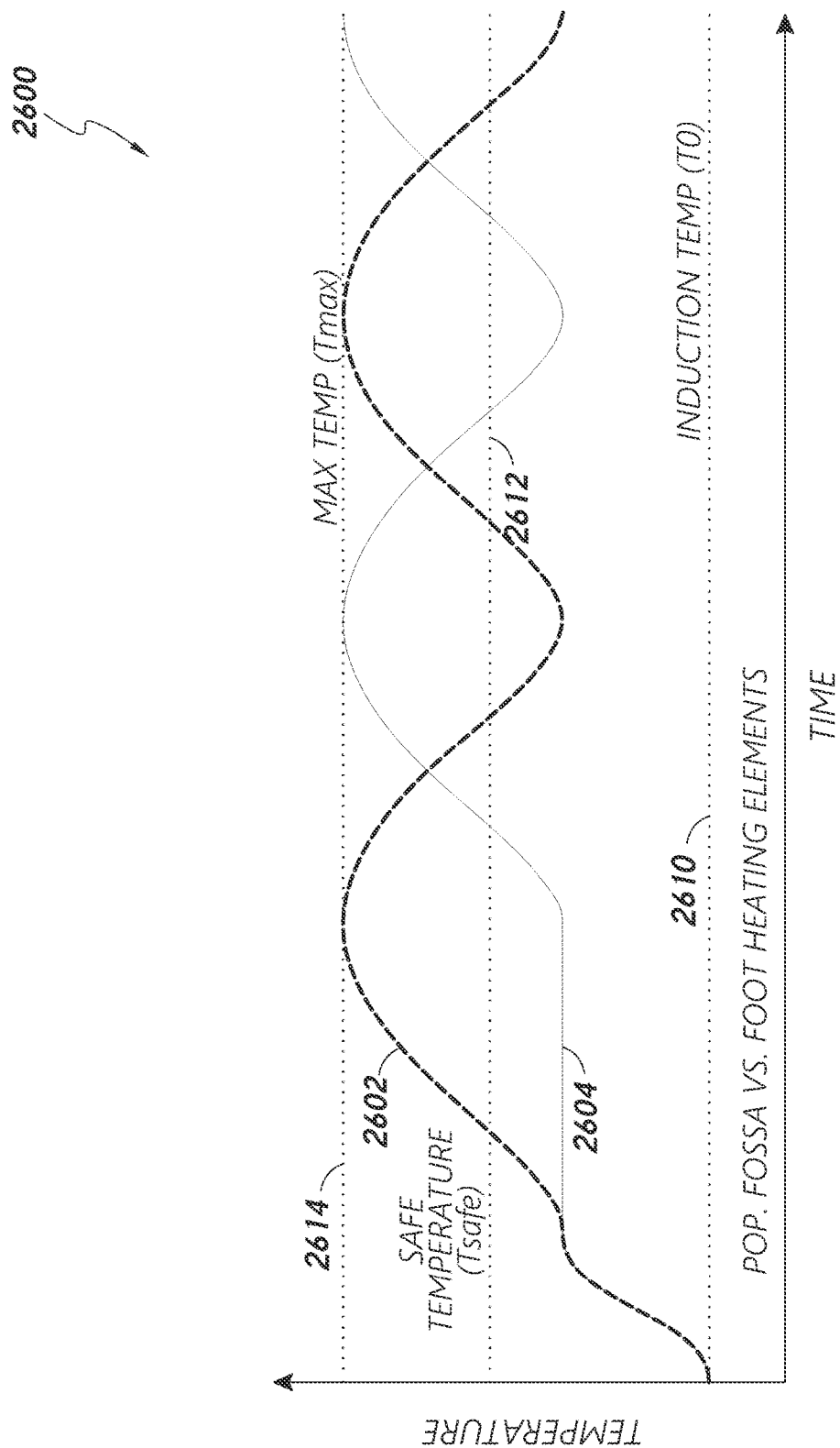
FIG. 26 provides a graph illustrating temperature values at different moments of time in accordance with some embodiments.

FIG. 26 provides a graph 2600 illustrating, temperature values at different moments of time. A first line 2602 of the graph 2600 may represent temperature values at a first target area of a patient (e.g., the popliteal fossa) and a second line 2604 may represent temperature values at a second target area (e.g., the sole of the foot). Temperature values may vary between an induction temperature value 2610 and a maximum temperature value 2614. A certain temperature value, or range of temperature values, between the induction temperature value 2610 and the maximum temperature value 2614 may be considered safe and/or desired temperature value(s) 2612. In some embodiments, the maximum temperature value 2614 may correspond to a temperature at which there may be a risk of burning at the target area. For example, the maximum temperature 2614 may represent a temperature beyond which the risk of burn is greater than a predetermined threshold. As temperature at one of the target areas increases to above the safe temperature value 2612 and/or at or near the maximum temperature value 2614, the temperature may be decreased to prevent burning. Similarly, as the temperature drops below the safe temperature value 2612, the temperature may be increased. That is, embodiments of the present disclosure provide for the intermittent heating of the sole of the foot and the popliteal fossa in a back-and-forth manner to provide improved heating while operating within safe temperature ranges. For example, the heating element(s) associated with the foot and the popliteal fossa may be operated in an at least partially alternating manner, wherein the maximum heating level for the temperature-management process/system is not implemented for one of the foot and popliteal fossa during a time in which the maximum heating level is implemented for the other. In some embodiments, temperature may be controlled manually and/or at least partially automatically/electronically using the temperature-management controller/control circuitry.

Figure 27:
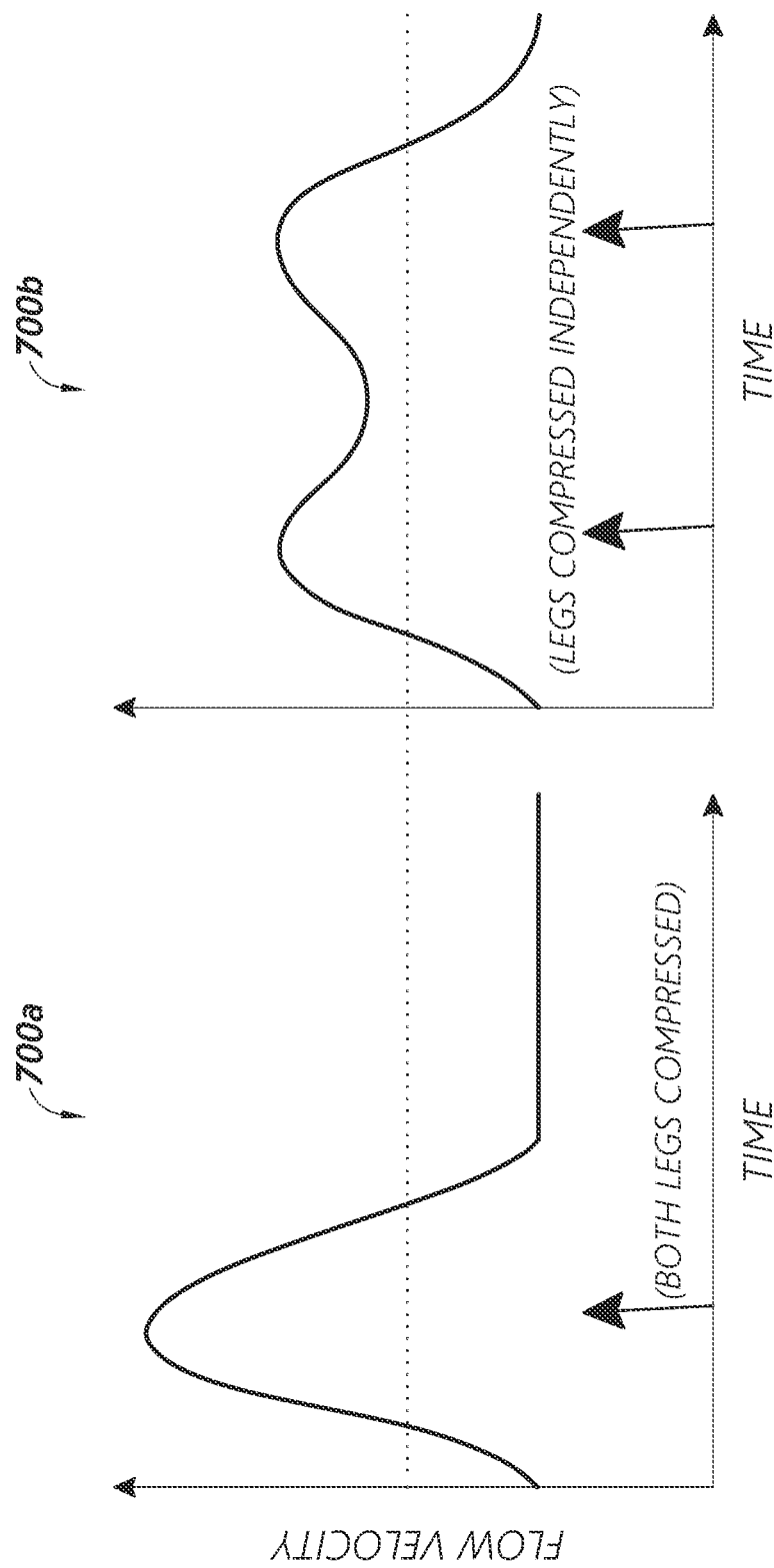
FIG. 27 provides graphs illustrating venous flow velocity over time in accordance with some embodiments.

In some embodiments, a temperature-management controller may be configured to control each heating dement (e.g., 2 per limb) and/or compression element (e.g., 1 per limb) independently. FIG. 27 provides graphs illustrating venous flow velocity over time for multiple-limb temperature management solutions. In some embodiments, a temperature-management system may comprise multiple sleeves/sleeve components (e.g., each at a different limb of a patient) and/or a sleeve configured to compress multiple limbs of the patient. A first graph 700a represents flow velocity values for a system configured to compress multiple (e.g., two) limbs of a patient together (i.e., using the same control signals for both sleeve devices). As shown in FIG. 27, the flow velocity when both limbs are compressed may spike and drop dramatically. The second graph 700b illustrates venous flow velocity for a system in which multiple limbs are compressed independently of each other. For example, each sleeve of multiple sleeves may be controlled independently to provide enhanced therapy associated with venous return. As shown in the second graph 700b, venous flow velocity values may reduce slightly after an initial spike associated with compression of one limb, but the velocity values may be maintained more effectively than in the system shown in the first graph 700a as they rise again in connection with compression of the other limb. In some embodiments, a system may be configured to alternate compression between each leg of a patient to improve the venous return profile.

Figure 28A:
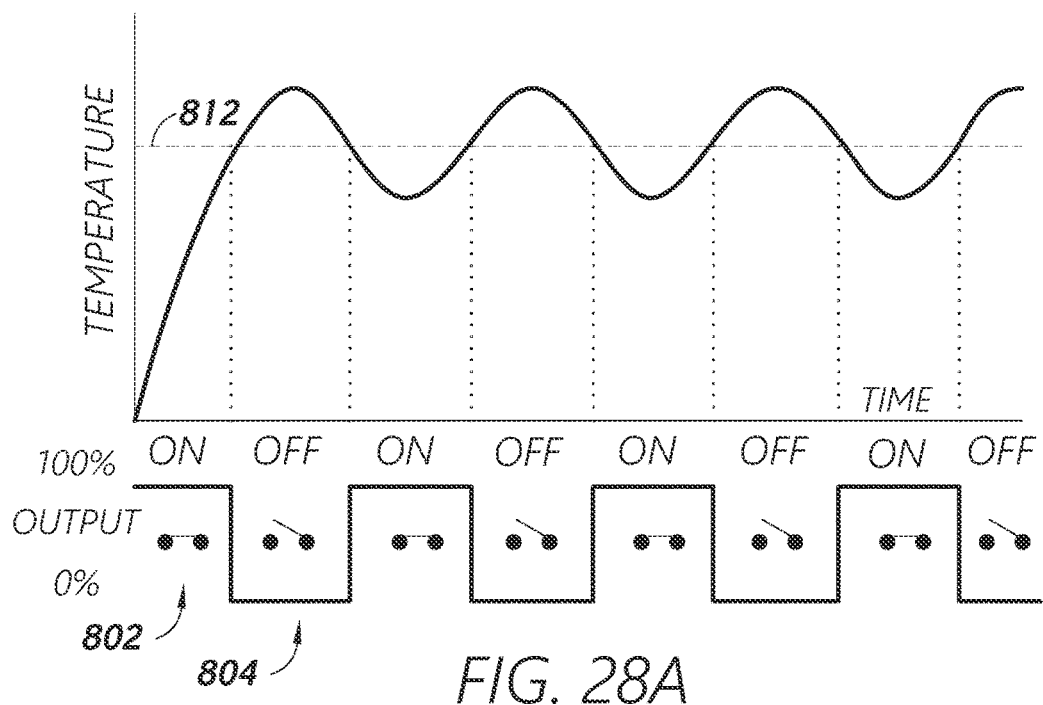
FIGS. 28A and 28B illustrate on-off cycles which may be performed at a controller for one or more sleeves configured to warm and/or compress one or more target areas of a patient's body in accordance with some embodiments.
Figure 28B:
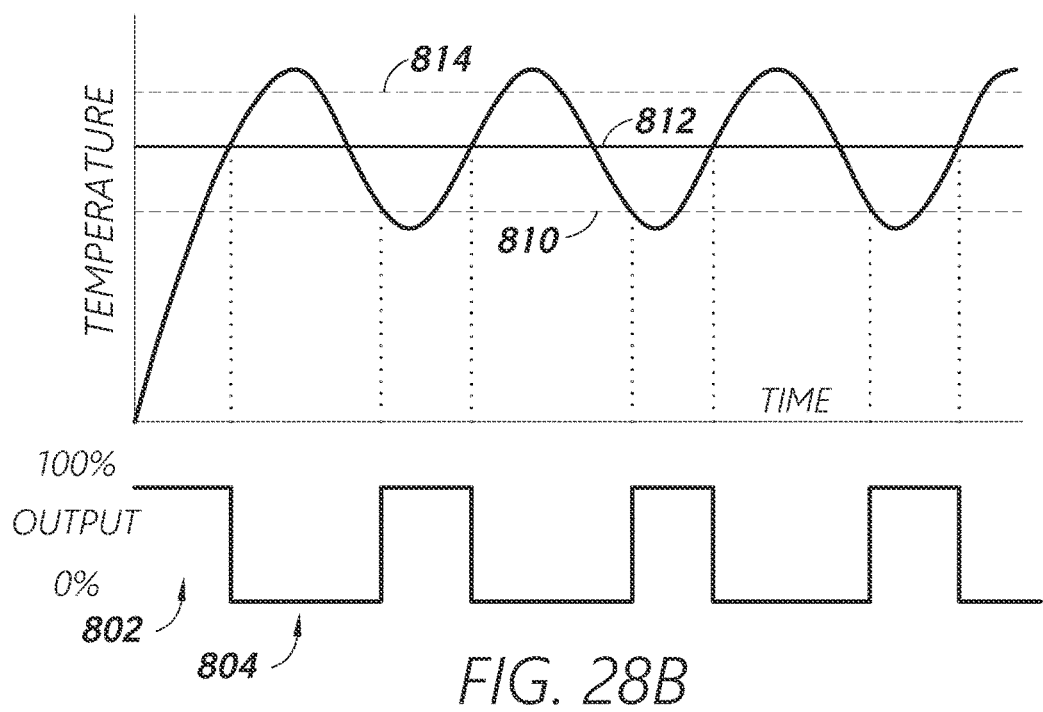

FIGS. 28A and 28B illustrate on-off cycles performed at a temperature-management controller for one or more sleeves configured to warm and/or compress one or more target areas of a patient's body. In some embodiments, the controller may utilize a process (e.g., a damped proportional-integral-derivative (PID) control algorithm) to control core body temperature. The process may be designed to overshoot and/or undershoot issues of a simple treat-to-target and/or treat-to-range algorithm. As shown in FIGS. 28A and 28B, a controller may be configured to enter an ON state 802 when temperature is above a safe temperature value 812 and/or at or near a maximum temperature value 814. Similarly, the controller may be configured to enter an OFF state 804 when the temperature is below the safe temperature value 812 and/or at or near a minimum temperature value 810. The pulse width of the ON-cycle relative to the OFF-cycle can determine the amount heating and/or blood flow augmentation implemented. In some embodiments, the controller may be configured to apply heat when the patient is hypothermic and/or predicted to become hypothermic based at least in part on various calculation processes described herein.

Figure 29:
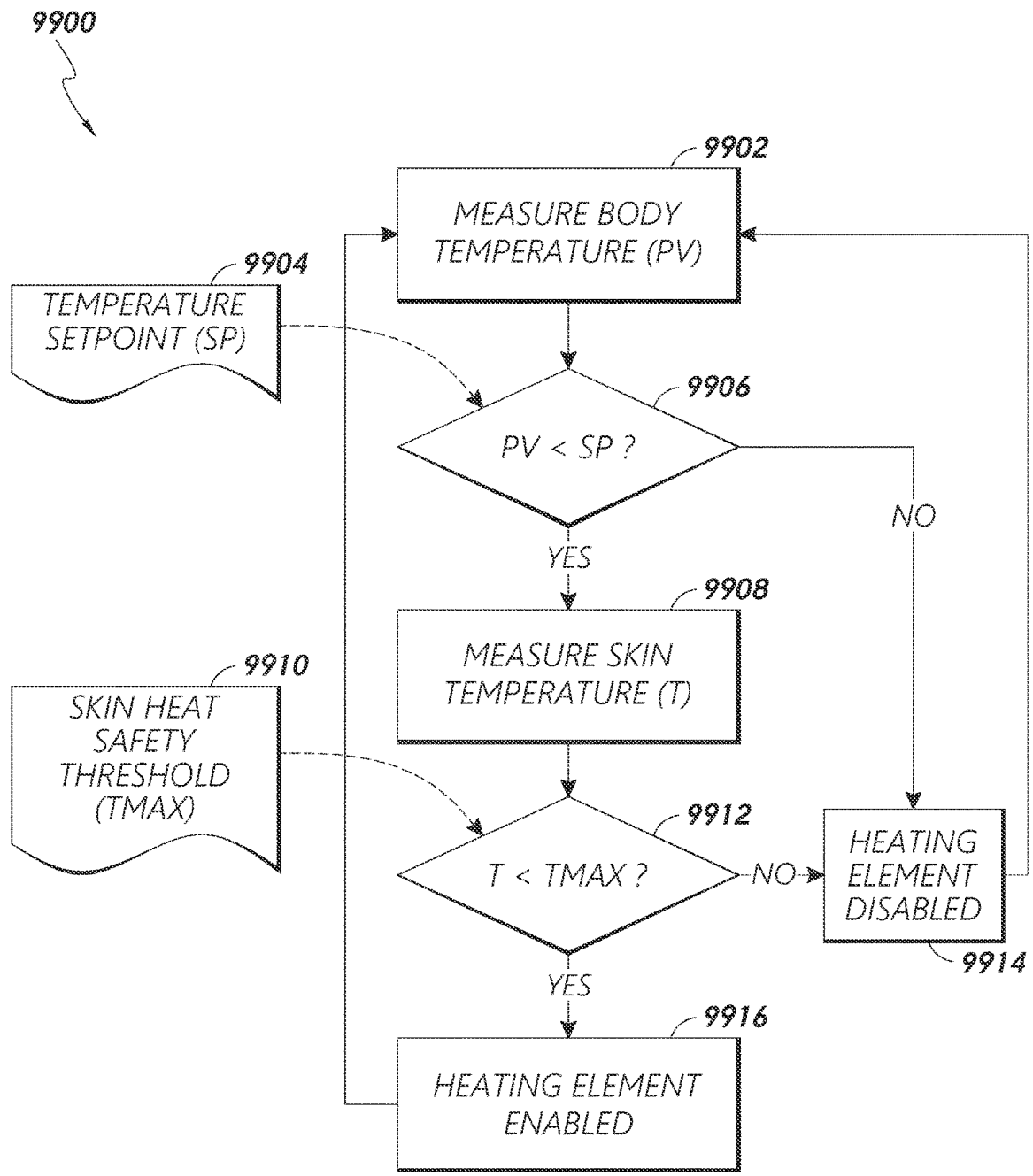
FIG. 29 provides a process for enabling heating elements at sleeve devices providing heat to a patient in accordance with some embodiments.

FIG. 29 provides a process 9900 for enabling/activating heating elements at sleeve devices providing heat to a patient. The process 9900 may be implemented in whole or in part by certain control circuitry of a temperature-management system, such as by control circuitry associated with one or both of a temperature-management controller and a temperature-management device (e.g., wearable sleeve device), as may be similar in certain respects to corresponding components in the system 110 of FIG. 23, described in detail above.

At block 9902, the process 9900 involves measuring and/or estimating a present value (PV) of the patient's body temperature. For example, the measured/estimated temperature may be directly-measured core temperature or may be estimated temperature based on measured peripheral (e.g., skin) temperature. In some embodiments, the temperature PV may be measured using one or more sensors attached to and/or otherwise used in conjunction with a sleeve administered to, or otherwise disposed on, the patient.

At block 9904, the process 9900 involves determining a temperature set point (SP) (e.g., target temperature value). In some embodiments, different areas of a patient's body may have different SP values. The temperature SP may be based on a predetermined temperature level associated with a burn risk above a certain threshold. The temperature SP may represent a body/core temperature of the patient.

At decision block 9906, the process 9900 involves determining whether the PV of a given area of the patient's body is lower than the SP value relevant for that area. If the PV is lower than the SP value, the process 9900 continues to block 9908. If the PV is equal to or greater than the SP value, the process 9900 continues to block 9914.

At block 9908, the process 9900 involves measuring the patient's skin temperature (T). The skin temperature T may be measured to determine a risk of burning at the patient's skin. At block 9910, the process 9900 involves determining a skin heat safety threshold (TMAX), wherein the determination at block 9912 may be based at least in part on the threshold TMAX. TMAX may be indicative of a temperature at which the patient may be at risk of localized burning.

At decision block 9912, the process 9900 involves determining whether T is less than TMAX, T is less than TMAX, the process 9900 continues to block 9916. If T is equal to or greater than TMAX, the process 9900 continues to block 9914.

At block 9914, the process 9900 involves deactivating or otherwise disabling or throttling one or more heating element at the given area of the patient's body. At block 9916, the process 9900 involves enabling and/or increasing activity of the heating element(s) (e.g., increasing the duty cycle).

An applied potential and/or adjustment in duty cycle of a heating element at a sleeve may be modulated based on proportional, integral (Ki), and/or derivative adjustments in response to measured error in temperature as compared to the target temperature. In some embodiments, the further away from the target temperature, the more power is applied to the heating element(s) and/or compression element(s). An integral component may allow for correction of an offset error. A derivative component may be useful in reducing a transient time effect (e.g., overshoot).

In some embodiments, a temperature-management controller may be configured to use individually-actuated heating pads and/or a variety of threshold values (e.g., safe and/or maximum temperature values). The controller may be configured to individually control each heating element based at least in part on each respective threshold value.

Figure 30:
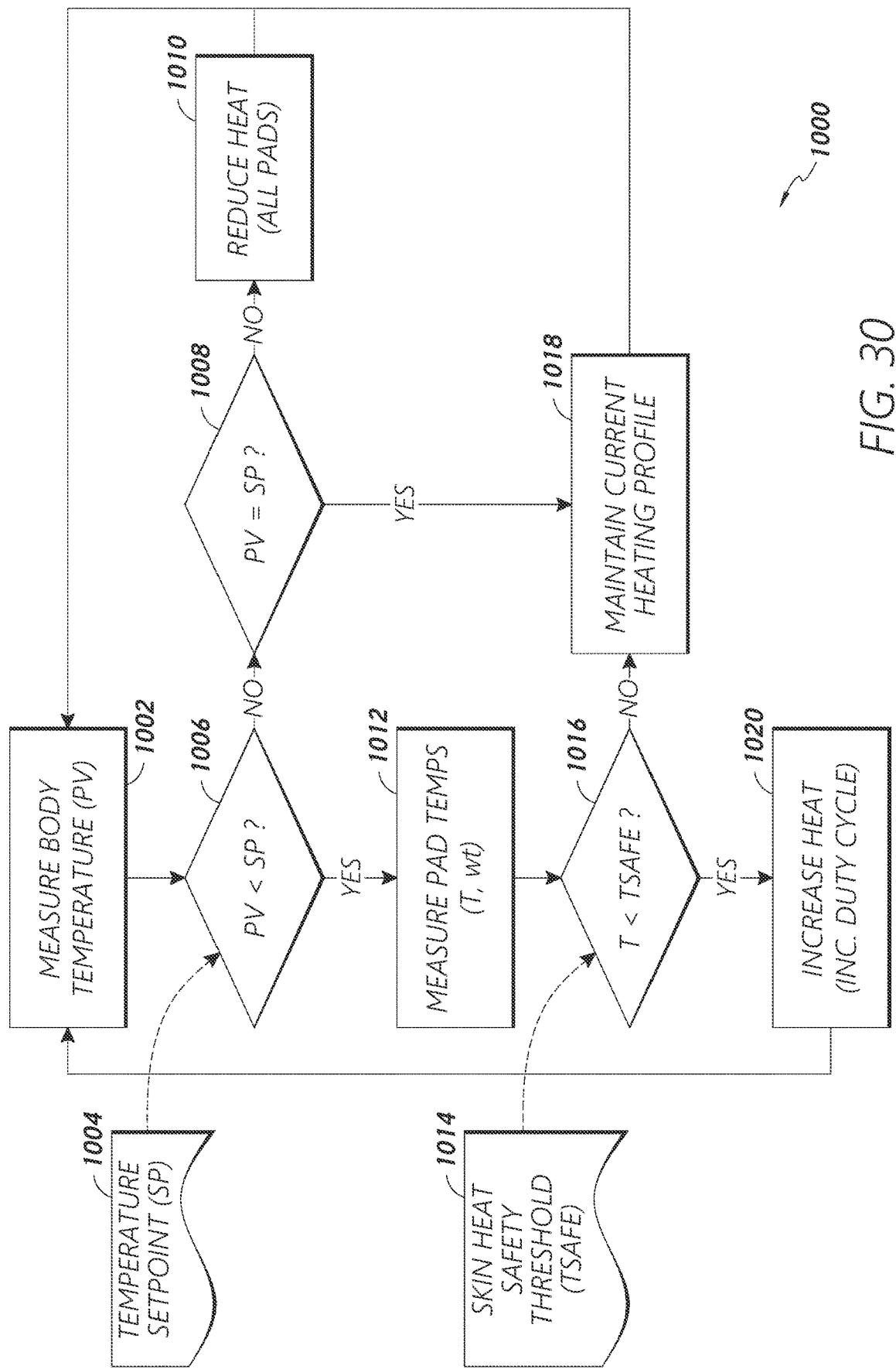
FIG. 30 provides a process for increasing temperature at heating elements at sleeve devices providing heat to a patient in accordance with some embodiments.

FIG. 30 provides a process 1000 for increasing temperature at heating elements of sleeve devices providing heat to a patient in accordance with aspects of the present disclosure. The process 1000 may be implemented in whole or in part by certain control circuitry of a temperature-management system, such as by control circuitry associated with one or both of a temperature-management controller and a temperature-management device (e.g., wearable sleeve device), as may be similar in certain respects to corresponding components in the system 110 of FIG. 23, described in detail above.

At block 1002, the process 1000 involves measuring and/or estimating a present value (PV) of the patient's body temperature. For example, the measured/estimated temperature may be directly-measured core temperature or may be estimated temperature based on measured peripheral (e.g., skin) temperature. In some embodiments, the temperature PV may be measured using one or more sensors attached to and/or otherwise used in conjunction with a sleeve administered to, or otherwise disposed on, the patient.

At block 1004, the process 1000 involves determining a temperature set point (SP) (e.g., target temperature value). In some embodiments, different areas of a patient's body may have different SP values. The temperature SP may be based on a predetermined temperature level associated with a burn risk above a certain threshold. The temperature SP may represent a body/core temperature of the patient.

At decision block 1006, the process 1000 involves determining whether the PV of a given area of the patient's body is lower than the SP value relevant for that area. If the PV is lower than the SP value, the process 1000 continues to block 1012. If the PV is equal to or greater than the SP value, the process 1000 continues to block 1008.

At block 1008, the process 1000 involves determining whether PV is equal to the SP value. If PV is equal to SP, the process 1000 continues to block 1018. If PV is not equal to SP, the process 1000 continues to block 1010.

At block 1010, the process 1000 involves reducing heat at one or more heating elements (e.g., pads) associated with one or more sleeves administered to, or otherwise disposed on, the patient.

At block 1012, the process 1000 involves measuring temperatures (T) at heating elements (e.g., pads). For example, heating elements may have temperature sensor(s) (e.g., thermistor(s)) associated therewith. At block 1014, the process 1000 involves determining a skin heat safety threshold value (TSAFE). At decision block 1016, the process 1000 involves determining whether T is less than TSAFE. If T is less than TSAFE, the process 1000 continues to block 1020. If T greater than or equal to TSAFE, the process 1000 continues to block 1018.

At block 1018, the process 1000 involves maintaining the current heating profile at one or more heating elements. At block 1020, the process 1000 involves increasing heat (e.g., increasing the duty cycle) at one or more heating elements.

In some embodiments, a temperature-management controller may treat multiple heating dements as a single element/transducer. For example, the controller may be configured to set the heating elements to a single common temperature and/or drive the heating elements using common or similar control signals. However, in some cases, one or more heating elements may reach the skin heat safety threshold (TSAFE) while the core body temperature remains below the set point. In such cases, the controller may be configured to increase heating element temperatures from TSAFE to a higher maximum temperature (TMAX) for a limited duration. In some cases, at least some areas of tissue may be heated to TMAX for a period of time without burning. Accordingly, temperature at one or more heating elements may be cycled higher and lower. The controller may be configured to alternate heating and non-heating (e.g., coding) between TSAFE and TMAX as between heating elements at different limbs to maintain elevated blood temperature in each limb. In such embodiments, a first heating dement (e.g., at the popliteal fossa of the left leg) may be heated towards TMAX while a second heating element (e.g., at the foot of the left leg) may be heat-throttled/cooled towards TSAFE.

Figure 31:
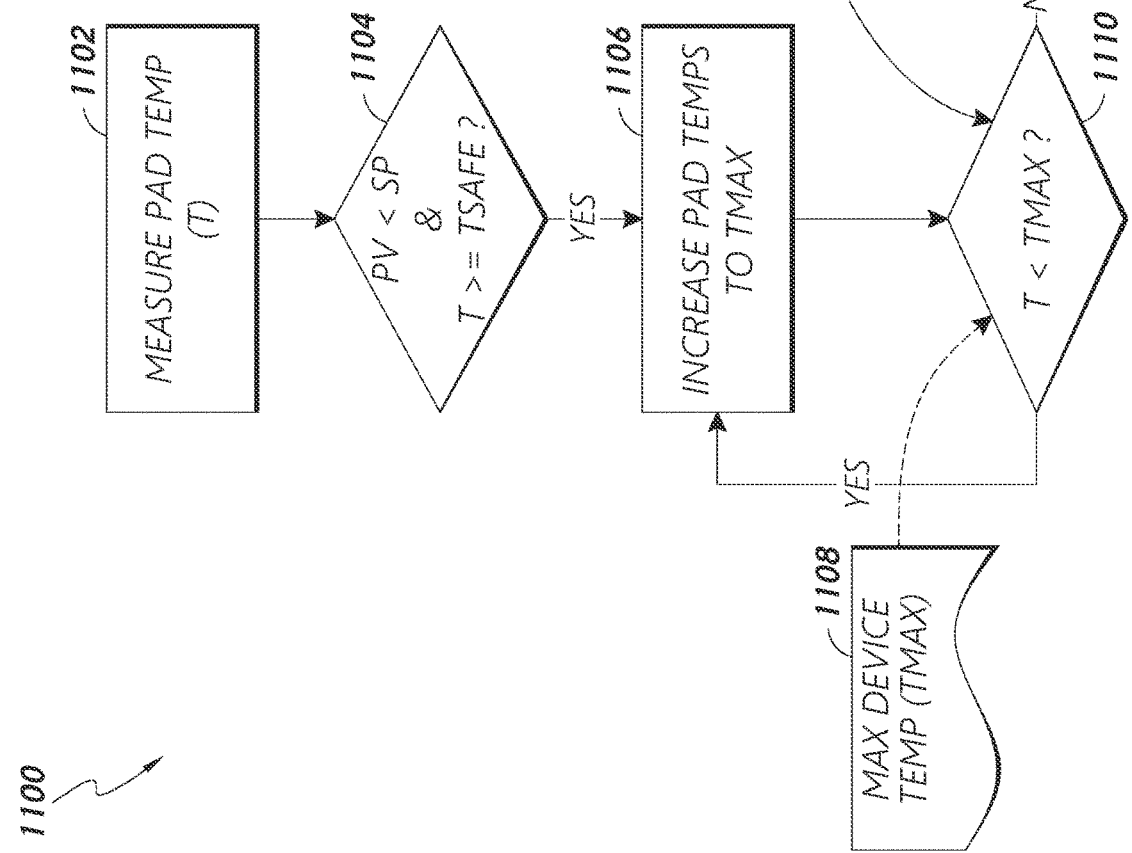
FIG. 31 illustrates a process for controlling a heating element of a sleeve in accordance with some embodiments.

In some embodiments, activation/heating of different heating elements may be offset in time (e.g. by one cooldown period) in order to achieve a desired alternating heat profile. FIG. 31 illustrates a process 1100 for controlling a heating element of a sleeve in accordance with one or more embodiment of the present disclosure. The process 1100 may be implemented in whole or in part by certain control circuitry of a temperature-management system, such as by control circuitry associated with one or both of a temperature-management controller and a temperature-management device (e.g., wearable sleeve device), as may be similar in certain respects to corresponding components in the system 110 of FIG. 23, described in detail above.

At block 1102, the process 1100 involves measuring a heating element (e.g., pad) temperature (T). At decision block 1104, the process 1100 may involve determining whether a present measured and/or estimated value (PV) of a patient's body/core temperature is lower than a set point temperature value (SP) and whether T is greater than or equal to a skin heat safety threshold value (TSAFE). If PV is less than SP and T is greater than or equal to TSAFE, the process 1100 continues to block 1106.

At block 1106, the process 1100 involves increasing T to a maximum temperature value (TMAX), which may have previously been determined in connection with the operation(s) associated with block 1108. At decision block 1110, the process 1100 involves determining whether T is less than TMAX. If T is not less than TMAX, the process 1100 proceeds to block 1112.

At block 1112, the process 1100 involves decreasing T to TSAFE in some manner, such as by throttling/deactivating the heating element/pad associated with the temperature T. At block 1114, the process 1100 involves waiting for a period (e.g., one cooldown period), which may be any suitable or desirable period of time that is sufficient for the temperature T of the heating element(s) to drop below TMAX.

A temperature-management controller may be configured to operate within safe limits for temperature applied to skin tissue to avoid burns. Generally, for reference, certain human tissue may start to burn at temperatures above approximately 43° C. In some embodiments, tissue burn monitoring may be achieved through peripheral temperature probes placed between heating elements and patient skin. Peripheral temperatures may be translated into estimated tissue temperature using a physiological heat transfer model that can account for heat transfer through both tissue and heating sleeve materials.

The temperature-management controller can be designed with safety considerations in place to limit heating element temperature based on "heat capacity" of the surrounding tissue. For example, the controller may evaluate historical pad temperatures to monitor precisely the amount of time skin temperature has exceeded the safe threshold (e.g., 43° C.) and may adjust TMAX and/or cooldown periods accordingly. Various safety measures may include visual/audible alerts and/or warnings generated and/or provided by a controller in response to detected risks of, for example, tissue burning and/or hypothermia. Such safety measures may be configured to prompt clinicians to take particular actions to correct detected errors. For example, a safety measure may prompt a clinician to check a device connection and/or sleeve placement alignment, etc.

Deep vein thrombosis (DVT) prophylaxis can operate through sequential compression of the calf to increase circulation of blood throughout the body. Changes to the compression sequence may be implemented to modify the rate of blood flow. In some embodiments, venous return rate may be maintained at a sufficiently elevated level to prevent DVT. Heat transfer into tissue (and/or blood in underlying vessels) may occur on a comparable (or faster) time scale to the rate of compression. Venous return rate adjustments can affect the amount of heat that may be returned to the body's core by one or more sleeves.

Some embodiments may involve using independently controlled heating elements with adjustments for compression. For example, sleeve pressure ratings and/or compression frequency may be controlled in conjunction with heating at one or more sleeves.

Figure 32:
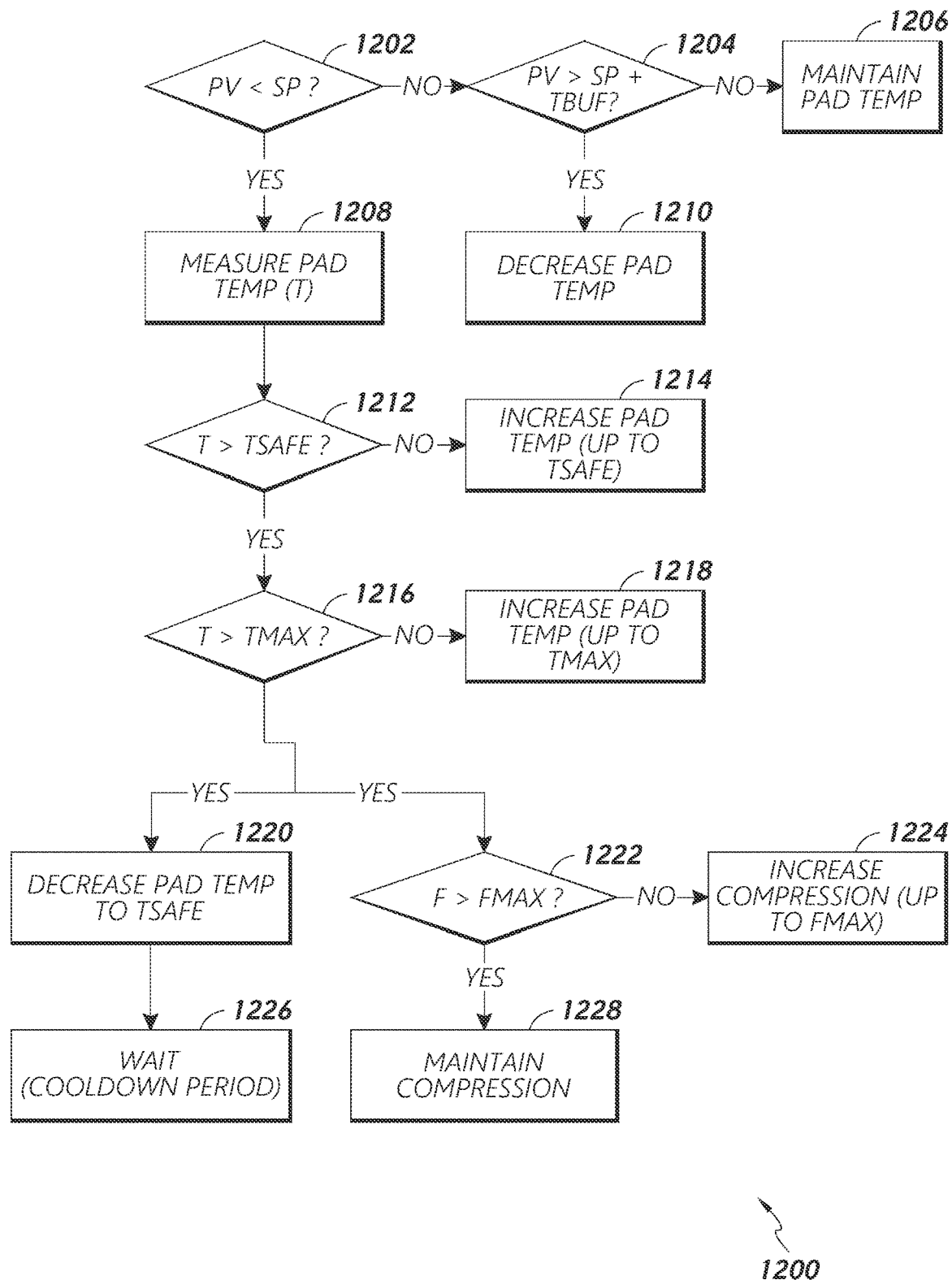
FIG. 32 provides a process for increasing and/or maintaining patient temperature using a sleeve configured to provide heat and/or compression to a patient in accordance with some embodiments.

FIG. 32 provides a process 1200 for increasing and/or maintaining patient temperature using a sleeve configured to provide heat and/or compression to a patient. The process 1200 may be implemented in whole or in part by certain control circuitry of a temperature-management system, such as by control circuitry associated with one or both of a temperature-management controller and a temperature-management device (e.g., wearable sleeve device), as may be similar in certain respects to corresponding components in the system 110 of FIG. 23, described in detail above.

At decision block 1202, the process 1200 involves determining whether a present value of a patient's body temperature (PV) is less than a set point temperature value (SP). If PV is less that SP, the process 1200 proceeds to block 1208. If PV is greater than or equal to SP, the process 1200 proceeds to block 1204.

At decision block 1204, the process 1200 involves determining whether PV is greater than a sum of SP and a buffer value (TBUF). TBUF (e.g., −1° C.) may be configured to prevent rapid oscillation in heat output around SP. If PV is greater than the sum, the process 1200 proceeds to block 1210. If PV is not greater than the sum, the process 1200 proceeds to block 1206. At block 1206, the process 1200 involves maintaining temperature at one or more heating elements (e.g., pads).

At block 1208, the process 1200 involves measuring a temperature at one or more heating elements (T). At block 1210, the process 1200 involves decreasing the temperature at one or more heating elements.

At decision block 1212, the process 1200 involves determining whether T is greater than a safe heating element temperature threshold (TSAFE) to avoid burning tissue. If T is greater than TSAFE, the process 1200 proceeds to decision block 1216. If T is not greater than TSAFE, the process 1200 proceeds to block 1214. At block 1214, the process 1200 involves increasing T up to TSAFE.

At decision block 1216, the process 1200 involves determining whether T is greater than a maximum heating element temperature (TMAX) that is greater than TSAFE. Heat application between TSAFE and TMAX may be cycled to prevent tissue burning. If T is greater than TMAX, the process 1200 proceeds to block 1220 and decision block 1222. If T is not greater than TMAX, the process 1200 proceeds to block 1218. At block 1218, the process 1200 involves increasing T to TMAX. At block 1220, the process 1200 involves decreasing T to TSAFE. At block 1226, the process 1200 involves waiting a period (e.g., one cooldown period).

In some embodiments, steps of the process 1200 may be performed iteratively and/or cyclically. For example, after one or more heating elements are activated to increase T at blocks 1214 and/or 1218, the process 1200 may start over at decision block 1202 after a given period of time. In some embodiments, the number of times the process 1200 is repeated in which T is increased may indicate a safety concern and/or may cause activation of an alert/warning. For example, if T is increased for a particular amount of time, an alert at a controller may be activated to indicate to a clinician that the patient's body temperature is not increasing despite the activation of heating elements. Failure to increase the patient's body temperature may indicate failure of one or more heating elements and/or physiological issues of the patient.

At decision block 1222, the process 1200 involves determining whether a compression frequency (F) at one or more compression elements of the sleeve is greater than a maximum frequency of applied sequential compression (FMAX). If F is greater than FMAX, the process 1200 proceeds to block 1228. If F is not greater than FMAX, the process 1200 proceeds to block 1224. At block 1224, the process 1200 involves increasing F to FMAX. At block 1228, the process 1200 involves maintaining F.

In some embodiments, sleeve compression for DVT prophylaxis may have a range of acceptable pressure and frequency to achieve deep vessel collapse. Compression periodicity may oscillate (e.g., between 20 and 60 seconds). This range may be based at least in part on accepted clinical ranges for DVT prophylaxis therapy. The compression amplitude of a sleeve may be controlled by a compression chamber pressure. The applied pressure may range from 40-100 mmHg. Higher pressures may increase the peak blood flow velocity.

Additional Possible Implementation Details

In some embodiments described herein, a system/device may be configured to manage core body temperature via compression and warming. Warming may be applied to at least the popliteal fossa and sole of the foot of a patient. In some embodiments, warming may be delivered via conductive means, mainly by the use of resistive heating or a fluid-warmed bladder. The contact between the conductive heating element and the patient limb may be maintained through the use of a limb-biasing apparatus (e.g. foam, bladder, or strap positioned between the heating element and the outer sleeve layer, wherein upon inflation or application, surface contact between the heating element the leg and the leg is created and/or maintained). In some embodiments, limb-biasing feature may be used for warming methods other conductive heat transfer. For example, warming bladders may be configured to create a pocket/cavity to direct temperature-controlled fluid and/or gas to a patient's skin.

Warming may be delivered via convective means, mainly by a system to provide pressurized, thermally treated gas to a convective warming device by way of an air-tight and/or water-tight hose. The system may comprise a forced gas warming unit for providing a stream of pressurized warm gas (e.g., 27° C.-50.5° C.) through channels or bladders within the sleeve. The system may further comprise a heater in the forced-air warming unit, a control circuit in the forced air warming unit, and/or a limb sleeve with perforation connected to the forced-air warming unit.

In some embodiments, warming temperature may be cyclical so as to avoid burning of the skin. One or more heating elements may be configured to deliver heat in a controlled manner (e.g., via pulse-width modulation). In some embodiments, a heat application cycle may be synced (with some offset) in time to the cycles of compression. Compression may be applied to at least the calf of a patient.

Some embodiments may involve a method of intuitively placing a limb sleeve. The sleeve may comprise one or more physical, visible, and/or palpable anomalies or markers in the sleeve structure that indicate unique anatomical placement (e.g., a hole for knee and heel) and/or orientation (e.g., patient-facing surfaces). In some embodiments, a sleeve may comprise extendable and/or collapsible sections within the sleeve body that enable universal placement of single size sleeve (e.g. dimensionally adjustable and/or elastic regions that may enable the knee region, ankle, and foot region to be stretched to a desired length prior to application).

A universal interface connector may be situated between the sleeve and controller. The interface may be configured to maintain a hermetic seal between the internal fluid and electric channels. In some embodiments, the interface may be configured to maintain a hermetic seal to the external environment. The interface can be attached in a single or multiple fixation orientations. For example, the interface may be configured to maintain a hermetic seal with only one of the internal fluid and electric channels.

In some embodiments, a connector interface may comprise multiple (e.g., three) air-tight and/or water-tight channels, multiple (e.g., two) heating channels, multiple (e.g., two) sensor/feedback channels, and/or at least one ground channel. The interface may comprise one connector per sleeve to support a compression element, heating elements, and/or temperature sensors. A compression channel may take the form of multiple (e.g., three or more) air-tight and/or water-tight channels. Heating, sensor, and/or ground channels may be watertight. In some embodiments, heating, sensor, and/or ground channels may be configured to provide electrical connection achieved through conducting pins to either of multiple configurations. A controller may be situated on one end and a connecting cable may be situated on a second end. In other embodiments, a connecting cable may be situated on one end and a sleeve may be situated on a second end. In some embodiments, a controller may be situated on one end and a sleeve may be situated on a second end.

A connector may comprise multiple (e.g., two) regions separating air-tight and water-tight regions. Air-tightness may be achieved through an O-ring and/or nozzle and/or hose interface for each channel. Water-tightness may be achieved through an O-ring for the entire watertight compartment. In some embodiments, a connector may comprise physical latching features to allow the connector and parts to be connected (i.e., joined) or disconnected (i.e., separated) easily. The connector may comprise an asymmetric interface and/or other physical features designed to prevent incorrect orientation in the connection between controller, cable, and/or sleeve. In some embodiments, the connector may comprise visual locating features to assist in orientation and/or implementation/removal of the air-tight/water-tight connection between controller, cable, and/or sleeve. The connector may comprise physical design characteristics such that either compression or heating may be excluded (optional components) on the cable/sleeve connection side.

In some embodiments, a connector may comprise a single compartment encompassing both air-tight and watertight regions such that air-tightness may be achieved through O-ring and/or nozzle/hose interface for each air-tight channel. Water-tightness may be achieved through an O-ring around the entire compartment. The connector may comprise two independent components (e.g., one each of compression and heating) that may be optionally joined by cabling or within the sleeve.

A controller may comprise one or more temperature monitors configured to determine gas (e.g., air) temperature as the gas enters the hoses on the way to the sleeve. In some embodiments, the controller may utilize an on/off switch set at approximately 43° C. A conductive channel may be utilized to support temperature sensors.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first" "second," "third," etc.) used to modify an element, such as a structure, a component, an operation, etc., does not necessarily indicate priority or order of the element with respect to any other element, but rather may generally distinguish the element from another element having a similar or identical name (hut for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more." "greater," and the like, are intended to encompass the concepts of equality. For example, "less" can mean not only "less" in the strictest mathematical sense, but also, "less than or equal to."

What is claimed is:

1. A wearable heating sleeve comprising:
a first sleeve portion configured to be secured to a popliteal fossa of a patient's leg;
a first heating pad coupled to the first sleeve portion;
a second sleeve portion configured to be secured to a foot of the patient's leg;
a second heating pad coupled to the second sleeve portion;
one or more temperature sensors associated with at least one of the first sleeve portion or the second sleeve portion;
a third sleeve portion configured to be secured to a calf of the patient's leg;
one or more compression bladders associated with the third sleeve portion; and
control circuitry electrically coupled to the first heating pad, the second heating pad, and the one or more temperature sensors, the control circuitry configured to:
determine a first risk weight based on a surgery classification of a surgical operation associated with the patient;
determine a second risk weight based on an anesthesia condition of the patient;
receive one or more temperature signals from the one or more temperature sensors;
determine an estimated core temperature of the patient based on the one or more temperature signals;
determine a third risk weight based on the estimated core temperature;
determine a risk value associated with the patient based at least in part on a weighted, normalized summation of the first risk weight, the second risk weight, and the third risk weight; and
at least partly in response to the risk value, activate the first heating pad, the second heating pad, and the one or more compression bladders.

2. The wearable heating sleeve of claim 1, wherein the control circuitry is electrically coupled to the first heating pad, the second heating pad, and the one or more temperature sensors at least in part by conductive wiring that extends externally of the first, second, and third sleeve portions.

3. The wearable heating sleeve of claim 1, wherein the control circuitry is further configured to, based at least in part on the estimated core temperature, determine an amount of time until hypothermia is estimated to occur.

4. A heating system comprising:
a wearable sleeve;
a first heating pad associated with a first portion of the wearable sleeve;
a second heating pad associated with a second portion of the wearable sleeve;
one or more temperature sensors associated with the wearable sleeve; and
control circuitry communicatively coupled to the first heating pad, the second heating pad, and the one or more temperature sensors, the control circuitry configured to:
receive one or more temperature signals from the one or more temperature sensors;
estimate a core temperature associated with a patient based on the one or more temperature signals;
determine a temperature error value representing an error between the estimated core temperature and a target temperature value;
determine a proportional control component based on the temperature error value;
determine an integral control component based on an accumulated sum of past temperature error values;
determine a derivative control component based on a rate of change of the temperature error value; and
activate at least one of the first heating pad or the second heating pad based on the proportional control component, the integral control component, and the derivative control component.

5. The heating system of claim 4, further comprising one or more compression devices associated with a third portion of the wearable sleeve.

6. The heating system of claim 5, wherein the control circuitry is further configured to, in response to the proportional control component, the integral control component, and the derivative control component, activate the one or more compression devices.

7. The heating system of claim 4, wherein:
the first heating pad is a popliteal fossa heating pad;
the second heating pad is a foot heating pad; and
the control circuitry is configured to perform said activating at least one of the first heating pad or the second heating pad by activating the popliteal fossa heating pad and the foot heating pad between a maximum temperature and a minimum temperature such that the popliteal fossa heating pad reaches the minimum temperature when the foot heating pad is at the maximum temperature and the foot heating pad reaches the minimum temperature when the popliteal fossa heating pad is at the maximum temperature.

8. The heating system of claim 4, wherein the control circuitry is further configured to generate a time value parameter indicating a period of time expected until the patient is in range of hypothermia based at least in part the one or more temperature signals.

9. The heating system of claim 4, wherein:
the control circuitry is further configured to determine an anesthesia state of the patient; and
said activating the at least one of the first heating pad or the second heating pad is based at least in part on the anesthesia state of the patient.

10. The heating system of claim 9, wherein said determining the anesthesia state of the patient is based at least in part on a detection that a heart rate of the patient has dropped a threshold amount.

11. The heating system of claim 9, wherein a weight assigned to the anesthesia state of the patient decreases over time.

12. The heating system of claim 4, wherein the control circuitry is further configured to determine a hypothermia risk value based at least in part on the estimated core temperature.

13. The heating system of claim 12, wherein said hypothermia risk value is based at least in part on a weighted combination of at least one dynamic parameter and at least one static parameter, each of the at least one dynamic parameter and the at least one static parameter having associated therewith a risk weight.

14. The heating system of claim 13, wherein:
the at least one dynamic parameter comprises at least one of the estimated core temperature, patient skin temperature, environmental temperature, or a patient vital signal level; and
the at least one static parameter comprises at least one of patient demographic group, patient comorbidity status, or procedure type.

15. The heating system of claim 4, wherein the estimated core temperature is a predicted future body temperature of the patient that is based at least in part on the one or more temperature signals and a rate of change of the one or more temperature signals.

16. The heating system of claim 15, wherein the predicted future body temperature is further based at least in part on anesthesia depth.

17. The heating system of claim 4, wherein said activating at least one of the first heating pad or the second heating pad involves alternating activation of the first heating pad and the second heating pad.

18. The heating system of claim 4, wherein:
the control circuitry is further configured to:
determine a skin temperature of the patient based on the one or more temperature signals;
determine that the skin temperature is greater than a safety threshold; and
at least partly in response to said determining that the skin temperature is greater than the safety threshold, deactivate at least one of the first heating pad or the second heating pad.

19. The heating system of claim 4, wherein the control circuitry is embodied, at least in part, in a controller electrically and physically couplable to the wearable sleeve via one or more cables.

20. The heating system of claim 4, wherein the control circuitry is embodied, at least in part, in a controller communicatively couplable to at least one of the first heating pad, the second heating pad, or the one or more temperature sensors via a wireless connection.

* * * * *